United States Patent
Tian et al.

(10) Patent No.: US 12,421,511 B2
(45) Date of Patent: Sep. 23, 2025

(54) MUTANT PROTEIN FOR IMPROVING MALIC ACID YIELD

(71) Applicant: TIANJIN INSTITUTE OF INDUSTRIAL BIOTECHNOLOGY, CHINESE ACADEMY OF SCIENCES, Tianjin (CN)

(72) Inventors: Chaoguang Tian, Tianjin (CN); Junqi Zhao, Tianjin (CN); Jingen Li, Tianjin (CN); Lu Zhang, Tianjin (CN)

(73) Assignee: TIANJIN INSTITUTE OF INDUSTRIAL BIOTECHNOLOGY, CHINESE ACADEMY OF SCIENCES, Tianjin (CN)

( * ) Notice: Subject to any disclaimer, the term of this patent is extended or adjusted under 35 U.S.C. 154(b) by 1038 days.

(21) Appl. No.: 17/286,636

(22) PCT Filed: Oct. 18, 2019

(86) PCT No.: PCT/CN2019/112010
§ 371 (c)(1),
(2) Date: Apr. 19, 2021

(87) PCT Pub. No.: WO2020/078474
PCT Pub. Date: Apr. 23, 2020

(65) Prior Publication Data
US 2021/0371844 A1    Dec. 2, 2021

(30) Foreign Application Priority Data
Oct. 19, 2018 (CN) .......................... 201811223531.1

(51) Int. Cl.
*C12N 9/00*    (2006.01)
*C07K 14/37*    (2006.01)
*C12P 7/46*    (2006.01)

(52) U.S. Cl.
CPC ................ *C12N 9/93* (2013.01); *C07K 14/37* (2013.01); *C12P 7/46* (2013.01); *C12Y 604/01001* (2013.01)

(58) Field of Classification Search
CPC .......... C12N 9/93; C07K 14/37; C07K 14/38; C07K 14/39; C07K 14/415; C12P 7/46; C12Y 604/01001; C12R 2001/645; C12R 2001/865
See application file for complete search history.

(56) References Cited

PUBLICATIONS

Biao et al. (Biochemistry, 2004, 43:5912-5920) (Year: 2004).*
Peters-Wendisch et al. (Microbiol, 1998, 144:915-927) (Year: 1998).*
UniProt Database Accession No. Q79VI3 (Jul. 2018, 3 pages) (Year: 2018).*
GenPept Database Accession No. OOO13927.1 (Feb. 2017, 2 pages) (Year: 2017).*
Dai et al. (Biores Technol, 2018, 258:345-353) (Year: 2018).*
Chen et al. (Appl Microbiol Biotechnol, 2017, 101:4041-4052) (Year: 2017).*
UniProt Database Accession No. MAE1_SCHPO (Oct. 1, 1996, 3 pages) (Year: 1996).*
Peti et al. (Protein Expression Purif, 2007, 51:1) (Year: 2007).*
International Search Report and Written Opinion; PCT Application No. PCT/CN2019/112010; mailed Jan. 21, 2020.
English translation of International Search Report and Written Opinion; PCT Application No. PCT/CN2019/112010; mailed Jan. 21, 2020; retrieved from Patentscope on Aug. 19, 2021.
Pyruvate carboxylase [*Corynebacterium glutamicum*]; NCBI Reference Sequence: WP: 011013816.1; retrieved from https://www.ncbi.nlm.nih.gov/protein/WP_011013816.1/ on Apr. 19, 2021; ORGIN sequences.

* cited by examiner

*Primary Examiner* — David Steadman
*Assistant Examiner* — Joseph R Spangler
(74) *Attorney, Agent, or Firm* — NKL Law; Bin Lu; Allen Xue

(57) ABSTRACT

The present invention provides a class of new mutant proteins for increasing malic acid yield. Specifically, the present invention provides a class of new pyruvate carboxylase mutant protein and malic acid transporter mutant proteins or combinations thereof, a preparation method therefor and use thereof in improving malic acid yield.

17 Claims, 14 Drawing Sheets
Specification includes a Sequence Listing.

US 12,421,511 B2

SEQUENCE LISTING

```
<160> NUMBER OF SEQ ID NOS: 176

<210> SEQ ID NO 1
<211> LENGTH: 1140
<212> TYPE: PRT
<213> ORGANISM: Corynebacterium glutamicum

<400> SEQUENCE: 1

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60
```

-continued

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro

```
                      485                 490                 495
Ile Asp Lys Leu Pro Asn Ile Lys Asp Leu Pro Leu Pro Arg Gly Ser
                500                 505                 510

Arg Asp Arg Leu Lys Gln Leu Gly Pro Ala Ala Phe Ala Arg Asp Leu
                515                 520                 525

Arg Glu Gln Asp Ala Leu Ala Val Thr Asp Thr Phe Arg Asp Ala
                530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
                580                 585                 590

Asp Pro Trp Asp Arg Leu Asp Glu Leu Arg Glu Ala Met Pro Asn Val
                595                 600                 605

Asn Ile Gln Met Leu Leu Arg Gly Arg Asn Thr Val Gly Tyr Thr Pro
                610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
                675                 680                 685

Leu Tyr Thr Leu Asp Tyr Tyr Leu Lys Met Ala Glu Glu Ile Val Lys
                690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
                740                 745                 750

Thr Tyr Phe Ala Ala Ala Gln Ala Gly Ala Asp Ala Val Asp Gly Ala
                755                 760                 765

Ser Ala Pro Leu Ser Gly Thr Thr Ser Gln Pro Ser Leu Ser Ala Ile
                770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
                820                 825                 830

His Glu Ile Pro Gly Gly Gln Leu Ser Asn Leu Arg Ala Gln Ala Thr
                835                 840                 845

Ala Leu Gly Leu Ala Asp Arg Phe Glu Leu Ile Glu Asp Asn Tyr Ala
                850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910
```

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
            995                 1000                1005

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
    1130                1135                1140

<210> SEQ ID NO 2
<211> LENGTH: 1140
<212> TYPE: PRT
<213> ORGANISM: artificial sequence
<220> FEATURE:
<223> OTHER INFORMATION: mutant protein

<400> SEQUENCE: 2

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
                20                  25                  30

Glu Thr Gly Ala Ala Thr Val Ala Ile Tyr Pro Arg Glu Asp Arg Gly
            35                  40                  45

Ser Phe His Arg Ser Phe Ala Ser Glu Ala Val Arg Ile Gly Thr Glu
        50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

```
Arg Ala Val Thr Ala Ala Lys Lys Ala Gly Leu Pro Val Leu Ala Glu
130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Pro His Leu Leu Gln Ala Pro
450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
530                 535                 540
```

-continued

| His<br>545 | Gln | Ser | Leu | Leu<br>550 | Ala | Thr | Arg | Val | Arg<br>555 | Ser | Phe | Ala | Leu | Lys<br>560 | Pro |

Ala Ala Glu Ala Val Ala Lys Leu Thr Pro Glu Leu Leu Ser Val Glu
      565                 570                 575

Ala Trp Gly Gly Ala Thr Tyr Asp Val Ala Met Arg Phe Leu Phe Glu
          580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
              645                 650                 655

Met Arg Pro Ala Ile Asp Ala Val Leu Glu Thr Asn Thr Ala Val Ala
          660                 665                 670

Glu Val Ala Met Ala Tyr Ser Gly Asp Leu Ser Asp Pro Asn Glu Lys
              675                 680                 685

Leu Tyr Thr Leu Asp Tyr Tyr Leu Lys Met Ala Glu Glu Ile Val Lys
      690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                  725                 730                 735

Leu Pro Val His Val His Thr His Asp Thr Ala Gly Gly Gln Leu Ala
              740                 745                 750

Thr Tyr Phe Ala Ala Ala Gln Ala Gly Asp Ala Val Asp Gly Ala
          755                 760                 765

Ser Ala Pro Leu Ser Gly Thr Thr Ser Gln Pro Ser Leu Ser Ala Ile
  770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
              805                 810                 815

Leu Pro Phe Glu Ser Gly Thr Pro Gly Pro Thr Gly Arg Val Tyr Arg
          820                 825                 830

His Glu Ile Pro Gly Gly Gln Leu Ser Asn Leu Arg Ala Gln Ala Thr
              835                 840                 845

Ala Leu Gly Leu Ala Asp Arg Phe Glu Leu Ile Glu Asp Asn Tyr Ala
  850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                  885                 890                 895

Pro Ala Asp Phe Ala Ala Asp Pro Gln Lys Tyr Asp Ile Pro Asp Ser
          900                 905                 910

Val Ile Ala Phe Leu Arg Gly Glu Leu Gly Asn Pro Gly Gly Trp
              915                 920                 925

Pro Glu Pro Leu Arg Thr Arg Ala Leu Glu Gly Arg Ser Glu Gly Lys
      930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro

```
              965                 970                 975
Lys Pro Thr Glu Glu Phe Leu Glu His Arg Arg Phe Gly Asn Thr
            980                 985                 990

Ser Ala Leu Asp Asp Arg Glu Phe Phe Tyr Gly Leu Val Glu Gly Arg
        995                1000                1005

Glu Thr Leu Ile Arg Leu Pro Asp Val Arg Thr Pro Leu Leu Val
       1010                1015                1020

Arg Leu Asp Ala Ile Ser Glu Pro Asp Asp Lys Gly Met Arg Asn
       1025                1030                1035

Val Val Ala Asn Val Asn Gly Gln Ile Arg Pro Met Arg Val Arg
       1040                1045                1050

Asp Arg Ser Val Glu Ser Val Thr Ala Thr Ala Glu Lys Ala Asp
       1055                1060                1065

Ser Ser Asn Lys Gly His Val Ala Ala Pro Phe Ala Gly Val Val
       1070                1075                1080

Thr Val Thr Val Ala Glu Gly Asp Glu Val Lys Ala Gly Asp Ala
       1085                1090                1095

Val Ala Ile Ile Glu Ala Met Lys Met Glu Ala Thr Ile Thr Ala
       1100                1105                1110

Ser Val Asp Gly Lys Ile Asp Arg Val Val Val Pro Ala Ala Thr
       1115                1120                1125

Lys Val Glu Gly Gly Asp Leu Ile Val Val Ser
       1130                1135                1140
```

<210> SEQ ID NO 3
<211> LENGTH: 1140
<212> TYPE: PRT
<213> ORGANISM: artificial sequence
<220> FEATURE:
<223> OTHER INFORMATION: mutant protein

<400> SEQUENCE: 3

```
Met Ser Thr His Thr Ser Ser Thr Leu Pro Ala Phe Lys Lys Ile Leu
1               5                  10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
     50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
```

```
              180                 185                 190
Glu Ala Ser Arg Glu Ala Glu Ala Phe Gly Asp Gly Ala Val Tyr
        195                 200                 205
Val Glu Arg Ala Val Ile Asn Pro Gln His Ile Glu Val Gln Ile Leu
        210                 215                 220
Gly Asp His Thr Gly Glu Val Val His Leu Tyr Glu Arg Asp Cys Ser
225                 230                 235                 240
Leu Gln Arg Arg His Gln Lys Val Val Glu Ile Ala Pro Ala Gln His
                245                 250                 255
Leu Asp Pro Glu Leu Arg Asp Arg Ile Cys Ala Asp Ala Val Lys Phe
        260                 265                 270
Cys Arg Ser Ile Gly Tyr Gln Gly Ala Gly Thr Val Glu Phe Leu Val
        275                 280                 285
Asp Glu Lys Gly Asn His Val Phe Ile Glu Met Asn Pro Arg Ile Gln
        290                 295                 300
Val Glu His Thr Val Thr Glu Glu Val Thr Glu Val Asp Leu Val Lys
305                 310                 315                 320
Ala Gln Met Arg Leu Ala Ala Gly Ala Thr Leu Lys Glu Leu Gly Leu
                325                 330                 335
Thr Gln Asp Lys Ile Lys Thr His Gly Ala Ala Leu Gln Cys Arg Ile
                340                 345                 350
Thr Thr Glu Asp Pro Asn Asn Gly Phe Arg Pro Asp Thr Gly Thr Ile
        355                 360                 365
Thr Ala Tyr Arg Ser Pro Gly Gly Ala Gly Val Arg Leu Asp Gly Ala
        370                 375                 380
Ala Gln Leu Gly Gly Glu Ile Thr Ala His Phe Asp Ser Met Leu Val
385                 390                 395                 400
Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
        420                 425                 430
Gly Phe Leu Arg Ala Leu Leu Arg Glu Glu Asp Phe Thr Ser Lys Arg
        435                 440                 445
Ile Ala Thr Gly Phe Ile Ala Asp His Pro His Leu Leu Gln Ala Pro
        450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
                500                 505                 510
Arg Asp Arg Leu Lys Gln Leu Gly Pro Ala Ala Phe Ala Arg Asp Leu
        515                 520                 525
Arg Glu Gln Asp Ala Leu Ala Val Thr Asp Thr Thr Phe Arg Asp Ala
        530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
                580                 585                 590
Asp Pro Trp Asp Arg Leu Asp Glu Leu Arg Glu Ala Met Pro Asn Val
                595                 600                 605
```

```
Asn Ile Gln Met Leu Leu Arg Gly Arg Asn Thr Val Gly Tyr Thr Pro
            610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Glu Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Gly Gly Trp
        915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val
    1010                1015                1020
```

```
Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
    1130                1135                1140

<210> SEQ ID NO 4
<211> LENGTH: 1140
<212> TYPE: PRT
<213> ORGANISM: artificial sequence
<220> FEATURE:
<223> OTHER INFORMATION: mutant protein

<400> SEQUENCE: 4

Met Ser Thr His Thr Ser Ser Thr Leu Pro Ala Phe Lys Lys Ile Leu
1                   5                   10                  15

Val Ala Asn Arg Gly Glu Ile Ala Val Arg Ala Phe Arg Ala Ala Leu
                20                  25                  30

Glu Thr Gly Ala Ala Thr Val Ala Ile Tyr Pro Arg Glu Asp Arg Gly
            35                  40                  45

Ser Phe His Arg Ser Phe Ala Ser Glu Ala Val Arg Ile Gly Thr Glu
        50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240
```

-continued

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala

```
                    660                 665                 670
Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
            690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Val Gly Pro Thr Gly Arg Val Tyr Arg
                820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
        850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
            965                 970                 975

Lys Pro Thr Glu Glu Phe Leu Glu His Arg Arg Arg Phe Gly Asn Thr
        980                 985                 990

Ser Ala Leu Asp Asp Arg Glu Phe Phe Tyr Gly Leu Val Glu Gly Arg
            995                 1000                1005

Glu Thr Leu Ile Arg Leu Pro Asp Val Arg Thr Pro Leu Leu Val
        1010                1015                1020

Arg Leu Asp Ala Ile Ser Glu Pro Asp Lys Gly Met Arg Asn
        1025                1030                1035

Val Val Ala Asn Val Asn Gly Gln Ile Arg Pro Met Arg Val Arg
        1040                1045                1050

Asp Arg Ser Val Glu Ser Val Thr Ala Thr Ala Glu Lys Ala Asp
        1055                1060                1065

Ser Ser Asn Lys Gly His Val Ala Ala Pro Phe Ala Gly Val Val
        1070                1075                1080
```

```
Thr Val Thr Val Ala Glu Gly Asp Glu Val Lys Ala Gly Asp Ala
    1085            1090                1095

Val Ala Ile Ile Glu Ala Met Lys Met Glu Ala Thr Ile Thr Ala
    1100            1105                1110

Ser Val Asp Gly Lys Ile Asp Arg Val Val Pro Ala Ala Thr
    1115            1120                1125

Lys Val Glu Gly Gly Asp Leu Ile Val Val Val Ser
    1130            1135                1140

<210> SEQ ID NO 5
<211> LENGTH: 1140
<212> TYPE: PRT
<213> ORGANISM: artificial sequence
<220> FEATURE:
<223> OTHER INFORMATION: mutant protein

<400> SEQUENCE: 5

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300
```

```
Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
            325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
            355                 360                 365

Thr Ala Tyr Arg Ser Pro Gly Gly Ala Gly Val Arg Leu Asp Gly Ala
            370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
            515                 520                 525

Arg Glu Gln Asp Ala Leu Ala Val Thr Asp Thr Thr Phe Arg Asp Ala
530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
            595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
            690                 695                 700

Ser Gly Ala His Ile Leu Ala Ile Lys Asp Met Ala Gly Leu Leu Arg
705                 710                 715                 720
```

```
Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
    770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                 1005

Glu Thr Leu Ile Arg Leu Pro Asp Val Arg Thr Pro Leu Leu Val
    1010                1015                1020

Arg Leu Asp Ala Ile Ser Glu Glu Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
```

-continued

```
        1130            1135            1140

<210> SEQ ID NO 6
<211> LENGTH: 1140
<212> TYPE: PRT
<213> ORGANISM: artificial sequence
<220> FEATURE:
<223> OTHER INFORMATION: mutant protein

<400> SEQUENCE: 6

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
```

```
              355                 360                 365
Thr Ala Tyr Arg Ser Pro Gly Gly Ala Gly Val Arg Leu Asp Gly Ala
            370                 375                 380
Ala Gln Leu Gly Gly Glu Ile Thr Ala His Phe Asp Ser Met Leu Val
385                 390                 395                 400
Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
                420                 425                 430
Gly Phe Leu Arg Ala Leu Leu Arg Glu Glu Asp Phe Thr Ser Lys Arg
            435                 440                 445
Ile Ala Thr Gly Phe Ile Ala Asp His Pro His Leu Leu Gln Ala Pro
            450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
            500                 505                 510
Arg Asp Arg Leu Lys Gln Leu Gly Pro Ala Ala Phe Ala Arg Asp Leu
            515                 520                 525
Arg Glu Gln Asp Ala Leu Ala Val Thr Asp Thr Thr Phe Arg Asp Ala
            530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
            580                 585                 590
Asp Pro Trp Asp Arg Leu Asp Glu Leu Arg Glu Ala Met Pro Asn Val
            595                 600                 605
Asn Ile Gln Met Leu Leu Arg Gly Arg Asn Thr Val Gly Tyr Thr Pro
        610                 615                 620
Tyr Pro Asp Ser Val Cys Arg Ala Phe Val Lys Glu Ala Ala Ser Ser
625                 630                 635                 640
Gly Val Asp Ile Phe Arg Ile Phe Asp Ala Leu Asn Asp Val Ser Gln
                645                 650                 655
Met Arg Pro Ala Ile Asp Ala Val Leu Glu Thr Asn Thr Ala Val Ala
                660                 665                 670
Glu Val Ala Met Ala Tyr Ser Gly Asp Leu Ser Asp Pro Asn Glu Lys
            675                 680                 685
Leu Tyr Thr Leu Asp Tyr Tyr Leu Lys Met Ala Glu Glu Ile Val Lys
            690                 695                 700
Ser Gly Ala His Ile Leu Ala Ile Lys Asp Met Ala Gly Leu Leu Arg
705                 710                 715                 720
Pro Ala Ala Val Thr Lys Leu Val Thr Ala Leu Arg Arg Glu Phe Asp
                725                 730                 735
Leu Pro Val His Val His Thr His Asp Thr Ala Gly Gly Gln Leu Ala
                740                 745                 750
Thr Tyr Phe Ala Ala Ala Gln Ala Gly Ala Asp Ala Val Asp Gly Ala
            755                 760                 765
Ser Ala Pro Leu Ser Gly Thr Thr Ser Gln Pro Ser Leu Ser Ala Ile
            770                 775                 780
```

```
Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
            805                 810                 815

Leu Pro Phe Glu Ser Gly Thr Pro Gly Pro Thr Gly Arg Val Tyr Arg
            820                 825                 830

His Glu Ile Pro Asp Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
            885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
            930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
            965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
            995                 1000                1005

Glu Thr Leu Ile Arg Leu Pro Asp Val Arg Thr Pro Leu Leu Val
    1010            1015                1020

Arg Leu Asp Ala Ile Ser Glu Pro Asp Lys Gly Met Arg Asn
    1025            1030                1035

Val Val Ala Asn Val Asn Gly Gln Ile Arg Pro Met Arg Val Arg
    1040            1045                1050

Asp Arg Ser Val Glu Ser Val Thr Ala Thr Ala Glu Lys Ala Asp
    1055            1060                1065

Ser Ser Asn Lys Gly His Val Ala Ala Pro Phe Ala Gly Val Val
    1070            1075                1080

Thr Val Thr Val Ala Glu Gly Asp Glu Val Lys Ala Gly Asp Ala
    1085            1090                1095

Val Ala Ile Ile Glu Ala Met Lys Met Glu Ala Thr Ile Thr Ala
    1100            1105                1110

Ser Val Asp Gly Lys Ile Asp Arg Val Val Val Pro Ala Ala Thr
    1115            1120                1125

Lys Val Glu Gly Gly Asp Leu Ile Val Val Val Ser
    1130            1135                1140

<210> SEQ ID NO 7
<211> LENGTH: 1140
<212> TYPE: PRT
<213> ORGANISM: artificial sequence
<220> FEATURE:
<223> OTHER INFORMATION: mutant protein

<400> SEQUENCE: 7
```

-continued

```
Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Lys Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415
```

```
Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
        450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
        755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
```

```
                835                 840                 845
Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
                915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
                980                 985                 990

Ser Ala Leu Asp Asp Arg Glu Phe Phe Tyr Gly Leu Val Glu Gly Arg
                995                 1000                1005

Glu Thr Leu Ile Arg Leu Pro Asp Val Arg Thr Pro Leu Leu Val
        1010                1015                1020

Arg Leu Asp Ala Ile Ser Glu Pro Asp Asp Lys Gly Met Arg Asn
        1025                1030                1035

Val Val Ala Asn Val Asn Gly Gln Ile Arg Pro Met Arg Val Arg
        1040                1045                1050

Asp Arg Ser Val Glu Ser Val Thr Ala Thr Ala Glu Lys Ala Asp
        1055                1060                1065

Ser Ser Asn Lys Gly His Val Ala Ala Pro Phe Ala Gly Val Val
        1070                1075                1080

Thr Val Thr Val Ala Glu Gly Asp Glu Val Lys Ala Gly Asp Ala
        1085                1090                1095

Val Ala Ile Ile Glu Ala Met Lys Met Glu Ala Thr Ile Thr Ala
        1100                1105                1110

Ser Val Asp Gly Lys Ile Asp Arg Val Val Val Pro Ala Ala Thr
        1115                1120                1125

Lys Val Glu Gly Gly Asp Leu Ile Val Val Ser
        1130                1135                1140

<210> SEQ ID NO 8
<211> LENGTH: 1140
<212> TYPE: PRT
<213> ORGANISM: artificial sequence
<220> FEATURE:
<223> OTHER INFORMATION: mutant protein

<400> SEQUENCE: 8

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
                20                  25                  30

Glu Thr Gly Ala Ala Thr Val Ala Ile Tyr Pro Arg Glu Asp Arg Gly
            35                  40                  45

Ser Phe Asn Arg Ser Phe Ala Ser Glu Ala Val Arg Ile Gly Thr Glu
```

```
                    50                  55                  60
Gly Ser Pro Val Lys Ala Tyr Leu Asp Ile Asp Glu Ile Ile Gly Ala
 65                  70                  75                  80

Ala Lys Lys Val Lys Ala Asp Ala Ile Tyr Pro Gly Tyr Gly Phe Leu
                     85                  90                  95

Ser Glu Asn Ala Gln Leu Ala Arg Glu Cys Ala Glu Asn Gly Ile Thr
                    100                 105                 110

Phe Ile Gly Pro Thr Pro Glu Val Leu Asp Leu Thr Gly Asp Lys Ser
                115                 120                 125

Arg Ala Val Thr Ala Ala Lys Lys Ala Gly Leu Pro Val Leu Ala Glu
            130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
            195                 200                 205

Val Glu Arg Ala Val Ile Asn Pro Gln His Ile Glu Val Gln Ile Leu
            210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
            275                 280                 285

Asp Glu Lys Gly Asn His Val Phe Ile Glu Met Asn Pro Arg Ile Gln
            290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
            355                 360                 365

Thr Ala Tyr Arg Ser Pro Gly Gly Ala Gly Val Arg Leu Asp Gly Ala
            370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
                435                 440                 445

Ile Ala Thr Gly Phe Ile Ala Asp His Pro His Leu Leu Gln Ala Pro
            450                 455                 460

Pro Ala Asp Asp Glu Gln Gly Arg Ile Leu Asp Tyr Leu Ala Asp Val
465                 470                 475                 480
```

```
Thr Val Asn Lys Pro His Gly Val Arg Pro Lys Asp Val Ala Ala Pro
            485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
            515                 520                 525

Arg Glu Gln Asp Ala Leu Ala Val Thr Asp Thr Thr Phe Arg Asp Ala
            530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
            565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
            595                 600                 605

Asn Ile Gln Met Leu Leu Arg Gly Arg Asn Thr Val Gly Tyr Thr Pro
            610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
            645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
            690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
            725                 730                 735

Leu Pro Val His Val His Thr His Asp Thr Ala Gly Gly Gln Leu Ala
            740                 745                 750

Thr Tyr Phe Ala Ala Ala Gln Ala Gly Ala Asp Ala Val Asp Gly Ala
            755                 760                 765

Ser Ala Pro Leu Ser Gly Thr Thr Ser Gln Pro Ser Leu Ser Ala Ile
            770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
            805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
            850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
            885                 890                 895
```

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
        930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Pro Ala Ala Thr
    1115                1120                1125

Lys Val Glu Gly Gly Asp Leu Ile Val Val Val Ser
    1130                1135                1140

<210> SEQ ID NO 9
<211> LENGTH: 1140
<212> TYPE: PRT
<213> ORGANISM: artificial sequence
<220> FEATURE:
<223> OTHER INFORMATION: mutant protein

<400> SEQUENCE: 9

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
            115                 120                 125

Arg Ala Val Thr Ala Ala Lys Lys Ala Gly Leu Pro Val Leu Ala Glu
130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
            195                 200                 205

Val Glu Arg Ala Val Ile Asn Pro Gln His Ile Glu Val Gln Ile Leu
210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
            275                 280                 285

Asp Glu Lys Gly Asn His Val Phe Ile Glu Met Asn Pro Arg Ile Gln
            290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
            355                 360                 365

Thr Ala Tyr Arg Ser Pro Gly Gly Ala Gly Val Arg Leu Asp Gly Ala
370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
            435                 440                 445

Ile Ala Thr Gly Glu Ile Ala Asp His Pro His Leu Leu Gln Ala Pro
450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
            515                 520                 525

Arg Glu Gln Asp Ala Leu Ala Val Thr Asp Thr Thr Phe Arg Asp Ala

```
            530                 535                 540
His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
                580                 585                 590

Asp Pro Trp Asp Arg Leu Asp Glu Leu Arg Glu Ala Met Pro Asn Val
                595                 600                 605

Asn Ile Gln Met Leu Leu Arg Gly Arg Asn Thr Val Gly Tyr Thr Pro
                610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
                675                 680                 685

Leu Tyr Thr Leu Asp Tyr Tyr Leu Lys Met Ala Glu Glu Ile Val Lys
                690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
                740                 745                 750

Thr Tyr Phe Ala Ala Ala Gln Ala Gly Ala Asp Ala Val Asp Gly Ala
                755                 760                 765

Ser Ala Pro Leu Ser Gly Thr Thr Ser Gln Pro Ser Leu Ser Ala Ile
                770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Pro Thr Gly Arg Val Tyr Arg
                820                 825                 830

His Glu Ile Pro Gly Gly Gln Leu Ser Asn Leu Arg Ala Gln Ala Thr
                835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
                915                 920                 925

Pro Glu Pro Leu Arg Thr Arg Ala Leu Glu Gly Arg Ser Glu Gly Lys
                930                 935                 940

Ala Pro Leu Thr Glu Val Pro Glu Glu Glu Gln Ala His Leu Asp Ala
945                 950                 955                 960
```

```
Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe  Phe Tyr Gly Leu Val  Glu Gly Arg
        995                 1000                1005

Glu Thr  Leu Ile Arg Leu Pro  Asp Val Arg Thr Pro  Leu Leu Val
    1010                1015                1020

Arg Leu  Asp Ala Ile Ser Glu  Pro Asp Asp Lys Gly  Met Arg Asn
    1025                1030                1035

Val Val  Ala Asn Val Asn Gly  Gln Ile Arg Pro Met  Arg Val Arg
    1040                1045                1050

Asp Arg  Ser Val Glu Ser Val  Thr Ala Thr Ala Glu  Lys Ala Asp
    1055                1060                1065

Ser Ser  Asn Lys Gly His Val  Ala Ala Pro Phe Ala  Gly Val Val
    1070                1075                1080

Thr Val  Thr Val Ala Glu Gly  Asp Glu Val Lys Ala  Gly Asp Ala
    1085                1090                1095

Val Ala  Ile Ile Glu Ala Met  Lys Met Glu Ala Thr  Ile Thr Ala
    1100                1105                1110

Ser Val  Asp Gly Lys Ile Asp  Arg Val Val Val Pro  Ala Ala Thr
    1115                1120                1125

Lys Val  Glu Gly Gly Asp Leu  Ile Val Val Val Ser
    1130                1135                1140

<210> SEQ ID NO 10
<211> LENGTH: 1140
<212> TYPE: PRT
<213> ORGANISM: artificial sequence
<220> FEATURE:
<223> OTHER INFORMATION: mutant protein

<400> SEQUENCE: 10

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175
```

```
Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590
```

```
Asp Pro Trp Asp Arg Leu Asp Glu Leu Arg Glu Ala Met Pro Asn Val
            595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
                675                 680                 685

Leu Tyr Thr Leu Asp Tyr Tyr Leu Lys Met Ala Glu Glu Ile Val Lys
            690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
                740                 745                 750

Thr Tyr Phe Ala Ala Ala Gln Ala Gly Asp Asp Ala Val Asp Gly Ala
            755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Glu Thr Gly Arg Val Tyr Arg
                820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Phe Gly Asn Thr
                980                 985                 990

Ser Ala Leu Asp Asp Arg Glu Phe Phe Tyr Gly Leu Val Glu Gly Arg
            995                 1000                1005

Glu Thr Leu Ile Arg Leu Pro Asp Val Arg Thr Pro Leu Leu Val
```

```
             1010                1015                1020

Arg Leu Asp Ala Ile Ser Glu Pro Asp Lys Gly Met Arg Asn
        1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
    1130                1135                1140

<210> SEQ ID NO 11
<211> LENGTH: 1140
<212> TYPE: PRT
<213> ORGANISM: artificial sequence
<220> FEATURE:
<223> OTHER INFORMATION: mutant protein

<400> SEQUENCE: 11

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
```

```
        225                 230                 235                 240
Leu Gln Arg Arg His Gln Lys Val Val Glu Ile Ala Pro Ala Gln His
                245                 250                 255
Leu Asp Pro Glu Leu Arg Asp Arg Ile Cys Ala Asp Ala Val Lys Phe
                260                 265                 270
Cys Arg Ser Ile Gly Tyr Gln Gly Ala Gly Thr Val Glu Phe Leu Val
                275                 280                 285
Asp Glu Lys Gly Asn His Val Phe Ile Glu Met Asn Pro Arg Ile Gln
                290                 295                 300
Val Glu His Thr Val Thr Glu Val Thr Glu Val Asp Leu Val Lys
305                 310                 315                 320
Ala Gln Met Arg Leu Ala Ala Gly Ala Thr Leu Lys Glu Leu Gly Leu
                325                 330                 335
Thr Gln Asp Lys Ile Lys Thr His Gly Ala Ala Leu Gln Cys Arg Ile
                340                 345                 350
Thr Thr Glu Asp Pro Asn Asn Gly Phe Arg Pro Asp Thr Gly Thr Ile
                355                 360                 365
Thr Ala Tyr Arg Ser Pro Gly Gly Ala Gly Val Arg Leu Asp Gly Ala
                370                 375                 380
Ala Gln Leu Gly Gly Glu Ile Thr Ala His Phe Asp Ser Met Leu Val
385                 390                 395                 400
Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
                420                 425                 430
Gly Phe Leu Arg Ala Leu Leu Arg Glu Glu Asp Phe Thr Ser Lys Arg
                435                 440                 445
Ile Ala Thr Gly Phe Ile Ala Asp His Pro His Leu Leu Gln Ala Pro
                450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
                500                 505                 510
Arg Asp Arg Leu Lys Gln Leu Gly Pro Ala Ala Phe Ala Arg Asp Leu
                515                 520                 525
Arg Glu Gln Asp Ala Leu Ala Val Thr Asp Thr Thr Phe Arg Asp Ala
                530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
                580                 585                 590
Asp Pro Trp Asp Arg Leu Asp Glu Leu Arg Glu Ala Met Pro Asn Val
                595                 600                 605
Asn Ile Gln Met Leu Leu Arg Gly Arg Asn Thr Val Gly Tyr Thr Pro
                610                 615                 620
Tyr Pro Asp Ser Val Cys Arg Ala Phe Val Lys Glu Ala Ala Ser Ser
625                 630                 635                 640
Gly Val Asp Ile Phe Arg Ile Phe Asp Ala Leu Asn Asp Val Ser Gln
                645                 650                 655
```

```
Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
            690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gln Leu Ala
            740                 745                 750

Thr Tyr Phe Ala Ala Ala Gln Ala Gly Asp Asp Ala Val Asp Gly Ala
            755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Val Gly Pro Thr Gly Arg Val Tyr Arg
                820                 825                 830

His Glu Ile Pro Gly Gly Gln Leu Ser Asn Leu Arg Ala Gln Ala Thr
                835                 840                 845

Ala Leu Gly Leu Ala Asp Arg Phe Glu Leu Ile Glu Asp Asn Tyr Ala
            850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
            930                 935                 940

Ala Pro Leu Thr Glu Val Pro Glu Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Phe Gly Asn Thr
            980                 985                 990

Ser Ala Leu Asp Asp Arg Glu Phe Phe Tyr Gly Leu Val Glu Gly Arg
            995                 1000                1005

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065
```

```
Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Pro Ala Ala Thr
    1115                1120                1125

Lys Val Glu Gly Gly Asp Leu Ile Val Val Val Ser
    1130                1135                1140

<210> SEQ ID NO 12
<211> LENGTH: 1140
<212> TYPE: PRT
<213> ORGANISM: artificial sequence
<220> FEATURE:
<223> OTHER INFORMATION: mutant protein

<400> SEQUENCE: 12

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
                20                  25                  30

Glu Thr Gly Ala Ala Thr Val Ala Ile Tyr Pro Arg Glu Asp Arg Gly
            35                  40                  45

Ser Phe His Arg Ser Phe Ala Ser Glu Ala Val Arg Ile Gly Thr Glu
        50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285
```

```
Asp Glu Lys Gly Asn His Val Phe Ile Glu Met Asn Pro Arg Ile Gln
290                 295                 300

Val Glu His Thr Val Thr Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
                340                 345                 350

Thr Thr Glu Asp Pro Asn Asn Gly Phe Arg Pro Asp Thr Gly Thr Ile
                355                 360                 365

Thr Ala Tyr Arg Ser Pro Gly Gly Ala Gly Val Arg Leu Asp Gly Ala
370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
                435                 440                 445

Ile Ala Thr Gly Phe Ile Ala Asp His Pro His Leu Leu Gln Ala Pro
                450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
                500                 505                 510

Arg Asp Arg Leu Lys Gln Leu Gly Pro Ala Ala Phe Ala Arg Asp Leu
                515                 520                 525

Arg Glu Gln Asp Ala Leu Ala Val Thr Asp Thr Thr Phe Arg Asp Ala
                530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
                580                 585                 590

Asp Pro Trp Asp Arg Leu Asp Glu Leu Arg Glu Ala Met Pro Asn Val
                595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
                675                 680                 685

Leu Tyr Thr Leu Asp Tyr Tyr Leu Lys Met Ala Glu Glu Ile Val Lys
                690                 695                 700

Ser Gly Ala His Ile Leu Ala Ile Lys Asp Met Ala Gly Leu Leu Arg
```

```
                705                 710                 715                 720
            Pro Ala Ala Val Thr Lys Leu Val Thr Ala Leu Arg Arg Glu Phe Asp
                            725                 730                 735
            Leu Pro Val His Val His Thr His Asp Thr Ala Gly Gly Gln Leu Ala
                            740                 745                 750
            Thr Tyr Phe Ala Ala Gln Ala Gly Ala Asp Ala Val Asp Gly Ala
                            755                 760                 765
            Ser Ala Pro Leu Ser Gly Thr Thr Ser Gln Pro Ser Leu Ser Ala Ile
                770                 775                 780
            Val Ala Ala Phe Ala His Thr Arg Arg Asp Thr Gly Leu Ser Leu Glu
            785                 790                 795                 800
            Ala Val Ser Asp Leu Glu Pro Tyr Trp Glu Ala Val Arg Gly Leu Tyr
                            805                 810                 815
            Leu Pro Phe Glu Ser Gly Thr Val Gly Glu Thr Gly Arg Val Tyr Arg
                            820                 825                 830
            His Glu Ile Pro Gly Gly Gln Leu Ser Asn Leu Arg Ala Gln Ala Thr
                            835                 840                 845
            Ala Leu Gly Leu Ala Asp Arg Phe Glu Leu Ile Glu Asp Asn Tyr Ala
            850                 855                 860
            Ala Val Asn Glu Met Leu Gly Arg Pro Thr Lys Val Thr Pro Ser Ser
            865                 870                 875                 880
            Lys Val Val Gly Asp Leu Ala Leu His Leu Val Gly Ala Gly Val Asp
                            885                 890                 895
            Pro Ala Asp Phe Ala Ala Asp Pro Gln Lys Tyr Asp Ile Pro Asp Ser
                            900                 905                 910
            Val Ile Ala Phe Leu Arg Gly Glu Leu Gly Asn Pro Pro Gly Gly Trp
                            915                 920                 925
            Pro Glu Pro Leu Arg Thr Arg Ala Leu Glu Gly Arg Ser Glu Gly Lys
                            930                 935                 940
            Ala Pro Leu Thr Glu Val Pro Glu Glu Glu Gln Ala His Leu Asp Ala
            945                 950                 955                 960
            Asp Asp Ser Lys Glu Arg Arg Asn Ser Leu Asn Arg Leu Leu Phe Pro
                            965                 970                 975
            Lys Pro Thr Glu Glu Phe Leu Glu His Arg Arg Arg Phe Gly Asn Thr
                            980                 985                 990
            Ser Ala Leu Asp Asp Arg Glu Phe  Phe Tyr Gly Leu Val  Glu Gly Arg
                            995                 1000                1005
            Glu Thr  Leu Ile Arg Leu Pro  Asp Val Arg Thr Pro  Leu Leu Val
                1010                1015                1020
            Arg Leu  Asp Ala Ile Ser Glu  Pro Asp Lys Gly  Met Arg Asn
                1025                1030                1035
            Val Val  Ala Asn Val Asn Gly  Gln Ile Arg Pro Met  Arg Val Arg
                1040                1045                1050
            Asp Arg  Ser Val Glu Ser Val  Thr Ala Thr Ala Glu  Lys Ala Asp
                1055                1060                1065
            Ser Ser  Asn Lys Gly His Val  Ala Ala Pro Phe Ala  Gly Val Val
                1070                1075                1080
            Thr Val  Thr Val Ala Glu Gly  Asp Glu Val Lys Ala  Gly Asp Ala
                1085                1090                1095
            Val Ala  Ile Ile Glu Ala Met  Lys Met Glu Ala Thr  Ile Thr Ala
                1100                1105                1110
            Ser Val  Asp Gly Lys Ile Asp  Arg Val Val Val Pro  Ala Ala Thr
                1115                1120                1125
```

Lys Val Glu Gly Gly Asp Leu Ile Val Val Val Ser
    1130            1135            1140

<210> SEQ ID NO 13
<211> LENGTH: 1140
<212> TYPE: PRT
<213> ORGANISM: artificial sequence
<220> FEATURE:
<223> OTHER INFORMATION: mutant protein

<400> SEQUENCE: 13

Met Ser Thr His Thr Ser Thr Leu Pro Ala Phe Lys Lys Ile Leu
1               5                   10                  15

Val Ala Asn Arg Gly Glu Ile Ala Val Arg Ala Phe Arg Ala Ala Leu
                20                  25                  30

Glu Thr Gly Ala Ala Thr Val Ala Ile Tyr Pro Arg Glu Asp Arg Gly
            35                  40                  45

Ser Phe His Arg Ser Phe Ala Ser Glu Ala Val Arg Ile Gly Thr Glu
            50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
            115                 120                 125

Arg Ala Val Thr Ala Ala Lys Lys Ala Gly Leu Pro Val Leu Ala Glu
            130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
            195                 200                 205

Val Glu Arg Ala Val Ile Asn Pro Gln His Ile Glu Val Gln Ile Leu
            210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
            275                 280                 285

Asp Glu Lys Gly Asn His Val Phe Ile Glu Met Asn Pro Arg Ile Gln
            290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

-continued

```
Thr Thr Glu Asp Pro Asn Asn Gly Phe Arg Pro Asp Thr Gly Thr Ile
        355                 360                 365
Thr Ala Tyr Arg Ser Pro Gly Ala Gly Val Arg Leu Asp Gly Ala
    370                 375                 380
Ala Gln Leu Gly Gly Glu Ile Thr Ala His Phe Asp Ser Met Leu Val
385                 390                 395                 400
Lys Met Thr Cys Arg Gly Ser Asp Phe Glu Thr Ala Val Ala Arg Ala
                405                 410                 415
Gln Arg Ala Leu Ala Glu Phe Thr Val Ser Gly Val Ala Thr Asn Ile
            420                 425                 430
Gly Phe Leu Arg Ala Leu Leu Arg Glu Glu Asp Phe Thr Ser Lys Arg
                435                 440                 445
Ile Ala Thr Gly Phe Ile Ala Asp His Pro His Leu Leu Gln Ala Pro
        450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
                485                 490                 495
Ile Asp Lys Leu Pro Asn Ile Lys Asp Leu Pro Leu Pro Arg Gly Ser
            500                 505                 510
Arg Asp Arg Leu Lys Gln Leu Gly Pro Ala Ala Phe Ala Arg Asp Leu
                515                 520                 525
Arg Glu Gln Asp Ala Leu Ala Val Thr Asp Thr Thr Phe Arg Asp Ala
        530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
                565                 570                 575
Ala Trp Gly Gly Ala Thr Tyr Asp Val Ala Met Arg Phe Leu Phe Glu
            580                 585                 590
Asp Pro Trp Asp Arg Leu Asp Glu Leu Arg Glu Ala Met Pro Asn Val
                595                 600                 605
Asn Ile Gln Met Leu Leu Arg Gly Arg Asn Thr Val Gly Tyr Thr Pro
        610                 615                 620
Tyr Pro Asp Ser Val Cys Arg Ala Phe Val Lys Glu Ala Ala Ser Ser
625                 630                 635                 640
Gly Val Asp Ile Phe Arg Ile Phe Asp Ala Leu Asn Asp Val Ser Gln
                645                 650                 655
Met Arg Pro Ala Ile Asp Ala Val Leu Glu Thr Asn Thr Ala Val Ala
            660                 665                 670
Glu Val Ala Met Ala Tyr Ser Gly Asp Leu Ser Asp Pro Asn Glu Lys
                675                 680                 685
Leu Tyr Thr Leu Asp Tyr Tyr Leu Lys Met Ala Glu Glu Ile Val Lys
        690                 695                 700
Ser Gly Ala His Ile Leu Ala Ile Lys Asp Met Ala Gly Leu Leu Arg
705                 710                 715                 720
Pro Ala Ala Val Thr Lys Leu Val Thr Ala Leu Arg Arg Glu Phe Asp
                725                 730                 735
Leu Pro Val His Val His Thr His Asp Thr Ala Gly Gly Gln Leu Ala
            740                 745                 750
Thr Tyr Phe Ala Ala Ala Gln Ala Gly Ala Asp Ala Val Asp Gly Ala
        755                 760                 765
```

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Val Gly Pro Thr Gly Arg Val Tyr Arg
                820                 825                 830

His Glu Ile Pro Gly Gly Gln Leu Ser Asn Leu Arg Ala Gln Ala Thr
                835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
                915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
                980                 985                 990

Ser Ala Leu Asp Asp Arg Glu Phe Phe Tyr Gly Leu Val Glu Gly Arg
                995                 1000                1005

Glu Thr Leu Ile Arg Leu Pro Asp Val Arg Thr Pro Leu Leu Val
    1010            1015            1020

Arg Leu Asp Ala Ile Ser Glu Glu Asp Asp Lys Gly Met Arg Asn
    1025            1030            1035

Val Val Ala Asn Val Asn Gly Gln Ile Arg Pro Met Arg Val Arg
    1040            1045            1050

Asp Arg Ser Val Glu Ser Val Thr Ala Thr Ala Glu Lys Ala Asp
    1055            1060            1065

Ser Ser Asn Lys Gly His Val Ala Ala Pro Phe Ala Gly Val Val
    1070            1075            1080

Thr Val Thr Val Ala Glu Gly Asp Glu Val Lys Ala Gly Asp Ala
    1085            1090            1095

Val Ala Ile Ile Glu Ala Met Lys Met Glu Ala Thr Ile Thr Ala
    1100            1105            1110

Ser Val Asp Gly Lys Ile Asp Arg Val Val Val Pro Ala Ala Thr
    1115            1120            1125

Lys Val Glu Gly Gly Asp Leu Ile Val Val Val Ser
    1130            1135            1140

<210> SEQ ID NO 14
<211> LENGTH: 1140
<212> TYPE: PRT
<213> ORGANISM: artificial sequence
<220> FEATURE:
<223> OTHER INFORMATION: mutant protein

<400> SEQUENCE: 14

```
Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
```

```
            405                 410                 415
Gln Arg Ala Leu Ala Glu Phe Thr Val Ser Gly Val Ala Thr Asn Ile
            420                 425                 430
Gly Phe Leu Arg Ala Leu Leu Arg Glu Glu Asp Phe Thr Ser Lys Arg
            435                 440                 445
Ile Ala Thr Gly Phe Ile Ala Asp His Pro His Leu Leu Gln Ala Pro
            450                 455                 460
Pro Ala Asp Asp Glu Gln Gly Arg Ile Leu Asp Tyr Leu Ala Asp Val
465                 470                 475                 480
Thr Val Asn Lys Pro His Gly Val Arg Pro Lys Asp Val Ala Ala Pro
            485                 490                 495
Ile Asp Lys Leu Pro Asn Ile Lys Asp Leu Pro Leu Pro Arg Gly Ser
            500                 505                 510
Arg Asp Arg Leu Lys Gln Leu Gly Pro Ala Ala Phe Ala Arg Asp Leu
            515                 520                 525
Arg Glu Gln Asp Ala Leu Ala Val Thr Asp Thr Thr Phe Arg Asp Ala
            530                 535                 540
His Gln Ser Leu Leu Ala Thr Arg Val Arg Ser Phe Ala Leu Lys Pro
545                 550                 555                 560
Ala Ala Glu Ala Val Ala Lys Leu Thr Pro Glu Leu Leu Ser Val Glu
            565                 570                 575
Ala Trp Gly Gly Ala Thr Tyr Asp Val Ala Met Arg Phe Leu Phe Glu
            580                 585                 590
Asp Pro Trp Asp Arg Leu Asp Glu Leu Arg Glu Ala Met Pro Asn Val
            595                 600                 605
Asn Ile Gln Met Leu Leu Arg Gly Arg Asn Thr Val Gly Tyr Thr Pro
            610                 615                 620
Tyr Pro Asp Ser Val Cys Arg Ala Phe Val Lys Glu Ala Ala Ser Ser
625                 630                 635                 640
Gly Val Asp Ile Phe Arg Ile Phe Asp Ala Leu Asn Asp Val Ser Gln
            645                 650                 655
Met Arg Pro Ala Ile Asp Ala Val Leu Glu Thr Asn Thr Ala Val Ala
            660                 665                 670
Glu Val Ala Met Ala Tyr Ser Gly Asp Leu Ser Asp Pro Asn Glu Lys
            675                 680                 685
Leu Tyr Thr Leu Asp Tyr Tyr Leu Lys Met Ala Glu Glu Ile Val Lys
            690                 695                 700
Ser Gly Ala His Ile Leu Ala Ile Lys Asp Met Ala Gly Leu Leu Arg
705                 710                 715                 720
Pro Ala Ala Val Thr Lys Leu Val Thr Ala Leu Arg Arg Glu Phe Asp
            725                 730                 735
Leu Pro Val His Val His Thr His Asp Thr Ala Gly Gly Gln Leu Ala
            740                 745                 750
Thr Tyr Phe Ala Ala Ala Gln Ala Gly Asp Asp Ala Val Asp Gly Ala
            755                 760                 765
Ser Ala Pro Leu Ser Gly Thr Thr Ser Gln Pro Ser Leu Ser Ala Ile
            770                 775                 780
Val Ala Ala Phe Ala His Thr Arg Arg Asp Thr Gly Leu Ser Leu Glu
785                 790                 795                 800
Ala Val Ser Asp Leu Glu Pro Tyr Trp Glu Ala Val Arg Gly Leu Tyr
            805                 810                 815
Leu Pro Phe Glu Ser Gly Thr Pro Gly Glu Thr Gly Arg Val Tyr Arg
            820                 825                 830
```

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu His Arg Arg Phe Gly Asn Thr
            980                 985                 990

Ser Ala Leu Asp Asp Arg Glu Phe Phe Tyr Gly Leu Val Glu Gly Arg
            995                 1000                1005

Glu Thr Leu Ile Arg Leu Pro Asp Val Arg Thr Pro Leu Leu Val
    1010                1015                1020

Arg Leu Asp Ala Ile Ser Glu Glu Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
    1130                1135                1140

<210> SEQ ID NO 15
<211> LENGTH: 1140
<212> TYPE: PRT
<213> ORGANISM: artificial sequence
<220> FEATURE:
<223> OTHER INFORMATION: mutant protein

<400> SEQUENCE: 15

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

```
Ser Phe His Arg Ser Phe Ala Ser Glu Ala Val Arg Ile Gly Thr Glu
     50                  55                  60

Gly Ser Pro Val Lys Ala Tyr Leu Asp Ile Asp Glu Ile Ile Gly Ala
 65                  70                  75                  80

Ala Lys Lys Val Lys Ala Asp Ala Ile Tyr Pro Gly Tyr Gly Phe Leu
                     85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
            115                 120                 125

Arg Ala Val Thr Ala Ala Lys Lys Ala Gly Leu Pro Val Leu Ala Glu
        130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                    165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
            195                 200                 205

Val Glu Arg Ala Val Ile Asn Pro Gln His Ile Glu Val Gln Ile Leu
        210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                    245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
            275                 280                 285

Asp Glu Lys Gly Asn His Val Phe Ile Glu Met Asn Pro Arg Ile Gln
        290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                    325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
            355                 360                 365

Thr Ala Tyr Arg Ser Pro Gly Gly Ala Gly Val Arg Leu Asp Gly Ala
        370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                    405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
        450                 455                 460
```

```
Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
            485                 490                 495

Ile Asp Lys Leu Pro Asn Ile Lys Asp Leu Pro Leu Pro Arg Gly Ser
        500                 505                 510

Arg Asp Arg Leu Lys Gln Leu Gly Pro Ala Ala Phe Ala Arg Asp Leu
    515                 520                 525

Arg Glu Gln Asp Ala Leu Ala Val Thr Asp Thr Thr Phe Arg Asp Ala
        530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
            565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
            645                 650                 655

Met Arg Pro Ala Ile Asp Ala Val Leu Glu Thr Asn Thr Ala Val Ala
        660                 665                 670

Glu Val Ala Met Ala Tyr Ser Gly Asp Leu Ser Asp Pro Asn Glu Lys
    675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
            725                 730                 735

Leu Pro Val His Val His Thr His Asp Thr Ala Gly Gly Gln Leu Ala
            740                 745                 750

Thr Tyr Phe Ala Ala Ala Gln Ala Gly Asp Asp Ala Val Asp Gly Ala
        755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
            805                 810                 815

Leu Pro Phe Glu Ser Gly Thr Pro Gly Pro Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
        850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
```

```
                         885                 890                 895
Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
                915                 920                 925

Pro Glu Pro Leu Arg Thr Arg Ala Leu Glu Gly Arg Ser Glu Gly Lys
                930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
                980                 985                 990

Ser Ala Leu Asp Asp Arg Glu Phe Phe Tyr Gly Leu Val Glu Gly Arg
                995                1000                1005

Glu Thr Leu Ile Arg Leu Pro Asp Val Arg Thr Pro Leu Leu Val
                1010                1015                1020

Arg Leu Asp Ala Ile Ser Glu Glu Asp Asp Lys Gly Met Arg Asn
                1025                1030                1035

Val Val Ala Asn Val Asn Gly Gln Ile Arg Pro Met Arg Val Arg
                1040                1045                1050

Asp Arg Ser Val Glu Ser Val Thr Ala Thr Ala Glu Lys Ala Asp
                1055                1060                1065

Ser Ser Asn Lys Gly His Val Ala Ala Pro Phe Ala Gly Val Val
                1070                1075                1080

Thr Val Thr Val Ala Glu Gly Asp Glu Val Lys Ala Gly Asp Ala
                1085                1090                1095

Val Ala Ile Ile Glu Ala Met Lys Met Glu Ala Thr Ile Thr Ala
                1100                1105                1110

Ser Val Asp Gly Lys Ile Asp Arg Val Val Val Pro Ala Ala Thr
                1115                1120                1125

Lys Val Glu Gly Gly Asp Leu Ile Val Val Ser
                1130                1135                1140

<210> SEQ ID NO 16
<211> LENGTH: 1140
<212> TYPE: PRT
<213> ORGANISM: artificial sequence
<220> FEATURE:
<223> OTHER INFORMATION: mutant protein

<400> SEQUENCE: 16

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
                20                  25                  30

Glu Thr Gly Ala Ala Thr Val Ala Ile Tyr Pro Arg Glu Asp Arg Gly
            35                  40                  45

Ser Phe His Arg Ser Phe Ala Ser Glu Ala Val Arg Ile Gly Thr Glu
        50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
```

```
            100                 105                   110
Phe Ile Gly Pro Thr Pro Glu Val Leu Asp Leu Thr Gly Asp Lys Ser
            115                 120                 125

Arg Ala Val Thr Ala Ala Lys Lys Ala Gly Leu Pro Val Leu Ala Glu
            130                 135             140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
            195                 200                 205

Val Glu Arg Ala Val Ile Asn Pro Gln His Ile Glu Val Gln Ile Leu
            210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
            275                 280                 285

Asp Glu Lys Gly Asn His Val Phe Ile Glu Met Asn Pro Arg Ile Gln
            290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
                340                 345                 350

Thr Thr Glu Asp Pro Asn Asn Gly Phe Arg Pro Asp Thr Gly Thr Ile
                355                 360                 365

Thr Ala Tyr Arg Ser Pro Gly Gly Ala Gly Val Arg Leu Asp Gly Ala
            370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
            450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
            515                 520                 525
```

```
Arg Glu Gln Asp Ala Leu Ala Val Thr Asp Thr Thr Phe Arg Asp Ala
530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
            675                 680                 685

Leu Tyr Thr Leu Asp Tyr Tyr Leu Lys Met Ala Glu Glu Ile Val Lys
        690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
                740                 745                 750

Thr Tyr Phe Ala Ala Gln Ala Gly Ala Asp Ala Val Asp Gly Ala
            755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Pro Gly Glu Thr Gly Arg Val Tyr Arg
                820                 825                 830

His Glu Ile Pro Gly Gly Gln Leu Ser Asn Leu Arg Ala Gln Ala Thr
            835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
                900                 905                 910

Val Ile Ala Phe Leu Arg Gly Glu Leu Gly Asn Pro Pro Gly Gly Trp
            915                 920                 925

Pro Glu Pro Leu Arg Thr Arg Ala Leu Glu Gly Arg Ser Glu Gly Lys
930                 935                 940
```

```
Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
            965                 970                 975

Lys Pro Thr Glu Glu Phe Leu Glu His Arg Arg Arg Phe Gly Asn Thr
                980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val
    1010                1015                1020

Arg Leu Asp Ala Ile Ser Glu Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Ser
    1130                1135                1140
```

<210> SEQ ID NO 17
<211> LENGTH: 1140
<212> TYPE: PRT
<213> ORGANISM: artificial sequence
<220> FEATURE:
<223> OTHER INFORMATION: mutant protein

<400> SEQUENCE: 17

```
Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160
```

```
Gln Thr Tyr Pro Ile Phe Val Lys Ala Val Ala Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
            195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
            245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
            275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
            325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
            355                 360                 365

Thr Ala Tyr Arg Ser Pro Gly Gly Ala Gly Val Arg Leu Asp Gly Ala
            370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
            405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
            485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
            515                 520                 525

Arg Glu Gln Asp Ala Leu Ala Val Thr Asp Thr Thr Phe Arg Asp Ala
            530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
            565                 570                 575

Ala Trp Gly Gly Ala Thr Tyr Asp Val Ala Met Arg Phe Leu Phe Glu
```

-continued

```
                580                 585                 590
Asp Pro Trp Asp Arg Leu Asp Glu Leu Arg Glu Ala Met Pro Asn Val
            595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Asp Asp Ala Val Asp Gly Ala
        755                 760                 765

Ser Ala Pro Leu Ser Gly Thr Thr Ser Gln Pro Ser Leu Ser Ala Ile
    770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Val Gly Glu Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
    850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Phe Gly Asn Thr
            980                 985                 990

Ser Ala Leu Asp Asp Arg Glu Phe  Phe Tyr Gly Leu Val  Glu Gly Arg
        995                 1000                1005
```

-continued

Glu Thr Leu Ile Arg Leu Pro Asp Val Arg Thr Pro Leu Leu Val
    1010                1015                1020

Arg Leu Asp Ala Ile Ser Glu Pro Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
    1130                1135                1140

<210> SEQ ID NO 18
<211> LENGTH: 1140
<212> TYPE: PRT
<213> ORGANISM: artificial sequence
<220> FEATURE:
<223> OTHER INFORMATION: mutant protein

<400> SEQUENCE: 18

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

-continued

```
Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
            245                 250                 255

Leu Asp Pro Glu Leu Arg Asp Arg Ile Cys Ala Asp Ala Val Lys Phe
        260                 265                 270

Cys Arg Ser Ile Gly Tyr Gln Gly Ala Gly Thr Val Glu Phe Leu Val
    275                 280                 285

Asp Glu Lys Gly Asn His Val Phe Ile Glu Met Asn Pro Arg Ile Gln
290                 295                 300

Val Glu His Thr Val Thr Glu Glu Val Thr Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
            340                 345                 350

Thr Thr Glu Asp Pro Asn Asn Gly Phe Arg Pro Asp Thr Gly Thr Ile
        355                 360                 365

Thr Ala Tyr Arg Ser Pro Gly Gly Ala Gly Val Arg Leu Asp Gly Ala
    370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
            420                 425                 430

Gly Phe Leu Arg Ala Leu Leu Arg Glu Glu Asp Phe Thr Ser Lys Arg
        435                 440                 445

Ile Ala Thr Gly Phe Ile Ala Asp His Pro His Leu Leu Gln Ala Pro
    450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
            500                 505                 510

Arg Asp Arg Leu Lys Gln Leu Gly Pro Ala Ala Phe Ala Arg Asp Leu
        515                 520                 525

Arg Glu Gln Asp Ala Leu Ala Val Thr Asp Thr Thr Phe Arg Asp Ala
    530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
    610                 615                 620

Tyr Pro Asp Ser Val Cys Arg Ala Phe Val Lys Glu Ala Ala Ser Ser
625                 630                 635                 640
```

```
Gly Val Asp Ile Phe Arg Ile Phe Asp Ala Leu Asn Asp Val Ser Gln
                    645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
    690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Asp Asp Ala Val Asp Gly Ala
        755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Val Gly Pro Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                1000                1005

Glu Thr Leu Ile Arg Leu Pro Asp Val Arg Thr Pro Leu Leu Val
    1010                1015                1020

Arg Leu Asp Ala Ile Ser Glu Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
```

-continued

```
            1055                1060                1065

Ser Ser Asn Lys Gly His Val Ala Ala Pro Phe Ala Gly Val Val
        1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
1100                1105                1110

Ser Val Asp Gly Lys Ile Asp Arg Val Val Pro Ala Ala Thr
    1115                1120                1125

Lys Val Glu Gly Gly Asp Leu Ile Val Val Val Ser
    1130                1135                1140

<210> SEQ ID NO 19
<211> LENGTH: 1140
<212> TYPE: PRT
<213> ORGANISM: artificial sequence
<220> FEATURE:
<223> OTHER INFORMATION: mutant protein

<400> SEQUENCE: 19

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
    130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
```

```
                275                 280                 285
Asp Glu Lys Gly Asn His Val Phe Ile Glu Met Asn Pro Arg Ile Gln
290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335

Thr Gln Asp Lys Ile Lys Thr His Gly Ala Ala Leu Gln Cys Arg Ile
                340                 345                 350

Thr Thr Glu Asp Pro Asn Asn Gly Phe Arg Pro Asp Thr Gly Thr Ile
                355                 360                 365

Thr Ala Tyr Arg Ser Pro Gly Gly Ala Gly Val Arg Leu Asp Gly Ala
370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
                435                 440                 445

Ile Ala Thr Gly Phe Ile Ala Asp His Pro His Leu Leu Gln Ala Pro
450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
                500                 505                 510

Arg Asp Arg Leu Lys Gln Leu Gly Pro Ala Ala Phe Ala Arg Asp Leu
                515                 520                 525

Arg Glu Gln Asp Ala Leu Ala Val Thr Asp Thr Thr Phe Arg Asp Ala
530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
                580                 585                 590

Asp Pro Trp Asp Arg Leu Asp Glu Leu Arg Glu Ala Met Pro Asn Val
                595                 600                 605

Asn Ile Gln Met Leu Leu Arg Gly Arg Asn Thr Val Gly Tyr Thr Pro
                610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
                675                 680                 685

Leu Tyr Thr Leu Asp Tyr Tyr Leu Lys Met Ala Glu Glu Ile Val Lys
                690                 695                 700
```

```
Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
            725                 730                 735

Leu Pro Val His Val His Thr His Asp Thr Ala Gly Gln Leu Ala
        740                 745                 750

Thr Tyr Phe Ala Ala Ala Gln Ala Gly Ala Asp Ala Val Asp Gly Ala
            755                 760                 765

Ser Ala Pro Leu Ser Gly Thr Thr Ser Gln Pro Ser Leu Ser Ala Ile
770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Val Gly Glu Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
            995                 1000                1005

Glu Thr Leu Ile Arg Leu Pro Asp Val Arg Thr Pro Leu Leu Val
    1010                1015                1020

Arg Leu Asp Ala Ile Ser Glu Glu Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110
```

```
Ser Val Asp Gly Lys Ile Asp Arg Val Val Val Pro Ala Ala Thr
1115                1120                1125

Lys Val Glu Gly Gly Asp Leu Ile Val Val Val Ser
1130                1135                1140

<210> SEQ ID NO 20
<211> LENGTH: 1140
<212> TYPE: PRT
<213> ORGANISM: artificial sequence
<220> FEATURE:
<223> OTHER INFORMATION: mutant protein

<400> SEQUENCE: 20

Met Ser Thr His Thr Ser Ser Thr Leu Pro Ala Phe Lys Lys Ile Leu
1               5                   10                  15

Val Ala Asn Arg Gly Glu Ile Ala Val Arg Ala Phe Arg Ala Ala Leu
            20                  25                  30

Glu Thr Gly Ala Ala Thr Val Ala Ile Tyr Pro Arg Glu Asp Arg Gly
        35                  40                  45

Ser Phe His Arg Ser Phe Ala Ser Glu Ala Val Arg Ile Gly Thr Glu
    50                  55                  60

Gly Ser Pro Val Lys Ala Tyr Leu Asp Ile Asp Glu Ile Ile Gly Ala
65                  70                  75                  80

Ala Lys Lys Val Lys Ala Asp Ala Ile Tyr Pro Gly Tyr Gly Phe Leu
                85                  90                  95

Ser Glu Asn Ala Gln Leu Ala Arg Glu Cys Ala Glu Asn Gly Ile Thr
            100                 105                 110

Phe Ile Gly Pro Thr Pro Glu Val Leu Asp Leu Thr Gly Asp Lys Ser
        115                 120                 125

Arg Ala Val Thr Ala Ala Lys Lys Ala Gly Leu Pro Val Leu Ala Glu
130                 135                 140

Ser Thr Pro Ser Lys Asn Ile Asp Glu Ile Val Lys Ser Ala Glu Gly
145                 150                 155                 160

Gln Thr Tyr Pro Ile Phe Val Lys Ala Val Ala Gly Gly Gly Gly Arg
                165                 170                 175

Gly Met Arg Phe Val Ala Ser Pro Asp Glu Leu Arg Lys Leu Ala Thr
            180                 185                 190

Glu Ala Ser Arg Glu Ala Glu Ala Phe Gly Asp Gly Ala Val Tyr
        195                 200                 205

Val Glu Arg Ala Val Ile Asn Pro Gln His Ile Glu Val Gln Ile Leu
    210                 215                 220

Gly Asp His Thr Gly Glu Val Val His Leu Tyr Glu Arg Asp Cys Ser
225                 230                 235                 240

Leu Gln Arg Arg His Gln Lys Val Val Glu Ile Ala Pro Ala Gln His
                245                 250                 255

Leu Asp Pro Glu Leu Arg Asp Arg Ile Cys Ala Asp Ala Val Lys Phe
            260                 265                 270

Cys Arg Ser Ile Gly Tyr Gln Gly Ala Gly Thr Val Glu Phe Leu Val
        275                 280                 285

Asp Glu Lys Gly Asn His Val Phe Ile Glu Met Asn Pro Arg Ile Gln
    290                 295                 300

Val Glu His Thr Val Thr Glu Glu Val Thr Glu Val Asp Leu Val Lys
305                 310                 315                 320

Ala Gln Met Arg Leu Ala Ala Gly Ala Thr Leu Lys Glu Leu Gly Leu
                325                 330                 335
```

-continued

```
Thr Gln Asp Lys Ile Lys Thr His Gly Ala Ala Leu Gln Cys Arg Ile
                340                 345                 350

Thr Thr Glu Asp Pro Asn Asn Gly Phe Arg Pro Asp Thr Gly Thr Ile
            355                 360                 365

Thr Ala Tyr Arg Ser Pro Gly Gly Ala Gly Val Arg Leu Asp Gly Ala
        370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
            435                 440                 445

Ile Ala Thr Gly Phe Ile Ala Asp His Pro His Leu Leu Gln Ala Pro
        450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
                500                 505                 510

Arg Asp Arg Leu Lys Gln Leu Gly Pro Ala Ala Phe Ala Arg Asp Leu
            515                 520                 525

Arg Glu Gln Asp Ala Leu Ala Val Thr Asp Thr Thr Phe Arg Asp Ala
530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
            580                 585                 590

Asp Pro Trp Asp Arg Leu Asp Glu Leu Arg Glu Ala Met Pro Asn Val
        595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
            660                 665                 670

Glu Val Ala Met Ala Tyr Ser Gly Asp Leu Ser Asp Pro Asn Glu Lys
        675                 680                 685

Leu Tyr Thr Leu Asp Tyr Tyr Leu Lys Met Ala Glu Glu Ile Val Lys
690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
                725                 730                 735

Leu Pro Val His Val His Thr His Asp Thr Ala Gly Gly Gln Leu Ala
            740                 745                 750

Thr Tyr Phe Ala Ala Ala Gln Ala Gly Asp Asp Ala Val Asp Gly Ala
```

```
                755                 760                 765
Ser Ala Pro Leu Ser Gly Thr Thr Ser Gln Pro Ser Leu Ser Ala Ile
    770                 775                 780

Val Ala Ala Phe Ala His Thr Arg Arg Asp Thr Gly Leu Ser Leu Glu
785                 790                 795                 800

Ala Val Ser Asp Leu Glu Pro Tyr Trp Glu Ala Val Arg Gly Leu Tyr
                805                 810                 815

Leu Pro Phe Glu Ser Gly Thr Val Gly Glu Thr Gly Arg Val Tyr Arg
            820                 825                 830

His Glu Ile Pro Gly Gly Gln Leu Ser Asn Leu Arg Ala Gln Ala Thr
        835                 840                 845

Ala Leu Gly Leu Ala Asp Arg Phe Glu Leu Ile Glu Asp Asn Tyr Ala
850                 855                 860

Ala Val Asn Glu Met Leu Gly Arg Pro Thr Lys Val Thr Pro Ser Ser
865                 870                 875                 880

Lys Val Val Gly Asp Leu Ala Leu His Leu Val Gly Ala Gly Val Asp
                885                 890                 895

Pro Ala Asp Phe Ala Ala Asp Pro Gln Lys Tyr Asp Ile Pro Asp Ser
            900                 905                 910

Val Ile Ala Phe Leu Arg Gly Glu Leu Gly Asn Pro Pro Gly Gly Trp
        915                 920                 925

Pro Glu Pro Leu Arg Thr Arg Ala Leu Glu Gly Arg Ser Glu Gly Lys
    930                 935                 940

Ala Pro Leu Thr Glu Val Pro Glu Glu Gln Ala His Leu Asp Ala
945                 950                 955                 960

Asp Asp Ser Lys Glu Arg Arg Asn Ser Leu Asn Arg Leu Leu Phe Pro
                965                 970                 975

Lys Pro Thr Glu Glu Phe Leu Glu His Arg Arg Arg Phe Gly Asn Thr
            980                 985                 990

Ser Ala Leu Asp Asp Arg Glu Phe Phe Tyr Gly Leu Val Glu Gly Arg
        995                 1000                1005

Glu Thr Leu Ile Arg Leu Pro Asp Val Arg Thr Pro Leu Leu Val
    1010                1015                1020

Arg Leu Asp Ala Ile Ser Glu Glu Asp Asp Lys Gly Met Arg Asn
    1025                1030                1035

Val Val Ala Asn Val Asn Gly Gln Ile Arg Pro Met Arg Val Arg
    1040                1045                1050

Asp Arg Ser Val Glu Ser Val Thr Ala Thr Ala Glu Lys Ala Asp
    1055                1060                1065

Ser Ser Asn Lys Gly His Val Ala Ala Pro Phe Ala Gly Val Val
    1070                1075                1080

Thr Val Thr Val Ala Glu Gly Asp Glu Val Lys Ala Gly Asp Ala
    1085                1090                1095

Val Ala Ile Ile Glu Ala Met Lys Met Glu Ala Thr Ile Thr Ala
    1100                1105                1110

Ser Val Asp Gly Lys Ile Asp Arg Val Val Val Pro Ala Ala Thr
    1115                1120                1125

Lys Val Glu Gly Gly Asp Leu Ile Val Val Val Ser
    1130                1135                1140

<210> SEQ ID NO 21
<211> LENGTH: 3423
<212> TYPE: DNA
<213> ORGANISM: Corynebacterium glutamicum
```

<400> SEQUENCE: 21

```
atgtcgactc acacatcttc aacgcttcca gcattcaaaa agatcttggt agcaaaccgc      60
ggcgaaatcg cggtccgtgc tttccgtgca gcactcgaaa ccggtgcagc cacggtagct     120
atttaccccc gtgaagatcg gggatcattc caccgctctt ttgcttctga agctgtccgc     180
attggtaccg aaggctcacc agtcaaggcg tacctggaca tcgatgaaat tatcggtgca     240
gctaaaaaag ttaaagcaga tgccatttac ccgggatacg gcttcctgtc tgaaaatgcc     300
cagcttgccc gcgagtgtgc ggaaaacggc attacttttta ttggcccaac cccagaggtt    360
cttgatctca ccggtgataa gtctcgcgcg gtaaccgccg cgaagaaggc tggtctgcca     420
gttttggcgg aatccacccc gagcaaaaac atcgatgaga tcgttaaaag cgctgaaggc     480
cagacttacc ccatctttgt gaaggcagtt gccggtggtg gcggacgcgg tatgcgtttt     540
gttgcttcac ctgatgagct tcgcaaatta gcaacagaag catctcgtga agctgaagcg     600
gctttcggcg atgcgcggt atatgtcgaa cgtgctgtga ttaaccctca gcatattgaa      660
gtgcagatcc ttggcgatca cactggagaa gttgtacacc tttatgaacg tgactgctca     720
ctgcagcgtc gtcaccaaaa agttgtcgaa attgcgccag cacagcattt ggatccagaa     780
ctgcgtgatc gcatttgtgc ggatgcagta aagttctgcc gctccattgg ttaccagggc     840
gcgggaaccg tggaattctt ggtcgatgaa aagggcaacc acgtcttcat cgaaatgaac     900
ccacgtatcc aggttgagca caccgtgact gaagaagtca ccgaggtgga cctggtgaag     960
gcgcagatgc gcttggctgc tggtgcaacc ttgaaggaat tgggtctgac ccaagataag    1020
atcaagaccc acggtgcagc actgcagtgc cgcatcacca cggaagatcc aaacaacggc    1080
ttccgcccag ataccggaac tatcaccgcg taccgctcac caggcggagc tggcgttcgt    1140
cttgacggtg cagctcagct cggtggcgaa atcaccgcac actttgactc catgctggtg    1200
aaaatgacct gccgtggttc cgactttgaa actgctgttg ctcgtgcaca gcgcgcgttg    1260
gctgagttca ccgtgtctgg tgttgcaacc aacattggtt tcttgcgtgc gttgctgcgg    1320
gaagaggact tcacttccaa gcgcatcgcc accggattca ttgccgatca cccgcacctc    1380
cttcaggctc cacctgctga tgatgagcag ggacgcatcc tggattactt ggcagatgtc    1440
accgtgaaca gcctcatgg tgtgcgtcca aaggatgttg cagctcctat cgataagctg    1500
cctaacatca aggatctgcc actgccacgc ggttcccgtg accgcctgaa gcagcttggc    1560
ccagccgcgt ttgctcgtga tctccgtgag caggacgcac tggcagttac tgataccacc    1620
ttccgcgatg cacaccagtc tttgcttgcg acccgagtcc gctcattcgc actgaagcct    1680
gcggcagagg ccgtcgcaaa gctgactcct gagcttttgt ccgtggaggc ctggggcggc    1740
gcgacctacg atgtggcgat gcgtttcctc tttgaggatc cgtgggacag gctcgacgag    1800
ctgcgcgagg cgatgccgaa tgtaaacatt cagatgctgc ttcgcggccg caacaccgtg    1860
ggatacaccc cgtacccaga ctccgtctgc cgcgcgtttg ttaaggaagc tgccagctcc    1920
ggcgtggaca tcttccgcat cttcgacgcg cttaacgacg tctcccagat cgtccagca    1980
atcgacgcag tcctggagac caacaccgcg gtagccgagg tggctatggc ttattctggt    2040
gatctctctg atccaaatga aaagctctac accctggatt actacctaaa gatggcagag    2100
gagatcgtca agtctggcgc tcacatcttg gccattaagg atatggctgg tctgcttcgc    2160
ccagctgcgg taaccaagct ggtcaccgca ctgcgccgtg aattcgatct gccagtgcac    2220
gtgcacaccc acgacactgc gggtggccag ctggcaacct actttgctgc agctcaagct    2280
```

```
ggtgcagatg ctgttgacgg tgcttccgca ccactgtctg gcaccacctc ccagccatcc    2340
ctgtctgcca ttgttgctgc attcgcgcac acccgtcgcg ataccggttt gagcctcgag    2400
gctgtttctg acctcgagcc gtactgggaa gcagtgcgcg gactgtacct gccatttgag    2460
tctggaaccc caggcccaac cggtcgcgtc taccgccacg aaatcccagg cggacagttg    2520
tccaacctgc gtgcacaggc caccgcactg ggccttgcgg atcgtttcga actcatcgaa    2580
gacaactacg cagccgttaa tgagatgctg ggacgcccaa ccaaggtcac ccatcctcc    2640 aaggttgttg gcgacctcgc actccacctc gttggtgcgg gtgtggatcc agcagacttt    2700
gctgccgatc cacaaaagta cgacatccca gactctgtca tcgcgttcct gcgcggcgag    2760
cttggtaacc ctccaggtgg ctggccagag ccactgcgca cccgcgcact ggaaggccgc    2820
tccgaaggca aggcacctct gacggaagtt cctgaggaag agcaggcgca cctcgacgct    2880
gatgattcca aggaacgtcg caatagcctc aaccgcctgc tgttcccgaa gccaaccgaa    2940
gagttcctcg agcaccgtcg ccgcttcggc aacacctctg cgctggatga tcgtgaattc    3000
ttctacggcc tggtcgaagg ccgcgagact ttgatccgcc tgccagatgt gcgcaccca    3060 ctgcttgttc gcctggatgc gatctctgag ccagacgata agggtatgcg caatgttgtg    3120
gccaacgtca acggccagat ccgcccaatg cgtgtgcgtg accgctccgt tgagtctgtc    3180
accgcaaccg cagaaaaggc agattcctcc aacaagggcc atgttgctgc accattcgct    3240
ggtgttgtca ccgtgactgt tgctgaaggt gatgaggtca aggctggaga tgcagtcgca    3300
atcatcgagg ctatgaagat ggaagcaaca atcactgctt ctgttgacgg caaaatcgat    3360
cgcgttgtgg ttcctgctgc aacgaaggtg gaaggtggcg acttgatcgt cgtcgtttcc    3420
taa                                                                  3423
```

<210> SEQ ID NO 22
<211> LENGTH: 380
<212> TYPE: PRT
<213> ORGANISM: Aspergillus oryzae

<400> SEQUENCE: 22

```
Met Leu Thr Pro Pro Lys Phe Glu Asp Glu Lys Gln Leu Gly Pro Val
 1               5                  10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
```

```
                165                 170                 175
Thr Ile Ala Ser Val Ile Gly Glu Gln Gln Pro Ala Arg Ala Ala Leu
                180                 185                 190

Pro Ile Ile Gly Ala Gly Val Thr Phe Gln Gly Leu Gly Phe Ser Ile
                195                 200                 205

Ser Phe Met Met Tyr Ala His Tyr Ile Gly Arg Leu Met Glu Ser Gly
                210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
                260                 265                 270

Ile Ile Glu Leu Leu Ala Ile Ser Ala Gly Val Phe Leu Trp Ala Leu
                275                 280                 285

Ser Leu Trp Phe Phe Cys Ile Ala Ile Val Ala Val Ile Arg Ser Pro
                290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
                340                 345                 350

Tyr Ile Phe Val Phe Val Asn Asn Val Arg Ala Val Ile Arg Lys Asp
                355                 360                 365

Ile Met Tyr Pro Gly Lys Asp Glu Asp Val Ser Asp
                370                 375                 380

<210> SEQ ID NO 23
<211> LENGTH: 380
<212> TYPE: PRT
<213> ORGANISM: artificial sequence
<220> FEATURE:
<223> OTHER INFORMATION: mutant protein

<400> SEQUENCE: 23

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
                20                  25                  30

Thr Met Ser Gly Gly Gly Leu Ala Val Leu Ile Ile Ser Gln Pro Phe
                35                  40                  45

Gly Phe Arg Gly Leu Arg Glu Ile Gly Ile Ala Val Tyr Ile Leu Asn
                50                  55                  60

Leu Ile Leu Phe Ala Leu Val Cys Ser Thr Met Ala Ile Arg Phe Lys
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
                100                 105                 110

Ser Arg Tyr Phe Gly Glu Glu Ser Asn Glu Ser Phe Gln Leu Ala Leu
                115                 120                 125

Glu Ala Leu Phe Trp Ile Tyr Cys Val Cys Thr Leu Leu Val Ala Ile
                130                 135                 140

Ile Gln Tyr Ser Phe Val Phe Ser Ser His Lys Tyr Gly Leu Gln Thr
```

```
            145                 150                 155                 160
Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
                180                 185                 190

Pro Ile Ile Gly Ala Gly Val Thr Phe Gln Gly Leu Gly Phe Ser Ile
                195                 200                 205

Ser Phe Met Met Tyr Ala His Tyr Ile Gly Arg Leu Met Glu Ser Gly
                210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
                260                 265                 270

Ile Ile Glu Leu Leu Ala Ile Ser Ala Gly Val Phe Leu Trp Ala Leu
                275                 280                 285

Ser Leu Trp Phe Phe Cys Ile Ala Ile Val Ala Val Ile Arg Ser Pro
                290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
                340                 345                 350

Tyr Ile Phe Val Phe Val Asn Asn Val Arg Ala Val Ile Arg Lys Asp
                355                 360                 365

Ile Met Tyr Pro Gly Lys Asp Glu Asp Val Ser Asp
                370                 375                 380

<210> SEQ ID NO 24
<211> LENGTH: 380
<212> TYPE: PRT
<213> ORGANISM: artificial sequence
<220> FEATURE:
<223> OTHER INFORMATION: mutant protein

<400> SEQUENCE: 24

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
                20                  25                  30

Thr Met Ser Gly Gly Gly Leu Ala Val Leu Ile Ile Ser Gln Pro Phe
                35                  40                  45

Gly Phe Arg Gly Leu Arg Glu Ile Gly Ile Ala Val Tyr Ile Leu Asn
50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
                100                 105                 110

Ser Arg Tyr Phe Gly Glu Glu Ser Asn Glu Ser Phe Gln Leu Ala Leu
                115                 120                 125

Glu Ala Leu Phe Trp Ile Tyr Cys Val Cys Thr Leu Leu Val Ala Ile
```

```
                130                 135                 140
Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
                180                 185                 190

Pro Ile Ile Gly Ala Gly Val Thr Phe Gln Gly Leu Gly Phe Ser Ile
                195                 200                 205

Ser Phe Met Met Tyr Ala His Tyr Ile Gly Arg Leu Met Glu Ser Gly
                210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Ala
                260                 265                 270

Ile Ile Glu Leu Leu Ala Ile Ser Ala Gly Val Phe Leu Trp Ala Leu
                275                 280                 285

Ser Leu Trp Phe Phe Cys Ile Ala Ile Val Ala Val Ile Arg Ser Pro
                290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
                340                 345                 350

Tyr Ile Phe Val Phe Val Asn Asn Val Arg Ala Val Ile Arg Lys Asp
                355                 360                 365

Ile Met Tyr Pro Gly Lys Asp Glu Asp Val Ser Asp
                370                 375                 380

<210> SEQ ID NO 25
<211> LENGTH: 380
<212> TYPE: PRT
<213> ORGANISM: artificial sequence
<220> FEATURE:
<223> OTHER INFORMATION: mutant protein

<400> SEQUENCE: 25

Met Leu Thr Pro Pro Lys Phe Gln Asp Glu Lys Gln Leu Gly Pro Val
1               5                   10                  15

Gly Ile Arg Glu Arg Leu Arg His Phe Thr Trp Ala Trp Tyr Thr Leu
                20                  25                  30

Thr Met Ser Gly Gly Gly Leu Ala Val Leu Ile Ile Ser Gln Pro Phe
                35                  40                  45

Gly Phe Arg Gly Leu Arg Glu Ile Gly Ile Ala Val Tyr Ile Leu Asn
                50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
                100                 105                 110

Ser Arg Tyr Phe Gly Glu Glu Ser Asn Glu Ser Phe Gln Leu Ala Leu
```

```
                115                 120                 125
Glu Ala Leu Phe Trp Ile Tyr Cys Val Cys Thr Leu Leu Val Ala Ile
130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
            195                 200                 205

Ser Phe Met Met Tyr Ala His Tyr Ile Gly Arg Leu Met Glu Ser Gly
210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
            275                 280                 285

Ser Leu Trp Phe Phe Cys Ile Ala Ile Val Ala Ile Arg Ser Pro
290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
            355                 360                 365

Ile Met Tyr Pro Gly Lys Asp Glu Asp Val Ser Asp
370                 375                 380

<210> SEQ ID NO 26
<211> LENGTH: 380
<212> TYPE: PRT
<213> ORGANISM: artificial sequence
<220> FEATURE:
<223> OTHER INFORMATION: mutant protein

<400> SEQUENCE: 26

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
                20                  25                  30

Thr Met Ser Gly Gly Gly Leu Ala Val Leu Ile Ile Ser Gln Pro Phe
            35                  40                  45

Gly Phe Arg Gly Leu Arg Glu Ile Gly Ile Ala Val Tyr Ile Leu Asn
        50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
```

```
                100                 105                 110
Ser Arg Tyr Phe Gly Glu Glu Ser Asn Glu Ser Phe Gln Leu Ala Leu
            115                 120                 125

Glu Ala Leu Phe Trp Ile Tyr Cys Val Cys Thr Leu Leu Ile Ala Ile
130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
            165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
            195                 200                 205

Ser Phe Met Met Tyr Ala His Tyr Ile Gly Arg Leu Met Glu Ser Gly
            210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
            245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
            275                 280                 285

Ser Leu Trp Phe Phe Cys Ile Ala Ile Val Ala Val Ile Arg Ser Pro
            290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
            325                 330                 335

Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
            355                 360                 365

Ile Met Tyr Pro Gly Lys Asp Glu Asp Val Ser Asp
            370                 375                 380

<210> SEQ ID NO 27
<211> LENGTH: 380
<212> TYPE: PRT
<213> ORGANISM: artificial sequence
<220> FEATURE:
<223> OTHER INFORMATION: mutant protein

<400> SEQUENCE: 27

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
            35                  40                  45

Gly Phe Arg Gly Leu Arg Glu Ile Gly Ile Ala Val Tyr Ile Leu Asn
            50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
```

```
                    85                  90                  95
Val Phe Pro Thr Phe Trp Leu Ser Val Ala Thr Ile Ile Cys Gly Leu
                   100                 105                 110

Ser Arg Tyr Phe Gly Glu Glu Ser Asn Glu Ser Phe Gln Leu Ala Leu
                   115                 120                 125

Glu Ala Leu Phe Trp Ile Tyr Cys Val Cys Thr Leu Leu Val Ala Ile
                   130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                   165                 170                 175

Thr Ile Ala Ser Val Ile Gly Glu Gln Gln Pro Ala Arg Ala Ala Leu
                   180                 185                 190

Pro Ile Ile Gly Ala Gly Val Thr Phe Gln Gly Leu Gly Phe Ser Ile
                   195                 200                 205

Ser Phe Met Met Tyr Ala His Tyr Ile Gly Arg Leu Met Glu Ser Gly
                   210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                   245                 250                 255

Glu Asp Phe Lys Leu Leu His Asp Ala His Ala Leu Glu Asp Gly Arg
                   260                 265                 270

Ile Ile Glu Leu Leu Ala Ile Ser Ala Gly Val Phe Leu Trp Ala Leu
                   275                 280                 285

Ser Leu Trp Phe Phe Cys Ile Ala Ile Val Ala Val Ile Arg Ser Pro
                   290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                   325                 330                 335

Gly Val Lys Gly Val Gly Ser Ala Met Ser Ile Cys Ile Val Cys Met
                   340                 345                 350

Tyr Ile Phe Val Phe Val Asn Asn Val Arg Ala Val Ile Arg Lys Asp
                   355                 360                 365

Ile Met Tyr Pro Gly Lys Asp Glu Asp Val Ser Asp
                   370                 375                 380

<210> SEQ ID NO 28
<211> LENGTH: 380
<212> TYPE: PRT
<213> ORGANISM: artificial sequence
<220> FEATURE:
<223> OTHER INFORMATION: mutant protein

<400> SEQUENCE: 28

Met Leu Thr Pro Pro Lys Phe Glu Asp Glu Lys Gln Leu Gly Pro Val
1                   5                  10                  15

Gly Ile Arg Glu Arg Leu Arg His Phe Thr Trp Ala Trp Tyr Thr Leu
                   20                  25                  30

Thr Met Ser Gly Gly Gly Leu Ala Val Leu Ile Ile Ser Gln Pro Phe
                   35                  40                  45

Gly Phe Arg Gly Leu Arg Glu Ile Gly Ile Ala Val Tyr Ile Leu Asn
                   50                  55                  60

Leu Ile Leu Phe Ala Leu Val Cys Ser Thr Met Ala Ile Arg Phe Ile
```

```
                65                  70                  75                  80
Leu His Gly Asn Leu Leu Glu Ser Leu Arg His Asp Arg Glu Gly Leu
                85                  90                  95

Phe Phe Pro Thr Tyr Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
    210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Val Ile Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
        355                 360                 365

Ile Met Tyr Pro Gly Lys Asp Glu Asp Val Ser Asp
    370                 375                 380

<210> SEQ ID NO 29
<211> LENGTH: 380
<212> TYPE: PRT
<213> ORGANISM: artificial sequence
<220> FEATURE:
<223> OTHER INFORMATION: mutant protein

<400> SEQUENCE: 29

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
```

```
                    50                  55                  60
Leu Ile Leu Phe Ala Leu Val Cys Ser Thr Met Ala Ile Arg Phe Ile
 65                  70                  75                  80

Leu His Gly Asn Leu Leu Glu Ser Leu Arg His Asp Arg Glu Gly Leu
                     85                  90                  95

Phe Phe Pro Thr Phe Trp Leu Ser Val Ala Thr Ile Ile Cys Gly Leu
                    100                 105                 110

Ser Arg Glu Phe Gly Glu Glu Ser Asn Glu Ser Phe Gln Leu Ala Leu
                    115                 120                 125

Glu Ala Leu Phe Trp Ile Tyr Cys Val Cys Thr Leu Leu Val Ala Ile
                130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                    165                 170                 175

Thr Ile Ala Ser Val Ile Gly Glu Gln Gln Pro Ala Arg Ala Ala Leu
                    180                 185                 190

Pro Ile Ile Gly Ala Gly Val Thr Phe Gln Gly Leu Gly Phe Ser Ile
                    195                 200                 205

Ser Phe Met Met Tyr Ala His Tyr Ile Gly Arg Leu Met Glu Ser Gly
                210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                    245                 250                 255

Glu Asp Phe Lys Leu Leu His Asp Ala His Ala Leu Glu Asp Gly Arg
                    260                 265                 270

Ile Ile Glu Leu Leu Ala Ile Ser Ala Gly Val Phe Leu Trp Ala Leu
                    275                 280                 285

Ser Leu Trp Phe Phe Cys Ile Ala Ile Val Ala Val Ile Arg Ser Pro
                290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                    325                 330                 335

Gly Val Lys Gly Val Gly Ser Ala Met Ser Ile Cys Ile Val Cys Met
                    340                 345                 350

Tyr Ile Phe Val Phe Val Asn Asn Val Arg Ala Val Ile Arg Lys Asp
                    355                 360                 365

Ile Met Tyr Pro Gly Lys Asp Glu Asp Val Ser Asp
                    370                 375                 380

<210> SEQ ID NO 30
<211> LENGTH: 380
<212> TYPE: PRT
<213> ORGANISM: artificial sequence
<220> FEATURE:
<223> OTHER INFORMATION: mutant protein

<400> SEQUENCE: 30

Met Leu Thr Pro Pro Lys Phe Glu Asp Glu Lys Gln Leu Gly Pro Val
  1               5                  10                  15

Gly Ile Arg Glu Arg Leu Arg His Phe Thr Trp Ala Trp Tyr Thr Leu
                 20                  25                  30

Thr Met Ser Gly Gly Gly Leu Ala Val Leu Ile Ile Ser Gln Pro Phe
```

```
                35                  40                  45
Gly Phe Arg Gly Leu Arg Glu Ile Gly Ile Ala Val Tyr Ile Leu Asn
 50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Lys Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
    210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Val Ile Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
        355                 360                 365

Ile Met Tyr Pro Gly Lys Asp Glu Asp Val Ser Asp
    370                 375                 380

<210> SEQ ID NO 31
<211> LENGTH: 380
<212> TYPE: PRT
<213> ORGANISM: artificial sequence
<220> FEATURE:
<223> OTHER INFORMATION: mutant protein

<400> SEQUENCE: 31

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
```

```
            20                  25                  30
Thr Met Ser Gly Gly Gly Leu Ala Val Leu Ile Ile Ser Gln Pro Phe
        35                  40                  45
Gly Phe Arg Gly Leu Arg Glu Ile Gly Ile Ala Val Tyr Ile Leu Asn
    50                  55                  60
Leu Ile Leu Phe Ala Leu Val Cys Ser Thr Met Ala Ile Arg Phe Ile
65                  70                  75                  80
Leu His Gly Asn Leu Leu Glu Ser Leu Arg His Asp Arg Glu Gly Leu
                85                  90                  95
Phe Phe Pro Thr Phe Trp Leu Ser Val Ala Thr Ile Ile Cys Gly Leu
            100                 105                 110
Ser Arg Tyr Phe Gly Glu Glu Ser Asn Glu Ser Phe Gln Leu Ala Leu
        115                 120                 125
Glu Ala Leu Phe Trp Ile Tyr Cys Val Cys Thr Leu Leu Val Ala Ile
    130                 135                 140
Ile Gln Tyr Ser Phe Val Phe Ser Ser His Lys Tyr Gly Leu Gln Thr
145                 150                 155                 160
Met Met Pro Ser Trp Ile Leu Pro Ala Phe Pro Ile Met Leu Ser Gly
                165                 170                 175
Thr Ile Ala Ser Val Ile Gly Glu Gln Gln Pro Ala Arg Ala Ala Leu
            180                 185                 190
Pro Ile Ile Gly Ala Gly Val Thr Phe Gln Gly Leu Gly Phe Ser Ile
        195                 200                 205
Ser Phe Met Met Tyr Ala His Tyr Ile Gly Arg Leu Met Glu Ser Gly
    210                 215                 220
Leu Pro His Ser Asp His Arg Pro Gly Met Phe Ile Cys Val Gly Pro
225                 230                 235                 240
Pro Ala Phe Thr Ala Leu Ala Leu Val Gly Met Ser Lys Gly Leu Pro
                245                 250                 255
Glu Asp Phe Lys Leu Leu His Asp Ala His Ala Leu Glu Asp Gly Arg
            260                 265                 270
Ile Ile Glu Leu Leu Ala Ile Ser Ala Gly Val Phe Leu Trp Ala Leu
        275                 280                 285
Ser Leu Trp Phe Phe Cys Ile Ala Ile Val Ala Val Trp Arg Ser Pro
    290                 295                 300
Pro Glu Ala Phe His Leu Asn Trp Trp Ala Met Val Phe Pro Asn Thr
305                 310                 315                 320
Gly Phe Thr Leu Ala Thr Ile Thr Leu Gly Lys Ala Leu Asn Ser Asn
                325                 330                 335
Gly Val Lys Gly Val Gly Ser Ala Met Ser Ile Cys Ile Val Cys Met
            340                 345                 350
Tyr Ile Phe Val Phe Val Asn Asn Val Arg Ala Val Ile Arg Lys Asp
        355                 360                 365
Ile Met Tyr Pro Gly Lys Asp Glu Asp Val Ser Asp
    370                 375                 380

<210> SEQ ID NO 32
<211> LENGTH: 380
<212> TYPE: PRT
<213> ORGANISM: artificial sequence
<220> FEATURE:
<223> OTHER INFORMATION: mutant protein

<400> SEQUENCE: 32

Met Leu Thr Pro Pro Lys Phe Glu Asp Glu Lys Gln Leu Gly Pro Val
```

```
  1               5                   10                  15
Gly Ile Arg Glu Arg Leu Arg His Phe Thr Trp Ala Trp Tyr Thr Leu
                20                  25                  30
Thr Met Ser Gly Gly Gly Leu Ala Val Leu Ile Ile Ser Gln Pro Phe
                35                  40                  45
Gly Phe Arg Gly Leu Arg Glu Ile Gly Ile Ala Val Tyr Ile Leu Asn
                50                  55                  60
Leu Ile Leu Phe Ala Leu Val Cys Ser Thr Met Ala Ile Arg Phe Ile
 65                 70                  75                  80
Leu His Gly Asn Leu Leu Glu Ser Leu Arg His Asp Arg Glu Gly Leu
                85                  90                  95
Phe Phe Pro Thr Phe Trp Leu Ser Val Ala Thr Ile Ile Cys Gly Leu
                100                 105                 110
Ser Arg Tyr Phe Gly Glu Glu Ser Asn Glu Ser Phe Gln Leu Ala Leu
                115                 120                 125
Glu Ala Leu Phe Trp Ile Tyr Cys Val Cys Thr Asn Leu Val Ala Ile
                130                 135                 140
Ile Gln Tyr Ser Phe Val Phe Ser Ser His Lys Tyr Gly Leu Gln Thr
145                 150                 155                 160
Met Met Pro Ser Trp Ile Leu Pro Ala Phe Pro Ile Met Leu Ser Gly
                165                 170                 175
Thr Ile Ala Ser Val Ile Gly Glu Gln Gln Pro Ala Arg Ala Ala Leu
                180                 185                 190
Pro Ile Ile Gly Ala Gly Val Thr Phe Gln Gly Leu Gly Phe Ser Ile
                195                 200                 205
Ser Phe Met Met Tyr Ala His Tyr Ile Gly Arg Leu Met Glu Ser Gly
                210                 215                 220
Leu Pro His Ser Asp His Arg Pro Gly Met Phe Ile Cys Val Gly Pro
225                 230                 235                 240
Pro Ala Phe Thr Ala Leu Ala Leu Val Gly Met Ser Lys Gly Leu Pro
                245                 250                 255
Glu Asp Phe Lys Leu Leu His Asp Ala His Ala Leu Glu Asp Gly Arg
                260                 265                 270
Ile Ile Glu Leu Leu Ala Ile Ser Ala Gly Val Phe Leu Trp Ala Leu
                275                 280                 285
Ser Leu Trp Phe Phe Cys Ile Ala Ile Val Ala Ile Arg Ser Pro
                290                 295                 300
Pro Glu Ala Phe His Leu Asn Trp Trp Ala Met Val Phe Pro Asn Thr
305                 310                 315                 320
Gly Phe Thr Leu Ala Thr Ile Thr Leu Gly Lys Ala Leu Asn Ser Asn
                325                 330                 335
Gly Val Lys Gly Val Gly Ser Ala Met Ser Ile Cys Ile Val Cys Met
                340                 345                 350
Tyr Ile Phe Val Phe Val Asn Asn Val Arg Ala Val Ile Arg Lys Asp
                355                 360                 365
Ile Met Tyr Pro Gly Lys Asp Glu Asp Val Ser Asp
370                 375                 380

<210> SEQ ID NO 33
<211> LENGTH: 380
<212> TYPE: PRT
<213> ORGANISM: artificial sequence
<220> FEATURE:
<223> OTHER INFORMATION: mutant protein
```

```
<400> SEQUENCE: 33

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Ile Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
    210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Val Ile Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
        355                 360                 365

Ile Met Tyr Pro Gly Lys Asp Glu Asp Val Ser Asp
    370                 375                 380

<210> SEQ ID NO 34
<211> LENGTH: 380
<212> TYPE: PRT
<213> ORGANISM: artificial sequence
```

<220> FEATURE:
<223> OTHER INFORMATION: mutant protein

<400> SEQUENCE: 34

```
Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Arg Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
    210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Val Ile Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
        355                 360                 365

Ile Met Tyr Pro Gly Lys Asp Glu Asp Val Ser Asp
    370                 375                 380
```

<210> SEQ ID NO 35

<211> LENGTH: 380
<212> TYPE: PRT
<213> ORGANISM: artificial sequence
<220> FEATURE:
<223> OTHER INFORMATION: mutant protein

<400> SEQUENCE: 35

```
Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Gln Gln Gly Leu Gly Phe Ser Ile
        195                 200                 205

Ser Phe Met Met Tyr Ala His Tyr Ile Gly Arg Leu Met Glu Ser Gly
    210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Val Ala Val Ile Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
        355                 360                 365

Ile Met Tyr Pro Gly Lys Asp Glu Asp Val Ser Asp
    370                 375                 380
```

<210> SEQ ID NO 36
<211> LENGTH: 380
<212> TYPE: PRT
<213> ORGANISM: artificial sequence
<220> FEATURE:
<223> OTHER INFORMATION: mutant protein

<400> SEQUENCE: 36

```
Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Ser Ser Gly
    210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Val Ile Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
        355                 360                 365
```

```
Ile Met Tyr Pro Gly Lys Asp Glu Asp Val Ser Asp
    370                 375                 380

<210> SEQ ID NO 37
<211> LENGTH: 380
<212> TYPE: PRT
<213> ORGANISM: artificial sequence
<220> FEATURE:
<223> OTHER INFORMATION: mutant protein

<400> SEQUENCE: 37

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Leu Ala Val Leu Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
    210                 215                 220

Leu Pro Phe Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Val Ile Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
            340                 345                 350
```

Tyr Ile Phe Val Phe Val Asn Asn Val Arg Ala Val Ile Arg Lys Asp
            355                 360                 365

Ile Met Tyr Pro Gly Lys Asp Glu Asp Val Ser Asp
370                 375                 380

<210> SEQ ID NO 38
<211> LENGTH: 380
<212> TYPE: PRT
<213> ORGANISM: artificial sequence
<220> FEATURE:
<223> OTHER INFORMATION: mutant protein

<400> SEQUENCE: 38

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
                85                  90                  95

Phe Phe Pro Thr Phe Trp Leu Ser Val Ala Thr Ile Met Cys Gly Leu
            100                 105                 110

Ser Arg Tyr Phe Gly Glu Glu Ser Asn Glu Ser Phe Gln Leu Ala Leu
        115                 120                 125

Glu Ala Leu Phe Trp Ile Tyr Cys Val Cys Thr Leu Leu Val Ala Ile
    130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
        195                 200                 205

Ser Phe Met Met Tyr Ala His Tyr Ile Gly Arg Leu Met Glu Ser Gly
    210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Met Ser Lys Gly Leu Pro
                245                 250                 255

Glu Asp Phe Lys Leu Leu His Asp Ala His Ala Leu Glu Asp Gly Arg
            260                 265                 270

Ile Ile Glu Leu Leu Ala Ile Ser Ala Gly Val Phe Leu Trp Ala Leu
        275                 280                 285

Ser Leu Trp Phe Phe Cys Ile Ala Ile Val Ala Ile Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

```
Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
            355                 360                 365

Ile Met Tyr Pro Gly Lys Asp Glu Asp Val Ser Asp
            370                 375                 380

<210> SEQ ID NO 39
<211> LENGTH: 213
<212> TYPE: PRT
<213> ORGANISM: artificial sequence
<220> FEATURE:
<223> OTHER INFORMATION: mutant protein

<400> SEQUENCE: 39

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Ile
65                  70                  75                  80

Leu His Gly Asn Leu Leu Glu Ser Leu Arg His Asp Arg Glu Gly Leu
            85                  90                  95

Phe Phe Pro Thr Phe Trp Leu Ser Val Ala Thr Ile Ile Cys Gly Leu
            100                 105                 110

Ser Arg Tyr Phe Gly Glu Glu Ser Asn Glu Ser Phe Gln Leu Ala Leu
            115                 120                 125

Glu Ala Leu Phe Trp Ile Tyr Cys Val Cys Thr Leu Leu Val Ala Ile
        130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
            165                 170                 175

Thr Ile Ala Ser Val Ile Gly Glu Gln Gln Pro Ala Arg Ala Ala Leu
            180                 185                 190

Pro Ile Ile Gly Ala Gly Val Thr Phe Gln Gly Leu Gly Phe Ser Ile
            195                 200                 205

Ser Phe Met Met Tyr
        210

<210> SEQ ID NO 40
<211> LENGTH: 380
<212> TYPE: PRT
<213> ORGANISM: artificial sequence
<220> FEATURE:
<223> OTHER INFORMATION: mutant protein

<400> SEQUENCE: 40

Met Leu Thr Pro Pro Lys Phe Glu Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
```

```
                35                  40                  45
Gly Phe Arg Gly Leu Arg Glu Ile Gly Ile Ala Val Tyr Ile Leu Asn
 50                  55                  60

Leu Ile Leu Phe Ala Leu Val Cys Ser Thr Met Ala Ile Arg Phe Ile
 65                  70                  75                  80

Leu His Gly Asn Leu Leu Glu Ser Leu Arg His Asp Arg Glu Gly Leu
                 85                  90                  95

Phe Phe Pro Thr Phe Trp Leu Ser Val Ala Thr Ile Ile Cys Gly Leu
                100                 105                 110

Ser Arg Tyr Phe Gly Glu Glu Ser Asn Glu Ser Phe Gln Leu Ala Leu
                115                 120                 125

Glu Ala Leu Phe Trp Ile Tyr Cys Val Cys Thr Leu Leu Val Ala Ile
                130                 135                 140

Ile Gln Tyr Ser Phe Val Phe Ser Ser His Lys Tyr Gly Leu Gln Thr
145                 150                 155                 160

Met Met Pro Ser Trp Ile Leu Pro Ala Phe Pro Ile Met Leu Ser Gly
                165                 170                 175

Thr Ile Ala Ser Val Ile Gly Glu Gln Gln Pro Ala Arg Ala Ala Leu
                180                 185                 190

Pro Ile Ile Gly Ala Gly Val Thr Phe Gln Gly Leu Gly Phe Ser Ile
                195                 200                 205

Ser Phe Met Met Tyr Ala His Tyr Ile Gly Arg Leu Met Glu Ser Gly
                210                 215                 220

Leu Pro His Ser Asp His Arg Pro Gly Met Phe Ile Cys Val Gly Pro
225                 230                 235                 240

Pro Ala Phe Thr Ala Leu Ala Leu Val Gly Glu Ser Lys Gly Leu Pro
                245                 250                 255

Glu Asp Phe Lys Leu Leu His Asp Ala His Ala Leu Glu Asp Gly Arg
                260                 265                 270

Ile Ile Glu Leu Leu Ala Ile Ser Ala Gly Val Phe Leu Trp Ala Leu
                275                 280                 285

Ser Leu Trp Phe Phe Cys Ile Ala Ile Val Ala Val Ile Arg Ser Pro
                290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
                325                 330                 335

Gly Val Lys Gly Val Gly Ser Ala Met Ser Ile Cys Ile Val Cys Met
                340                 345                 350

Tyr Ile Phe Val Phe Val Asn Asn Val Arg Ala Val Ile Arg Lys Asp
                355                 360                 365

Ile Met Tyr Pro Gly Lys Asp Glu Asp Val Ser Asp
                370                 375                 380

<210> SEQ ID NO 41
<211> LENGTH: 380
<212> TYPE: PRT
<213> ORGANISM: artificial sequence
<220> FEATURE:
<223> OTHER INFORMATION: mutant protein

<400> SEQUENCE: 41

Met Leu Thr Pro Pro Lys Phe Glu Asp Glu Lys Gln Leu Gly Pro Val
 1               5                  10                  15

Gly Ile Arg Glu Arg Leu Arg His Phe Thr Trp Ala Trp Tyr Thr Leu
```

20                  25                  30
Thr Met Ser Gly Gly Gly Leu Ala Val Leu Ile Ile Ser Gln Pro Phe
         35                  40                  45
Gly Phe Arg Gly Leu Arg Glu Ile Gly Ile Ala Val Tyr Ile Leu Asn
     50                  55                  60
Leu Ile Leu Phe Ala Leu Val Cys Ser Thr Met Ala Ile Arg Phe Lys
 65                  70                  75                  80
Leu His Gly Asn Leu Leu Glu Ser Leu Arg His Asp Arg Glu Gly Leu
                 85                  90                  95
Phe Phe Pro Thr Phe Trp Leu Ser Val Ala Thr Ile Ile Cys Gly Leu
            100                 105                 110
Ser Arg Tyr Phe Gly Glu Glu Ser Asn Glu Ser Phe Gln Leu Ala Leu
        115                 120                 125
Glu Ala Leu Phe Trp Ile Tyr Cys Val Cys Thr Leu Leu Val Ala Ile
    130                 135                 140
Ile Gln Tyr Ser Phe Val Phe Ser Ser His Lys Tyr Gly Leu Gln Thr
145                 150                 155                 160
Met Met Pro Ser Trp Ile Leu Pro Ala Phe Pro Ile Met Leu Ser Gly
                165                 170                 175
Thr Ile Ala Ser Val Ile Gly Glu Gln Gln Pro Ala Arg Ala Ala Leu
            180                 185                 190
Pro Ile Ile Gly Ala Gly Val Thr Phe Gln Gly Leu Gly Phe Ser Ile
        195                 200                 205
Ser Phe Met Met Tyr Ala His Tyr Ile Gly Arg Leu Met Glu Ser Gly
    210                 215                 220
Leu Pro His Ser Asp His Arg Pro Gly Met Phe Ile Cys Val Gly Pro
225                 230                 235                 240
Pro Ala Phe Thr Ala Leu Ala Leu Val Gly Met Ser Lys Gly Leu Pro
                245                 250                 255
Glu Asp Phe Lys Leu Leu His Asp Ala His Ala Leu Glu Asp Gly Ala
            260                 265                 270
Ile Ile Glu Leu Leu Ala Ile Ser Ala Gly Val Phe Leu Trp Ala Leu
        275                 280                 285
Ser Leu Trp Phe Phe Cys Ile Ala Ile Val Ala Val Ile Arg Ser Pro
    290                 295                 300
Pro Glu Ala Phe His Leu Asn Trp Trp Ala Met Val Phe Pro Asn Thr
305                 310                 315                 320
Gly Phe Thr Leu Ala Thr Ile Thr Leu Gly Lys Ala Leu Asn Ser Asn
                325                 330                 335
Gly Val Lys Gly Val Gly Ser Ala Met Ser Ile Cys Ile Val Cys Met
            340                 345                 350
Tyr Ile Phe Val Phe Val Asn Asn Val Arg Ala Val Ile Arg Lys Asp
        355                 360                 365
Ile Met Tyr Pro Gly Lys Asp Glu Asp Val Ser Asp
    370                 375                 380

<210> SEQ ID NO 42
<211> LENGTH: 380
<212> TYPE: PRT
<213> ORGANISM: artificial sequence
<220> FEATURE:
<223> OTHER INFORMATION: mutant protein

<400> SEQUENCE: 42

Met Leu Thr Pro Pro Lys Phe Gln Asp Glu Lys Gln Leu Gly Pro Val

|   |   |   |   |   |   |   |   |   |   |   |   |   |   |   |   |
|---|---|---|---|---|---|---|---|---|---|---|---|---|---|---|---|
| 1 |   |   |   | 5 |   |   |   |   | 10 |   |   |   |   | 15 |   |
| Gly | Ile | Arg | Glu | Arg | Leu | Arg | His | Phe | Thr | Trp | Ala | Trp | Tyr | Thr | Leu |
|   |   |   | 20 |   |   |   |   | 25 |   |   |   |   | 30 |   |   |
| Thr | Met | Ser | Gly | Gly | Gly | Leu | Ala | Val | Leu | Ile | Ile | Ser | Gln | Pro | Phe |
|   |   | 35 |   |   |   |   | 40 |   |   |   |   | 45 |   |   |   |
| Gly | Phe | Arg | Gly | Leu | Arg | Glu | Ile | Gly | Ile | Ala | Val | Tyr | Ile | Leu | Asn |
|   | 50 |   |   |   |   | 55 |   |   |   |   | 60 |   |   |   |   |
| Leu | Ile | Leu | Phe | Ala | Leu | Val | Cys | Ser | Thr | Met | Ala | Ile | Arg | Phe | Lys |
| 65 |   |   |   |   | 70 |   |   |   |   | 75 |   |   |   |   | 80 |
| Leu | His | Gly | Asn | Leu | Leu | Glu | Ser | Leu | Arg | His | Asp | Arg | Glu | Gly | Leu |
|   |   |   |   | 85 |   |   |   |   | 90 |   |   |   |   | 95 |   |
| Phe | Phe | Pro | Thr | Phe | Trp | Leu | Ser | Val | Ala | Thr | Ile | Ile | Cys | Gly | Leu |
|   |   |   | 100 |   |   |   |   | 105 |   |   |   |   | 110 |   |   |
| Ser | Arg | Tyr | Phe | Gly | Glu | Glu | Ser | Asn | Glu | Ser | Phe | Gln | Leu | Ala | Leu |
|   |   |   | 115 |   |   |   |   | 120 |   |   |   |   | 125 |   |   |
| Glu | Ala | Leu | Phe | Trp | Ile | Tyr | Cys | Val | Cys | Thr | Leu | Leu | Val | Ala | Ile |
|   |   | 130 |   |   |   |   | 135 |   |   |   |   | 140 |   |   |   |
| Ile | Gln | Tyr | Ser | Phe | Val | Phe | Ser | Ser | His | Lys | Tyr | Gly | Leu | Gln | Thr |
| 145 |   |   |   |   | 150 |   |   |   |   | 155 |   |   |   |   | 160 |
| Met | Met | Pro | Ser | Trp | Ile | Leu | Pro | Ala | Phe | Pro | Ile | Met | Leu | Ser | Gly |
|   |   |   |   | 165 |   |   |   |   | 170 |   |   |   |   | 175 |   |
| Thr | Ile | Ala | Ser | Val | Ile | Gly | Glu | Gln | Gln | Pro | Ala | Arg | Ala | Ala | Leu |
|   |   |   | 180 |   |   |   |   | 185 |   |   |   |   | 190 |   |   |
| Pro | Ile | Ile | Gly | Ala | Gly | Val | Thr | Phe | Gln | Gly | Leu | Gly | Phe | Ser | Ile |
|   |   | 195 |   |   |   |   | 200 |   |   |   |   | 205 |   |   |   |
| Ser | Phe | Met | Met | Tyr | Ala | His | Tyr | Ile | Gly | Arg | Leu | Met | Glu | Ser | Gly |
|   | 210 |   |   |   |   | 215 |   |   |   |   | 220 |   |   |   |   |
| Leu | Pro | His | Ser | Asp | His | Arg | Pro | Gly | Met | Phe | Ile | Cys | Val | Gly | Pro |
| 225 |   |   |   |   | 230 |   |   |   |   | 235 |   |   |   |   | 240 |
| Pro | Ala | Phe | Thr | Ala | Leu | Ala | Leu | Val | Gly | Met | Ser | Lys | Gly | Leu | Pro |
|   |   |   | 245 |   |   |   |   | 250 |   |   |   |   | 255 |   |   |
| Glu | Asp | Phe | Lys | Leu | Leu | His | Asp | Ala | His | Ala | Leu | Glu | Asp | Gly | Ala |
|   |   |   | 260 |   |   |   |   | 265 |   |   |   |   | 270 |   |   |
| Ile | Ile | Glu | Leu | Leu | Ala | Ile | Ser | Ala | Gly | Val | Phe | Leu | Trp | Ala | Leu |
|   |   | 275 |   |   |   |   | 280 |   |   |   |   | 285 |   |   |   |
| Ser | Leu | Trp | Phe | Phe | Cys | Ile | Ala | Ile | Val | Ala | Val | Ile | Arg | Ser | Pro |
|   | 290 |   |   |   |   | 295 |   |   |   |   | 300 |   |   |   |   |
| Pro | Glu | Ala | Phe | His | Leu | Asn | Trp | Trp | Ala | Met | Val | Phe | Pro | Asn | Thr |
| 305 |   |   |   |   | 310 |   |   |   |   | 315 |   |   |   |   | 320 |
| Gly | Phe | Thr | Leu | Ala | Thr | Ile | Thr | Leu | Gly | Lys | Ala | Leu | Asn | Ser | Asn |
|   |   |   | 325 |   |   |   |   | 330 |   |   |   |   | 335 |   |   |
| Gly | Val | Lys | Gly | Val | Gly | Ser | Ala | Met | Ser | Ile | Cys | Ile | Val | Cys | Met |
|   |   | 340 |   |   |   |   | 345 |   |   |   |   | 350 |   |   |   |
| Tyr | Ile | Phe | Val | Phe | Val | Asn | Asn | Val | Arg | Ala | Val | Ile | Arg | Lys | Asp |
|   |   | 355 |   |   |   |   | 360 |   |   |   |   | 365 |   |   |   |
| Ile | Met | Tyr | Pro | Gly | Lys | Asp | Glu | Asp | Val | Ser | Asp |   |   |   |   |
|   | 370 |   |   |   |   | 375 |   |   |   |   | 380 |   |   |   |   |

<210> SEQ ID NO 43
<211> LENGTH: 1143
<212> TYPE: DNA
<213> ORGANISM: Aspergillus oryzae

<400> SEQUENCE: 43

```
atgctgacac ctcccaagtt tgaggatgag aagcagctgg gccccgtggg tatccgggag    60
aggcttcgcc atttcacttg ggcctggtac acattaacga tgagtggagg agggctggcc   120
gtcctcatca tcagccagcc cttttgggttc cgcggattga gagagatcgg catcgctgtc  180
tatatcctca acctgatcct cttcgcccct tgtctgctcta ccatggctat aaggttcatc  240
ctgcacggca accttctgga gtccctccgt catgaccgcg agggtctctt cttcccgacc   300
ttctggctct ccgtcgcaac catcatctgc ggcttgtctc gctacttcgg tgaagaatcg  360
aatgagtcct tccaactagc cctcgaagcc ctcttctgga tctactgcgt ctgcaccttta 420
ctcgtcgcaa tcatccaata ctcgttcgtc ttctcatccc acaagtacgg ccttcaaacc  480
atgatgcctt catggatcct tccagccttc cccatcatgc tcagcggcac catcgcctcc  540
gtcatcggtg aacaacaacc cgctcgcgca gccctcccca tcatcggcgc cggcgtcacc  600
ttccagggcc tcggcttctc catcagcttc atgatgtacg cccactacat cggccgactg  660
atggagtccg gcctccccca cagcgaccac agaccaggca tgttcatctg cgtcggaccc  720
cccgccttca cagccctcgc cctcgtcggc atgagcaaag gcctccccga agacttcaag  780
ctgctccacg acgccacgcc cctggaagat ggccgcatca tcgagctgct ggccatctcc  840
gccggcgtct tcctctgggc cctgagtctc tggttcttct gcatcgccat tgtcgccgtc  900
atccgctcgc cccccgaggc cttccacctc aactggtggg ccatggtctt ccccaacacc  960
ggcttcaccc tggccaccat caccctgggc aaggctctca acagtaacgg tgtgaagggc 1020
gtcggttccg ccatgtctat ctgcatcgtg tgcatgtata tcttcgtctt cgtcaacaat 1080
gtccgcgccg ttatccggaa ggatatcatg tacccgggta agatgagga tgtatctgat 1140
tag                                                                1143

<210> SEQ ID NO 44
<211> LENGTH: 43
<212> TYPE: DNA
<213> ORGANISM: artificial sequence
<220> FEATURE:
<223> OTHER INFORMATION: primer

<400> SEQUENCE: 44
ccaccgcccg ttaccgtccg aaggaaattt tactctgctg gag                     43

<210> SEQ ID NO 45
<211> LENGTH: 43
<212> TYPE: DNA
<213> ORGANISM: artificial sequence
<220> FEATURE:
<223> OTHER INFORMATION: primer

<400> SEQUENCE: 45
ctccagcaga gtaaaatttc cttcggacgg taacgggcgg tgg                     43

<210> SEQ ID NO 46
<211> LENGTH: 34
<212> TYPE: DNA
<213> ORGANISM: artificial sequence
<220> FEATURE:
<223> OTHER INFORMATION: primer

<400> SEQUENCE: 46
gggttcgaaa cgatggccga agaagactac tccc                               34

<210> SEQ ID NO 47
<211> LENGTH: 39
```

```
<212> TYPE: DNA
<213> ORGANISM: artificial sequence
<220> FEATURE:
<223> OTHER INFORMATION: primer

<400> SEQUENCE: 47
ggggcggccg cttactcagc cttgacgatt ttggcgatc                              39

<210> SEQ ID NO 48
<211> LENGTH: 37
<212> TYPE: DNA
<213> ORGANISM: artificial sequence
<220> FEATURE:
<223> OTHER INFORMATION: primer

<400> SEQUENCE: 48
gggttcgaaa cgatggttaa agtcacagtt tgcggag                                37

<210> SEQ ID NO 49
<211> LENGTH: 38
<212> TYPE: DNA
<213> ORGANISM: artificial sequence
<220> FEATURE:
<223> OTHER INFORMATION: primer

<400> SEQUENCE: 49
ggggcggccg cttagttgcc agcaatgaag gcagttcc                               38

<210> SEQ ID NO 50
<211> LENGTH: 30
<212> TYPE: DNA
<213> ORGANISM: artificial sequence
<220> FEATURE:
<223> OTHER INFORMATION: primer

<400> SEQUENCE: 50
gggggatcct gtacagcttg cctcgtcccc                                        30

<210> SEQ ID NO 51
<211> LENGTH: 24
<212> TYPE: DNA
<213> ORGANISM: artificial sequence
<220> FEATURE:
<223> OTHER INFORMATION: primer

<400> SEQUENCE: 51
gtcgacactg gatggcggcg ttag                                              24

<210> SEQ ID NO 52
<211> LENGTH: 34
<212> TYPE: DNA
<213> ORGANISM: artificial sequence
<220> FEATURE:
<223> OTHER INFORMATION: primer

<400> SEQUENCE: 52
gggagatctg ttgtaacact ggcagagcat tacg                                   34

<210> SEQ ID NO 53
<211> LENGTH: 32
<212> TYPE: DNA
<213> ORGANISM: artificial sequence
<220> FEATURE:
<223> OTHER INFORMATION: primer

<400> SEQUENCE: 53
```

```
gggggatccg tcccagtttc tccatacgaa cc                              32
```

<210> SEQ ID NO 54
<211> LENGTH: 33
<212> TYPE: DNA
<213> ORGANISM: artificial sequence
<220> FEATURE:
<223> OTHER INFORMATION: primer

<400> SEQUENCE: 54

```
gggatcgata tgggtgaact caaggaaatc ttg                             33
```

<210> SEQ ID NO 55
<211> LENGTH: 38
<212> TYPE: DNA
<213> ORGANISM: artificial sequence
<220> FEATURE:
<223> OTHER INFORMATION: primer

<400> SEQUENCE: 55

```
ggggcggccg cttaaacgct ttcatgttca ctactagg                        38
```

<210> SEQ ID NO 56
<211> LENGTH: 31
<212> TYPE: DNA
<213> ORGANISM: artificial sequence
<220> FEATURE:
<223> OTHER INFORMATION: primer

<400> SEQUENCE: 56

```
gggttcgaaa tgctgacacc tcccaagttt g                               31
```

<210> SEQ ID NO 57
<211> LENGTH: 37
<212> TYPE: DNA
<213> ORGANISM: artificial sequence
<220> FEATURE:
<223> OTHER INFORMATION: primer

<400> SEQUENCE: 57

```
ggggcggccg cctaatcaga tacatcctca tctttac                         37
```

<210> SEQ ID NO 58
<211> LENGTH: 34
<212> TYPE: DNA
<213> ORGANISM: artificial sequence
<220> FEATURE:
<223> OTHER INFORMATION: primer

<400> SEQUENCE: 58

```
ggggaattca tggctgcaga atcaatagtg tctc                            34
```

<210> SEQ ID NO 59
<211> LENGTH: 43
<212> TYPE: DNA
<213> ORGANISM: artificial sequence
<220> FEATURE:
<223> OTHER INFORMATION: primer

<400> SEQUENCE: 59

```
ggggcggccg cttatgttga atttcttgct tgaaatttag atc                  43
```

<210> SEQ ID NO 60
<211> LENGTH: 24
<212> TYPE: DNA
<213> ORGANISM: artificial sequence

```
<220> FEATURE:
<223> OTHER INFORMATION: primer

<400> SEQUENCE: 60
ctgcgattct tattcttccg attg                                              24

<210> SEQ ID NO 61
<211> LENGTH: 20
<212> TYPE: DNA
<213> ORGANISM: artificial sequence
<220> FEATURE:
<223> OTHER INFORMATION: primer

<400> SEQUENCE: 61
caaccgagga caaccaacag                                                   20

<210> SEQ ID NO 62
<211> LENGTH: 18
<212> TYPE: DNA
<213> ORGANISM: artificial sequence
<220> FEATURE:
<223> OTHER INFORMATION: primer

<400> SEQUENCE: 62
catcatctgc ggcttgtc                                                     18

<210> SEQ ID NO 63
<211> LENGTH: 21
<212> TYPE: DNA
<213> ORGANISM: artificial sequence
<220> FEATURE:
<223> OTHER INFORMATION: primer

<400> SEQUENCE: 63
tgagaagacg aacgagtatt g                                                 21

<210> SEQ ID NO 64
<211> LENGTH: 38
<212> TYPE: DNA
<213> ORGANISM: artificial sequence
<220> FEATURE:
<223> OTHER INFORMATION: primer

<400> SEQUENCE: 64
ccatggctat aaggttcttc ctgcacggca accttctg                               38

<210> SEQ ID NO 65
<211> LENGTH: 22
<212> TYPE: DNA
<213> ORGANISM: artificial sequence
<220> FEATURE:
<223> OTHER INFORMATION: primer

<400> SEQUENCE: 65
gaaccttata gccatggtag ag                                                22

<210> SEQ ID NO 66
<211> LENGTH: 38
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t
```

```
<400> SEQUENCE: 66
ccatggctat aaggttcnnn ctgcacggca accttctg                              38

<210> SEQ ID NO 67
<211> LENGTH: 38
<212> TYPE: DNA
<213> ORGANISM: artificial sequence
<220> FEATURE:
<223> OTHER INFORMATION: primer

<400> SEQUENCE: 67
gcgtctgcac cttactcgac gcaatcatcc aatactcg                              38

<210> SEQ ID NO 68
<211> LENGTH: 22
<212> TYPE: DNA
<213> ORGANISM: artificial sequence
<220> FEATURE:
<223> OTHER INFORMATION: primer

<400> SEQUENCE: 68
gagtaaggtg cagacgcagt ag                                               22

<210> SEQ ID NO 69
<211> LENGTH: 38
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t

<400> SEQUENCE: 69
gcgtctgcac cttactcnnn gcaatcatcc aatactcg                              38

<210> SEQ ID NO 70
<211> LENGTH: 38
<212> TYPE: DNA
<213> ORGANISM: artificial sequence
<220> FEATURE:
<223> OTHER INFORMATION: primer

<400> SEQUENCE: 70
cacgccctgg aagatggccc aatcatcgag ctgctggc                              38

<210> SEQ ID NO 71
<211> LENGTH: 38
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 71
cacgccctgg aagatggcnn natcatcgag ctgctggc                              38

<210> SEQ ID NO 72
<211> LENGTH: 38
<212> TYPE: DNA
<213> ORGANISM: artificial sequence
<220> FEATURE:
<223> OTHER INFORMATION: primer
```

```
<400> SEQUENCE: 72
ctgacacctc ccaagtttgg tgatgagaag cagctggg                              38

<210> SEQ ID NO 73
<211> LENGTH: 19
<212> TYPE: DNA
<213> ORGANISM: artificial sequence
<220> FEATURE:
<223> OTHER INFORMATION: primer

<400> SEQUENCE: 73
aaacttggga ggtgtcagc                                                   19

<210> SEQ ID NO 74
<211> LENGTH: 38
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 74
ctgacacctc ccaagttnn ngatgagaag cagctggg                               38

<210> SEQ ID NO 75
<211> LENGTH: 38
<212> TYPE: DNA
<213> ORGANISM: artificial sequence
<220> FEATURE:
<223> OTHER INFORMATION: primer

<400> SEQUENCE: 75
tctccgtcgc aaccatcgtc tgcggcttgt ctcgctac                              38

<210> SEQ ID NO 76
<211> LENGTH: 18
<212> TYPE: DNA
<213> ORGANISM: artificial sequence
<220> FEATURE:
<223> OTHER INFORMATION: primer

<400> SEQUENCE: 76
gatggttgcg acggagag                                                    18

<210> SEQ ID NO 77
<211> LENGTH: 38
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t

<400> SEQUENCE: 77
tctccgtcgc aaccatcnnn tgcggcttgt ctcgctac                              38

<210> SEQ ID NO 78
<211> LENGTH: 39
<212> TYPE: DNA
<213> ORGANISM: artificial sequence
<220> FEATURE:
```

<223> OTHER INFORMATION: primer

<400> SEQUENCE: 78
gtgaagaatc gaatgagaga ttccaactag ccctcgaag                                    39

<210> SEQ ID NO 79
<211> LENGTH: 19
<212> TYPE: DNA
<213> ORGANISM: artificial sequence
<220> FEATURE:
<223> OTHER INFORMATION: primer

<400> SEQUENCE: 79
ctcattcgat tcttcaccg                                                          19

<210> SEQ ID NO 80
<211> LENGTH: 39
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t

<400> SEQUENCE: 80
gtgaagaatc gaatgagnnn ttccaactag ccctcgaag                                    39

<210> SEQ ID NO 81
<211> LENGTH: 37
<212> TYPE: DNA
<213> ORGANISM: artificial sequence
<220> FEATURE:
<223> OTHER INFORMATION: primer

<400> SEQUENCE: 81
cgccattgtc gccgtcaagc gctcgccccc cgaggcc                                      37

<210> SEQ ID NO 82
<211> LENGTH: 19
<212> TYPE: DNA
<213> ORGANISM: artificial sequence
<220> FEATURE:
<223> OTHER INFORMATION: primer

<400> SEQUENCE: 82
gacggcgaca atggcgatg                                                          19

<210> SEQ ID NO 83
<211> LENGTH: 37
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (17)..(19)
<223> OTHER INFORMATION: n is a, c, g, or t

<400> SEQUENCE: 83
cgccattgtc gccgtcnnnc gctcgccccc cgaggcc                                      37

<210> SEQ ID NO 84
<211> LENGTH: 38
<212> TYPE: DNA
<213> ORGANISM: artificial sequence

```
<220> FEATURE:
<223> OTHER INFORMATION: primer

<400> SEQUENCE: 84
gccttcaaac catgatgcaa tcatggatcc ttccagcc                              38

<210> SEQ ID NO 85
<211> LENGTH: 18
<212> TYPE: DNA
<213> ORGANISM: artificial sequence
<220> FEATURE:
<223> OTHER INFORMATION: primer

<400> SEQUENCE: 85
catcatggtt tgaaggcc                                                   18

<210> SEQ ID NO 86
<211> LENGTH: 38
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t

<400> SEQUENCE: 86
gccttcaaac catgatgnnn tcatggatcc ttccagcc                              38

<210> SEQ ID NO 87
<211> LENGTH: 39
<212> TYPE: DNA
<213> ORGANISM: artificial sequence
<220> FEATURE:
<223> OTHER INFORMATION: primer

<400> SEQUENCE: 87
ggtctcttct tcccgaccca ctggctctcc gtcgcaacc                             39

<210> SEQ ID NO 88
<211> LENGTH: 19
<212> TYPE: DNA
<213> ORGANISM: artificial sequence
<220> FEATURE:
<223> OTHER INFORMATION: primer

<400> SEQUENCE: 88
ggtcgggaag aagagaccc                                                  19

<210> SEQ ID NO 89
<211> LENGTH: 39
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 89
ggtctcttct tcccgaccnn ntggctctcc gtcgcaacc                             39

<210> SEQ ID NO 90
<211> LENGTH: 36
<212> TYPE: DNA
```

```
<213> ORGANISM: artificial sequence
<220> FEATURE:
<223> OTHER INFORMATION: primer

<400> SEQUENCE: 90
tctactgcgt ctgcaccaac ctcgtcgcaa tcatcc                                 36

<210> SEQ ID NO 91
<211> LENGTH: 19
<212> TYPE: DNA
<213> ORGANISM: artificial sequence
<220> FEATURE:
<223> OTHER INFORMATION: primer

<400> SEQUENCE: 91
ggtgcagacg cagtagatc                                                    19

<210> SEQ ID NO 92
<211> LENGTH: 36
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t

<400> SEQUENCE: 92
tctactgcgt ctgcaccnnn ctcgtcgcaa tcatcc                                 36

<210> SEQ ID NO 93
<211> LENGTH: 39
<212> TYPE: DNA
<213> ORGANISM: artificial sequence
<220> FEATURE:
<223> OTHER INFORMATION: primer

<400> SEQUENCE: 93
catgaccgcg agggtctcgg gttcccgacc ttctggctc                              39

<210> SEQ ID NO 94
<211> LENGTH: 18
<212> TYPE: DNA
<213> ORGANISM: artificial sequence
<220> FEATURE:
<223> OTHER INFORMATION: primer

<400> SEQUENCE: 94
gagaccctcg cggtcatg                                                     18

<210> SEQ ID NO 95
<211> LENGTH: 39
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 95
catgaccgcg agggtctcnn nttcccgacc ttctggctc                              39

<210> SEQ ID NO 96
<211> LENGTH: 38
```

```
<212> TYPE: DNA
<213> ORGANISM: artificial sequence
<220> FEATURE:
<223> OTHER INFORMATION: primer

<400> SEQUENCE: 96
caacaacccg ctcgcgcatg tctccccatc atcggcgc                             38

<210> SEQ ID NO 97
<211> LENGTH: 18
<212> TYPE: DNA
<213> ORGANISM: artificial sequence
<220> FEATURE:
<223> OTHER INFORMATION: primer

<400> SEQUENCE: 97
tgcgcgagcg ggttgttg                                                   18

<210> SEQ ID NO 98
<211> LENGTH: 38
<212> TYPE: DNA
<213> ORGANISM: artificial sequence
<220> FEATURE:
<223> OTHER INFORMATION: primer

<400> SEQUENCE: 98
caacaacccg ctcgcgcatg tctccccatc atcggcgc                             38

<210> SEQ ID NO 99
<211> LENGTH: 39
<212> TYPE: DNA
<213> ORGANISM: artificial sequence
<220> FEATURE:
<223> OTHER INFORMATION: primer

<400> SEQUENCE: 99
tctgcggctt gtctcgcatc ttcggtgaag aatcgaatg                            39

<210> SEQ ID NO 100
<211> LENGTH: 19
<212> TYPE: DNA
<213> ORGANISM: artificial sequence
<220> FEATURE:
<223> OTHER INFORMATION: primer

<400> SEQUENCE: 100
gcgagacaag ccgcagatg                                                  19

<210> SEQ ID NO 101
<211> LENGTH: 39
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t

<400> SEQUENCE: 101
tctgcggctt gtctcgcnnn ttcggtgaag aatcgaatg                            39

<210> SEQ ID NO 102
<211> LENGTH: 38
<212> TYPE: DNA
<213> ORGANISM: artificial sequence
<220> FEATURE:
```

<223> OTHER INFORMATION: primer

<400> SEQUENCE: 102
tcagcttcat gatgtacggg cactacatcg gccgactg                                38

<210> SEQ ID NO 103
<211> LENGTH: 19
<212> TYPE: DNA
<213> ORGANISM: artificial sequence
<220> FEATURE:
<223> OTHER INFORMATION: primer

<400> SEQUENCE: 103
gtacatcatg aagctgatg                                                     19

<210> SEQ ID NO 104
<211> LENGTH: 38
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t

<400> SEQUENCE: 104
tcagcttcat gatgtacnnn cactacatcg gccgactg                                38

<210> SEQ ID NO 105
<211> LENGTH: 37
<212> TYPE: DNA
<213> ORGANISM: artificial sequence
<220> FEATURE:
<223> OTHER INFORMATION: primer

<400> SEQUENCE: 105
cggcgccggc gtcaccaagc agggcctcgg cttctcc                                 37

<210> SEQ ID NO 106
<211> LENGTH: 19
<212> TYPE: DNA
<213> ORGANISM: artificial sequence
<220> FEATURE:
<223> OTHER INFORMATION: primer

<400> SEQUENCE: 106
ggtgacgccg gcgccgatg                                                     19

<210> SEQ ID NO 107
<211> LENGTH: 37
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (17)..(19)
<223> OTHER INFORMATION: n is a, c, g, or t

<400> SEQUENCE: 107
cggcgccggc gtcaccnnnc agggcctcgg cttctcc                                 37

<210> SEQ ID NO 108
<211> LENGTH: 39
<212> TYPE: DNA
<213> ORGANISM: artificial sequence

```
<220> FEATURE:
<223> OTHER INFORMATION: primer

<400> SEQUENCE: 108
atggagtccg gcctcccctt cagcgaccac agaccaggc                      39

<210> SEQ ID NO 109
<211> LENGTH: 19
<212> TYPE: DNA
<213> ORGANISM: artificial sequence
<220> FEATURE:
<223> OTHER INFORMATION: primer

<400> SEQUENCE: 109
ggggaggccg gactccatc                                            19

<210> SEQ ID NO 110
<211> LENGTH: 39
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 110
atggagtccg gcctccccnn nagcgaccac agaccaggc                      39

<210> SEQ ID NO 111
<211> LENGTH: 39
<212> TYPE: DNA
<213> ORGANISM: artificial sequence
<220> FEATURE:
<223> OTHER INFORMATION: primer

<400> SEQUENCE: 111
ccctcgccct cgtcggctac agcaaaggcc tccccgaag                      39

<210> SEQ ID NO 112
<211> LENGTH: 18
<212> TYPE: DNA
<213> ORGANISM: artificial sequence
<220> FEATURE:
<223> OTHER INFORMATION: primer

<400> SEQUENCE: 112
gccgacgagg gcgagggc                                             18

<210> SEQ ID NO 113
<211> LENGTH: 39
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t

<400> SEQUENCE: 113
ccctcgccct cgtcggcnnn agcaaaggcc tccccgaag                      39

<210> SEQ ID NO 114
<211> LENGTH: 36
<212> TYPE: DNA
```

```
<213> ORGANISM: artificial sequence
<220> FEATURE:
<223> OTHER INFORMATION: primer

<400> SEQUENCE: 114
tacatcggcc gactgatgca ctccggcctc ccccac                              36

<210> SEQ ID NO 115
<211> LENGTH: 19
<212> TYPE: DNA
<213> ORGANISM: artificial sequence
<220> FEATURE:
<223> OTHER INFORMATION: primer

<400> SEQUENCE: 115
catcagtcgg ccgatgtag                                                 19

<210> SEQ ID NO 116
<211> LENGTH: 36
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 116
tacatcggcc gactgatgnn ntccggcctc ccccac                              36

<210> SEQ ID NO 117
<211> LENGTH: 30
<212> TYPE: DNA
<213> ORGANISM: artificial sequence
<220> FEATURE:
<223> OTHER INFORMATION: primer

<400> SEQUENCE: 117
gggggatcct gtacagcttg cctcgtcccc                                     30

<210> SEQ ID NO 118
<211> LENGTH: 24
<212> TYPE: DNA
<213> ORGANISM: artificial sequence
<220> FEATURE:
<223> OTHER INFORMATION: primer

<400> SEQUENCE: 118
gtcgacactg gatggcggcg ttag                                           24

<210> SEQ ID NO 119
<211> LENGTH: 34
<212> TYPE: DNA
<213> ORGANISM: artificial sequence
<220> FEATURE:
<223> OTHER INFORMATION: primer

<400> SEQUENCE: 119
gggagatctg ttgtaacact ggcagagcat tacg                                34

<210> SEQ ID NO 120
<211> LENGTH: 32
<212> TYPE: DNA
<213> ORGANISM: artificial sequence
<220> FEATURE:
<223> OTHER INFORMATION: primer
```

```
<400> SEQUENCE: 120
gggggatccg tcccagtttc tccatacgaa cc                                     32

<210> SEQ ID NO 121
<211> LENGTH: 34
<212> TYPE: DNA
<213> ORGANISM: artificial sequence
<220> FEATURE:
<223> OTHER INFORMATION: primer

<400> SEQUENCE: 121
gggttcgaaa tggccgcgcc gcaacgccaa cccg                                   34

<210> SEQ ID NO 122
<211> LENGTH: 34
<212> TYPE: DNA
<213> ORGANISM: artificial sequence
<220> FEATURE:
<223> OTHER INFORMATION: primer

<400> SEQUENCE: 122
ggggcggccg ctcatcaggc cttgccgatc ttac                                   34

<210> SEQ ID NO 123
<211> LENGTH: 35
<212> TYPE: DNA
<213> ORGANISM: artificial sequence
<220> FEATURE:
<223> OTHER INFORMATION: primer

<400> SEQUENCE: 123
gggttcgaaa tgcccattag caagatcctc gtggc                                  35

<210> SEQ ID NO 124
<211> LENGTH: 35
<212> TYPE: DNA
<213> ORGANISM: artificial sequence
<220> FEATURE:
<223> OTHER INFORMATION: primer

<400> SEQUENCE: 124
ggggcggccg ctcagccgcc gtagaccgcg aggag                                  35

<210> SEQ ID NO 125
<211> LENGTH: 32
<212> TYPE: DNA
<213> ORGANISM: artificial sequence
<220> FEATURE:
<223> OTHER INFORMATION: primer

<400> SEQUENCE: 125
gggttcgaaa tggcggctcc gtttcgtcag cc                                     32

<210> SEQ ID NO 126
<211> LENGTH: 34
<212> TYPE: DNA
<213> ORGANISM: artificial sequence
<220> FEATURE:
<223> OTHER INFORMATION: primer

<400> SEQUENCE: 126
ggggcggccg cctattacgc tttgacgatc ttgc                                   34

<210> SEQ ID NO 127
```

```
<211> LENGTH: 34
<212> TYPE: DNA
<213> ORGANISM: artificial sequence
<220> FEATURE:
<223> OTHER INFORMATION: primer

<400> SEQUENCE: 127
aattgaacaa ctatttcgaa atgcctgctg cacc                              34

<210> SEQ ID NO 128
<211> LENGTH: 35
<212> TYPE: DNA
<213> ORGANISM: artificial sequence
<220> FEATURE:
<223> OTHER INFORMATION: primer

<400> SEQUENCE: 128
agaaagctgg cggccgctta ggcttcctct ttgac                             35

<210> SEQ ID NO 129
<211> LENGTH: 35
<212> TYPE: DNA
<213> ORGANISM: artificial sequence
<220> FEATURE:
<223> OTHER INFORMATION: primer

<400> SEQUENCE: 129
caattgaaca actatttcga aatgtcgact cacac                             35

<210> SEQ ID NO 130
<211> LENGTH: 34
<212> TYPE: DNA
<213> ORGANISM: artificial sequence
<220> FEATURE:
<223> OTHER INFORMATION: primer

<400> SEQUENCE: 130
ctagaaagct ggcggccgcc tattaggaaa cgac                              34

<210> SEQ ID NO 131
<211> LENGTH: 34
<212> TYPE: DNA
<213> ORGANISM: artificial sequence
<220> FEATURE:
<223> OTHER INFORMATION: primer

<400> SEQUENCE: 131
gggttcgaaa tggccgaaga agactactcc ccgc                              34

<210> SEQ ID NO 132
<211> LENGTH: 35
<212> TYPE: DNA
<213> ORGANISM: artificial sequence
<220> FEATURE:
<223> OTHER INFORMATION: primer

<400> SEQUENCE: 132
ggggcggccg cttactcagc cttgacgatt ttggc                             35

<210> SEQ ID NO 133
<211> LENGTH: 26
<212> TYPE: DNA
<213> ORGANISM: artificial sequence
<220> FEATURE:
<223> OTHER INFORMATION: primer

<400> SEQUENCE: 133
```

```
tgggccttgc ggatcgtttc gagctc                                    26

<210> SEQ ID NO 134
<211> LENGTH: 27
<212> TYPE: DNA
<213> ORGANISM: artificial sequence
<220> FEATURE:
<223> OTHER INFORMATION: primer

<400> SEQUENCE: 134
acgatccgca aggcccagtg cggtggc                                   27

<210> SEQ ID NO 135
<211> LENGTH: 20
<212> TYPE: DNA
<213> ORGANISM: artificial sequence
<220> FEATURE:
<223> OTHER INFORMATION: primer

<400> SEQUENCE: 135
tgctgcttcg cggtcgcaac                                           20

<210> SEQ ID NO 136
<211> LENGTH: 23
<212> TYPE: DNA
<213> ORGANISM: artificial sequence
<220> FEATURE:
<223> OTHER INFORMATION: primer

<400> SEQUENCE: 136
cgaagcagca tctgaatgtt tac                                       23

<210> SEQ ID NO 137
<211> LENGTH: 29
<212> TYPE: DNA
<213> ORGANISM: artificial sequence
<220> FEATURE:
<223> OTHER INFORMATION: primer

<400> SEQUENCE: 137
gggttcgaaa tgtcgactca cacatcttc                                 29

<210> SEQ ID NO 138
<211> LENGTH: 33
<212> TYPE: DNA
<213> ORGANISM: artificial sequence
<220> FEATURE:
<223> OTHER INFORMATION: primer

<400> SEQUENCE: 138
ggggcggccg cttaggaaac gacgacgatc aag                            33

<210> SEQ ID NO 139
<211> LENGTH: 37
<212> TYPE: DNA
<213> ORGANISM: artificial sequence
<220> FEATURE:
<223> OTHER INFORMATION: primer

<400> SEQUENCE: 139
gaagatcggg gatcattcga gcgctctttt gcttctg                        37

<210> SEQ ID NO 140
<211> LENGTH: 18
<212> TYPE: DNA
```

```
<213> ORGANISM: artificial sequence
<220> FEATURE:
<223> OTHER INFORMATION: primer

<400> SEQUENCE: 140
gaatgatccc cgatcttc                                                   18

<210> SEQ ID NO 141
<211> LENGTH: 37
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 141
gaagatcggg gatcattcnn ncgctctttt gcttctg                              37

<210> SEQ ID NO 142
<211> LENGTH: 38
<212> TYPE: DNA
<213> ORGANISM: artificial sequence
<220> FEATURE:
<223> OTHER INFORMATION: primer

<400> SEQUENCE: 142
agcgcatcgc caccggacaa attgccgatc acccgcac                             38

<210> SEQ ID NO 143
<211> LENGTH: 19
<212> TYPE: DNA
<213> ORGANISM: artificial sequence
<220> FEATURE:
<223> OTHER INFORMATION: primer

<400> SEQUENCE: 143
tccggtggcg atgcgcttg                                                  19

<210> SEQ ID NO 144
<211> LENGTH: 38
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (18)..(20)
<223> OTHER INFORMATION: n is a, c, g, or t

<400> SEQUENCE: 144
agcgcatcgc caccggannn attgccgatc acccgcac                             38

<210> SEQ ID NO 145
<211> LENGTH: 38
<212> TYPE: DNA
<213> ORGANISM: artificial sequence
<220> FEATURE:
<223> OTHER INFORMATION: primer

<400> SEQUENCE: 145
agttgtcgaa attgcgccaa accagcattt ggatccag                             38

<210> SEQ ID NO 146
<211> LENGTH: 18
```

```
<212> TYPE: DNA
<213> ORGANISM: artificial sequence
<220> FEATURE:
<223> OTHER INFORMATION: primer

<400> SEQUENCE: 146
tggcgcaatt tcgacaac                                                       18

<210> SEQ ID NO 147
<211> LENGTH: 38
<212> TYPE: DNA
<213> ORGANISM: artificial sequence
<220> FEATURE:
<223> OTHER INFORMATION: primer

<400> SEQUENCE: 147
agttgtcgaa attgcgccaa accagcattt ggatccag                                 38

<210> SEQ ID NO 148
<211> LENGTH: 39
<212> TYPE: DNA
<213> ORGANISM: artificial sequence
<220> FEATURE:
<223> OTHER INFORMATION: primer

<400> SEQUENCE: 148
taccgccacg aaatcccaat gggacagttg tccaacctg                                39

<210> SEQ ID NO 149
<211> LENGTH: 19
<212> TYPE: DNA
<213> ORGANISM: artificial sequence
<220> FEATURE:
<223> OTHER INFORMATION: primer

<400> SEQUENCE: 149
tgggatttcg tggcggtag                                                      19

<210> SEQ ID NO 150
<211> LENGTH: 39
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (19)..(21)
<223> OTHER INFORMATION: n is a, c, g, or t

<400> SEQUENCE: 150
taccgccacg aaatcccann nggacagttg tccaacctg                                39

<210> SEQ ID NO 151
<211> LENGTH: 35
<212> TYPE: DNA
<213> ORGANISM: artificial sequence
<220> FEATURE:
<223> OTHER INFORMATION: primer

<400> SEQUENCE: 151
gctcaagctg gtaccgatgc tgttgacggt gcttc                                    35

<210> SEQ ID NO 152
<211> LENGTH: 18
<212> TYPE: DNA
<213> ORGANISM: artificial sequence
<220> FEATURE:
```

<223> OTHER INFORMATION: primer

<400> SEQUENCE: 152
accagcttga gctgcagc　　　　　　　　　　　　　　　　　　　　　　　　　　18

<210> SEQ ID NO 153
<211> LENGTH: 35
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (13)..(15)
<223> OTHER INFORMATION: n is a, c, g, or t

<400> SEQUENCE: 153
gctcaagctg gtnnngatgc tgttgacggt gcttc　　　　　　　　　　　　　　　　35

<210> SEQ ID NO 154
<211> LENGTH: 32
<212> TYPE: DNA
<213> ORGANISM: artificial sequence
<220> FEATURE:
<223> OTHER INFORMATION: primer

<400> SEQUENCE: 154
ttgagtctgg aaccttgggc ccaaccggtc gc　　　　　　　　　　　　　　　　　32

<210> SEQ ID NO 155
<211> LENGTH: 22
<212> TYPE: DNA
<213> ORGANISM: artificial sequence
<220> FEATURE:
<223> OTHER INFORMATION: primer

<400> SEQUENCE: 155
ggttccagac tcaaatggca gg　　　　　　　　　　　　　　　　　　　　　22

<210> SEQ ID NO 156
<211> LENGTH: 32
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(17)
<223> OTHER INFORMATION: n is a, c, g, or t

<400> SEQUENCE: 156
ttgagtctgg aaccnnnggc ccaaccggtc gc　　　　　　　　　　　　　　　　32

<210> SEQ ID NO 157
<211> LENGTH: 32
<212> TYPE: DNA
<213> ORGANISM: artificial sequence
<220> FEATURE:
<223> OTHER INFORMATION: primer

<400> SEQUENCE: 157
ctggaacccc aggcaccacc ggtcgcgtct ac　　　　　　　　　　　　　　　　32

<210> SEQ ID NO 158
<211> LENGTH: 18
<212> TYPE: DNA
<213> ORGANISM: artificial sequence

```
<220> FEATURE:
<223> OTHER INFORMATION: primer

<400> SEQUENCE: 158
gcctggggtt ccagactc                                                   18

<210> SEQ ID NO 159
<211> LENGTH: 32
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (15)..(17)
<223> OTHER INFORMATION: n is a, c, g, or t

<400> SEQUENCE: 159
ctggaacccc aggcnnnacc ggtcgcgtct ac                                   32

<210> SEQ ID NO 160
<211> LENGTH: 32
<212> TYPE: DNA
<213> ORGANISM: artificial sequence
<220> FEATURE:
<223> OTHER INFORMATION: primer

<400> SEQUENCE: 160
tgcgatctct gagtccgacg ataagggtat gc                                   32

<210> SEQ ID NO 161
<211> LENGTH: 20
<212> TYPE: DNA
<213> ORGANISM: artificial sequence
<220> FEATURE:
<223> OTHER INFORMATION: primer

<400> SEQUENCE: 161
ctcagagatc gcatccaggc                                                 20

<210> SEQ ID NO 162
<211> LENGTH: 32
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (14)..(16)
<223> OTHER INFORMATION: n is a, c, g, or t

<400> SEQUENCE: 162
tgcgatctct gagnnngacg ataagggtat gc                                   32

<210> SEQ ID NO 163
<211> LENGTH: 57
<212> TYPE: DNA
<213> ORGANISM: artificial sequence
<220> FEATURE:
<223> OTHER INFORMATION: primer

<400> SEQUENCE: 163
caactagtgg atcccccggg ctgcaggaat tcatgagcag tagcaagaaa ttggccg        57

<210> SEQ ID NO 164
<211> LENGTH: 68
<212> TYPE: DNA
```

```
<213> ORGANISM: artificial sequence
<220> FEATURE:
<223> OTHER INFORMATION: primer

<400> SEQUENCE: 164
ctcaacgtca ccgcaagtaa gcaaagaacc tctaccctca gctctctttt tttgggatgg      60
gggtaggg                                                              68

<210> SEQ ID NO 165
<211> LENGTH: 66
<212> TYPE: DNA
<213> ORGANISM: artificial sequence
<220> FEATURE:
<223> OTHER INFORMATION: primer

<400> SEQUENCE: 165
ctttgcttac ttgcggtgac gttgaggaaa acccaggtcc aatgctgaca cctcccaagt      60
ttgagg                                                                66

<210> SEQ ID NO 166
<211> LENGTH: 64
<212> TYPE: DNA
<213> ORGANISM: artificial sequence
<220> FEATURE:
<223> OTHER INFORMATION: primer

<400> SEQUENCE: 166
catctccgca ggtcaaaagg gatccacgtc cttcggcacg atcagataca tcctcatctt      60
tacc                                                                  64

<210> SEQ ID NO 167
<211> LENGTH: 76
<212> TYPE: DNA
<213> ORGANISM: artificial sequence
<220> FEATURE:
<223> OTHER INFORMATION: primer

<400> SEQUENCE: 167
gacgtggatc cctttttgacc tgcggagatg tcgaagagaa tcctggacct atggtcaaag     60
tcgcaattct tggcgc                                                     76

<210> SEQ ID NO 168
<211> LENGTH: 57
<212> TYPE: DNA
<213> ORGANISM: artificial sequence
<220> FEATURE:
<223> OTHER INFORMATION: primer

<400> SEQUENCE: 168
cccctcgagg tcgacggtat cgataagctt tcaagagtct aggatgaaac tcttgcc         57

<210> SEQ ID NO 169
<211> LENGTH: 65
<212> TYPE: DNA
<213> ORGANISM: artificial sequence
<220> FEATURE:
<223> OTHER INFORMATION: primer

<400> SEQUENCE: 169
ggaagatctt aattaactcg agcggccgcg tttaaacact agtatgctga cacctcccaa     60
gtttg                                                                 65
```

```
<210> SEQ ID NO 170
<211> LENGTH: 28
<212> TYPE: DNA
<213> ORGANISM: artificial sequence
<220> FEATURE:
<223> OTHER INFORMATION: primer

<400> SEQUENCE: 170
atcctaatca gatacatcct catcttta                                        28

<210> SEQ ID NO 171
<211> LENGTH: 33
<212> TYPE: DNA
<213> ORGANISM: artificial sequence
<220> FEATURE:
<223> OTHER INFORMATION: primer

<400> SEQUENCE: 171
ccttaattaa catgtacctt gacgtcctcc gag                                  33

<210> SEQ ID NO 172
<211> LENGTH: 31
<212> TYPE: DNA
<213> ORGANISM: artificial sequence
<220> FEATURE:
<223> OTHER INFORMATION: primer

<400> SEQUENCE: 172
ggactagttc tgaagaacga aactggcgac t                                    31

<210> SEQ ID NO 173
<211> LENGTH: 29
<212> TYPE: DNA
<213> ORGANISM: artificial sequence
<220> FEATURE:
<223> OTHER INFORMATION: primer

<400> SEQUENCE: 173
ggactagtat gtcgactcac acatcttca                                       29

<210> SEQ ID NO 174
<211> LENGTH: 33
<212> TYPE: DNA
<213> ORGANISM: artificial sequence
<220> FEATURE:
<223> OTHER INFORMATION: primer

<400> SEQUENCE: 174
aaaaagatat cttaggaaac gacgacgatc aag                                  33

<210> SEQ ID NO 175
<211> LENGTH: 1140
<212> TYPE: PRT
<213> ORGANISM: artificial sequence
<220> FEATURE:
<223> OTHER INFORMATION: mutant protein
<220> FEATURE:
<221> NAME/KEY: misc_feature
<222> LOCATION: (51)..(51)
<223> OTHER INFORMATION: Xaa=N, or G
<220> FEATURE:
<221> NAME/KEY: misc_feature
<222> LOCATION: (254)..(254)
<223> OTHER INFORMATION: Xaa=K, E, R, or F
<220> FEATURE:
<221> NAME/KEY: misc_feature
<222> LOCATION: (453)..(453)
<223> OTHER INFORMATION: Xaa=E, or P
<220> FEATURE:
```

```
<221> NAME/KEY: misc_feature
<222> LOCATION: (762)..(762)
<223> OTHER INFORMATION: Xaa=D, P, V, or T
<220> FEATURE:
<221> NAME/KEY: misc_feature
<222> LOCATION: (824)..(824)
<223> OTHER INFORMATION: Xaa=V, A, I, Y, L, M, N, R, or T
<220> FEATURE:
<221> NAME/KEY: misc_feature
<222> LOCATION: (826)..(826)
<223> OTHER INFORMATION: Xaa=E, Q, Y, T, D, or I
<220> FEATURE:
<221> NAME/KEY: misc_feature
<222> LOCATION: (837)..(837)
<223> OTHER INFORMATION: Xaa=D, or H
<220> FEATURE:
<221> NAME/KEY: misc_feature
<222> LOCATION: (1031)..(1031)
<223> OTHER INFORMATION: Xaa=E, N, S, or G

<400> SEQUENCE: 175
```

| | | | | | | | | | | | | | | |
|---|---|---|---|---|---|---|---|---|---|---|---|---|---|---|
| Met | Ser | Thr | His | Thr | Ser | Ser | Thr | Leu | Pro | Ala | Phe | Lys | Lys | Ile | Leu |
| 1 | | | | 5 | | | | | 10 | | | | | 15 | |
| Val | Ala | Asn | Arg | Gly | Glu | Ile | Ala | Val | Arg | Ala | Phe | Arg | Ala | Ala | Leu |
| | | | 20 | | | | | 25 | | | | | 30 | | |
| Glu | Thr | Gly | Ala | Ala | Thr | Val | Ala | Ile | Tyr | Pro | Arg | Glu | Asp | Arg | Gly |
| | | 35 | | | | | 40 | | | | | 45 | | | |
| Ser | Phe | Xaa | Arg | Ser | Phe | Ala | Ser | Glu | Ala | Val | Arg | Ile | Gly | Thr | Glu |
| | 50 | | | | | 55 | | | | | 60 | | | | |
| Gly | Ser | Pro | Val | Lys | Ala | Tyr | Leu | Asp | Ile | Asp | Glu | Ile | Ile | Gly | Ala |
| 65 | | | | | 70 | | | | | 75 | | | | | 80 |
| Ala | Lys | Lys | Val | Lys | Ala | Asp | Ala | Ile | Tyr | Pro | Gly | Tyr | Gly | Phe | Leu |
| | | | | 85 | | | | | 90 | | | | | 95 | |
| Ser | Glu | Asn | Ala | Gln | Leu | Ala | Arg | Glu | Cys | Ala | Glu | Asn | Gly | Ile | Thr |
| | | | 100 | | | | | 105 | | | | | 110 | | |
| Phe | Ile | Gly | Pro | Thr | Pro | Glu | Val | Leu | Asp | Leu | Thr | Gly | Asp | Lys | Ser |
| | | 115 | | | | | 120 | | | | | 125 | | | |
| Arg | Ala | Val | Thr | Ala | Ala | Lys | Lys | Ala | Gly | Leu | Pro | Val | Leu | Ala | Glu |
| | 130 | | | | | 135 | | | | | 140 | | | | |
| Ser | Thr | Pro | Ser | Lys | Asn | Ile | Asp | Glu | Ile | Val | Lys | Ser | Ala | Glu | Gly |
| 145 | | | | | 150 | | | | | 155 | | | | | 160 |
| Gln | Thr | Tyr | Pro | Ile | Phe | Val | Lys | Ala | Val | Ala | Gly | Gly | Gly | Arg |
| | | | | 165 | | | | | 170 | | | | | 175 |
| Gly | Met | Arg | Phe | Val | Ala | Ser | Pro | Asp | Glu | Leu | Arg | Lys | Leu | Ala | Thr |
| | | | 180 | | | | | 185 | | | | | 190 | | |
| Glu | Ala | Ser | Arg | Glu | Ala | Glu | Ala | Ala | Phe | Gly | Asp | Gly | Ala | Val | Tyr |
| | | 195 | | | | | 200 | | | | | 205 | | | |
| Val | Glu | Arg | Ala | Val | Ile | Asn | Pro | Gln | His | Ile | Glu | Val | Gln | Ile | Leu |
| | 210 | | | | | 215 | | | | | 220 | | | | |
| Gly | Asp | His | Thr | Gly | Glu | Val | Val | His | Leu | Tyr | Glu | Arg | Asp | Cys | Ser |
| 225 | | | | | 230 | | | | | 235 | | | | | 240 |
| Leu | Gln | Arg | Arg | His | Gln | Lys | Val | Val | Glu | Ile | Ala | Pro | Xaa | Gln | His |
| | | | | 245 | | | | | 250 | | | | | 255 | |
| Leu | Asp | Pro | Glu | Leu | Arg | Asp | Arg | Ile | Cys | Ala | Asp | Ala | Val | Lys | Phe |
| | | | 260 | | | | | 265 | | | | | 270 | | |
| Cys | Arg | Ser | Ile | Gly | Tyr | Gln | Gly | Ala | Gly | Thr | Val | Glu | Phe | Leu | Val |
| | | 275 | | | | | 280 | | | | | 285 | | | |
| Asp | Glu | Lys | Gly | Asn | His | Val | Phe | Ile | Glu | Met | Asn | Pro | Arg | Ile | Gln |
| | 290 | | | | | 295 | | | | | 300 | | | | |

```
Val Glu His Thr Val Thr Glu Glu Val Thr Glu Val Asp Leu Val Lys
305                 310                 315                 320

Ala Gln Met Arg Leu Ala Ala Gly Ala Thr Lys Glu Leu Gly Leu
            325                 330                 335

Thr Gln Asp Lys Ile Lys Thr His Gly Ala Ala Leu Gln Cys Arg Ile
                340                 345                 350

Thr Thr Glu Asp Pro Asn Asn Gly Phe Arg Pro Asp Thr Gly Thr Ile
                355                 360                 365

Thr Ala Tyr Arg Ser Pro Gly Ala Gly Val Arg Leu Asp Gly Ala
            370                 375                 380

Ala Gln Leu Gly Gly Glu Ile Thr Ala His Phe Asp Ser Met Leu Val
385                 390                 395                 400

Lys Met Thr Cys Arg Gly Ser Asp Phe Glu Thr Ala Val Ala Arg Ala
                405                 410                 415

Gln Arg Ala Leu Ala Glu Phe Thr Val Ser Gly Val Ala Thr Asn Ile
                420                 425                 430

Gly Phe Leu Arg Ala Leu Leu Arg Glu Glu Asp Phe Thr Ser Lys Arg
                435                 440                 445

Ile Ala Thr Gly Xaa Ile Ala Asp His Pro His Leu Leu Gln Ala Pro
                450                 455                 460

Pro Ala Asp Asp Glu Gln Gly Arg Ile Leu Asp Tyr Leu Ala Asp Val
465                 470                 475                 480

Thr Val Asn Lys Pro His Gly Val Arg Pro Lys Asp Val Ala Ala Pro
                485                 490                 495

Ile Asp Lys Leu Pro Asn Ile Lys Asp Leu Pro Leu Pro Arg Gly Ser
                500                 505                 510

Arg Asp Arg Leu Lys Gln Leu Gly Pro Ala Ala Phe Ala Arg Asp Leu
                515                 520                 525

Arg Glu Gln Asp Ala Leu Ala Val Thr Asp Thr Thr Phe Arg Asp Ala
                530                 535                 540

His Gln Ser Leu Leu Ala Thr Arg Val Arg Ser Phe Ala Leu Lys Pro
545                 550                 555                 560

Ala Ala Glu Ala Val Ala Lys Leu Thr Pro Glu Leu Leu Ser Val Glu
                565                 570                 575

Ala Trp Gly Gly Ala Thr Tyr Asp Val Ala Met Arg Phe Leu Phe Glu
                580                 585                 590

Asp Pro Trp Asp Arg Leu Asp Glu Leu Arg Glu Ala Met Pro Asn Val
                595                 600                 605

Asn Ile Gln Met Leu Leu Arg Gly Arg Asn Thr Val Gly Tyr Thr Pro
610                 615                 620

Tyr Pro Asp Ser Val Cys Arg Ala Phe Val Lys Glu Ala Ala Ser Ser
625                 630                 635                 640

Gly Val Asp Ile Phe Arg Ile Phe Asp Ala Leu Asn Asp Val Ser Gln
                645                 650                 655

Met Arg Pro Ala Ile Asp Ala Val Leu Glu Thr Asn Thr Ala Val Ala
                660                 665                 670

Glu Val Ala Met Ala Tyr Ser Gly Asp Leu Ser Asp Pro Asn Glu Lys
                675                 680                 685

Leu Tyr Thr Leu Asp Tyr Tyr Leu Lys Met Ala Glu Glu Ile Val Lys
                690                 695                 700

Ser Gly Ala His Ile Leu Ala Ile Lys Asp Met Ala Gly Leu Leu Arg
705                 710                 715                 720

Pro Ala Ala Val Thr Lys Leu Val Thr Ala Leu Arg Arg Glu Phe Asp
```

-continued

```
                725                 730                 735
Leu Pro Val His Val His Thr His Asp Thr Ala Gly Gly Gln Leu Ala
            740                 745                 750
Thr Tyr Phe Ala Ala Ala Gln Ala Gly Xaa Asp Ala Val Asp Gly Ala
            755                 760                 765
Ser Ala Pro Leu Ser Gly Thr Thr Ser Gln Pro Ser Leu Ser Ala Ile
770                 775                 780
Val Ala Ala Phe Ala His Thr Arg Arg Asp Thr Gly Leu Ser Leu Glu
785                 790                 795                 800
Ala Val Ser Asp Leu Glu Pro Tyr Trp Glu Ala Val Arg Gly Leu Tyr
            805                 810                 815
Leu Pro Phe Glu Ser Gly Thr Pro Gly Xaa Thr Gly Arg Val Tyr Arg
            820                 825                 830
His Glu Ile Pro Xaa Gly Gln Leu Ser Asn Leu Arg Ala Gln Ala Thr
            835                 840                 845
Ala Leu Gly Leu Ala Asp Arg Phe Glu Leu Ile Glu Asp Asn Tyr Ala
850                 855                 860
Ala Val Asn Glu Met Leu Gly Arg Pro Thr Lys Val Thr Pro Ser Ser
865                 870                 875                 880
Lys Val Val Gly Asp Leu Ala Leu His Leu Val Gly Ala Gly Val Asp
                885                 890                 895
Pro Ala Asp Phe Ala Ala Asp Pro Gln Lys Tyr Asp Ile Pro Asp Ser
            900                 905                 910
Val Ile Ala Phe Leu Arg Gly Glu Leu Gly Asn Pro Pro Gly Gly Trp
            915                 920                 925
Pro Glu Pro Leu Arg Thr Arg Ala Leu Glu Gly Arg Ser Glu Gly Lys
            930                 935                 940
Ala Pro Leu Thr Glu Val Pro Glu Glu Gln Ala His Leu Asp Ala
945                 950                 955                 960
Asp Asp Ser Lys Glu Arg Arg Asn Ser Leu Asn Arg Leu Leu Phe Pro
                965                 970                 975
Lys Pro Thr Glu Glu Phe Leu Glu His Arg Arg Arg Phe Gly Asn Thr
            980                 985                 990
Ser Ala Leu Asp Asp Arg Glu Phe  Phe Tyr Gly Leu Val  Glu Gly Arg
            995                 1000               1005
Glu Thr Leu Ile Arg Leu Pro Asp Val Arg Thr Pro  Leu Leu Val
    1010               1015                1020
Arg Leu Asp Ala Ile Ser Glu  Xaa Asp Asp Lys Gly  Met Arg Asn
    1025                1030                1035
Val Val  Ala Asn Val Asn Gly  Gln Ile Arg Pro Met  Arg Val Arg
    1040                1045                1050
Asp Arg Ser Val Glu Ser Val  Thr Ala Thr Ala Glu  Lys Ala Asp
    1055                1060                1065
Ser Ser Asn Lys Gly His Val  Ala Ala Pro Phe Ala  Gly Val Val
    1070                1075                1080
Thr Val  Thr Val Ala Glu Gly  Asp Glu Val Lys Ala  Gly Asp Ala
    1085                1090                1095
Val Ala  Ile Ile Glu Ala Met  Lys Met Glu Ala Thr  Ile Thr Ala
    1100                1105                1110
Ser Val  Asp Gly Lys Ile Asp  Arg Val Val Val Pro  Ala Ala Thr
    1115                1120                1125
Lys Val  Glu Gly Gly Asp Leu  Ile Val Val Val Ser
    1130                1135                1140
```

```
<210> SEQ ID NO 176
<211> LENGTH: 380
<212> TYPE: PRT
<213> ORGANISM: artificial sequence
<220> FEATURE:
<223> OTHER INFORMATION: mutant protein
<220> FEATURE:
<221> NAME/KEY: misc_feature
<222> LOCATION: (8)..(8)
<223> OTHER INFORMATION: Xaa=Q, Y, R, or P
<220> FEATURE:
<221> NAME/KEY: misc_feature
<222> LOCATION: (80)..(80)
<223> OTHER INFORMATION: Xaa=K, W, or C
<220> FEATURE:
<221> NAME/KEY: misc_feature
<222> LOCATION: (97)..(97)
<223> OTHER INFORMATION: Xaa=V, or R
<220> FEATURE:
<221> NAME/KEY: misc_feature
<222> LOCATION: (101)..(101)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa=E, or L
<220> FEATURE:
<221> NAME/KEY: misc_feature
<222> LOCATION: (123)..(123)
<223> OTHER INFORMATION: Xaa=K, H, R, or D
<220> FEATURE:
<221> NAME/KEY: misc_feature
<222> LOCATION: (140)..(140)
<223> OTHER INFORMATION: Xaa=N, K, or H
<220> FEATURE:
<221> NAME/KEY: misc_feature
<222> LOCATION: (142)..(142)
<223> OTHER INFORMATION: Xaa=I, S, or C
<220> FEATURE:
<221> NAME/KEY: misc_feature
<222> LOCATION: (163)..(163)
<223> OTHER INFORMATION: Xaa=I, V, F, L, Q, or Y
<220> FEATURE:
<221> NAME/KEY: misc_feature
<222> LOCATION: (191)..(191)
<223> OTHER INFORMATION: Xaa=R, or K
<220> FEATURE:
<221> NAME/KEY: misc_feature
<222> LOCATION: (201)..(201)
<223> OTHER INFORMATION: Xaa=Q, G, N, or K
<220> FEATURE:
<221> NAME/KEY: misc_feature
<222> LOCATION: (222)..(222)
<223> OTHER INFORMATION: Xaa=S, or H
<220> FEATURE:
<221> NAME/KEY: misc_feature
<222> LOCATION: (227)..(227)
<223> OTHER INFORMATION: Xaa can be any naturally occurring amino acid
<220> FEATURE:
<221> NAME/KEY: misc_feature
<222> LOCATION: (251)..(251)
<223> OTHER INFORMATION: Xaa=E, or G
<220> FEATURE:
<221> NAME/KEY: misc_feature
<222> LOCATION: (272)..(272)
<223> OTHER INFORMATION: Xaa=A, or F
<220> FEATURE:
<221> NAME/KEY: misc_feature
<222> LOCATION: (301)..(301)
<223> OTHER INFORMATION: Xaa=W, F, H, K, or Y

<400> SEQUENCE: 176
```

```
Met Leu Thr Pro Pro Lys Phe Xaa Asp Glu Lys Gln Leu Gly Pro Val
1               5                   10                  15

Gly Ile Arg Glu Arg Leu Arg His Phe Thr Trp Ala Trp Tyr Thr Leu
            20                  25                  30

Thr Met Ser Gly Gly Gly Leu Ala Val Leu Ile Ile Ser Gln Pro Phe
        35                  40                  45

Gly Phe Arg Gly Leu Arg Glu Ile Gly Ile Ala Val Tyr Ile Leu Asn
    50                  55                  60

Leu Ile Leu Phe Ala Leu Val Cys Ser Thr Met Ala Ile Arg Phe Xaa
65                  70                  75                  80

Leu His Gly Asn Leu Leu Glu Ser Leu Arg His Asp Arg Glu Gly Leu
                85                  90                  95

Xaa Phe Pro Thr Xaa Trp Leu Ser Val Ala Thr Ile Xaa Cys Gly Leu
                100                 105                 110

Ser Arg Xaa Phe Gly Glu Glu Ser Asn Glu Xaa Phe Gln Leu Ala Leu
            115                 120                 125

Glu Ala Leu Phe Trp Ile Tyr Cys Val Cys Thr Xaa Leu Xaa Ala Ile
        130                 135                 140

Ile Gln Tyr Ser Phe Val Phe Ser Ser His Lys Tyr Gly Leu Gln Thr
145                 150                 155                 160

Met Met Xaa Ser Trp Ile Leu Pro Ala Phe Pro Ile Met Leu Ser Gly
            165                 170                 175

Thr Ile Ala Ser Val Ile Gly Glu Gln Gln Pro Ala Arg Ala Xaa Leu
            180                 185                 190

Pro Ile Ile Gly Ala Gly Val Thr Xaa Gln Gly Leu Gly Phe Ser Ile
    195                 200                 205

Ser Phe Met Met Tyr Ala His Tyr Ile Gly Arg Leu Met Xaa Ser Gly
    210                 215                 220

Leu Pro Xaa Ser Asp His Arg Pro Gly Met Phe Ile Cys Val Gly Pro
225                 230                 235                 240

Pro Ala Phe Thr Ala Leu Ala Leu Val Gly Xaa Ser Lys Gly Leu Pro
            245                 250                 255

Glu Asp Phe Lys Leu Leu His Asp Ala His Ala Leu Glu Asp Gly Xaa
            260                 265                 270

Ile Ile Glu Leu Leu Ala Ile Ser Ala Gly Val Phe Leu Trp Ala Leu
            275                 280                 285

Ser Leu Trp Phe Phe Cys Ile Ala Ile Val Ala Val Xaa Arg Ser Pro
    290                 295                 300

Pro Glu Ala Phe His Leu Asn Trp Trp Ala Met Val Phe Pro Asn Thr
305                 310                 315                 320

Gly Phe Thr Leu Ala Thr Ile Thr Leu Gly Lys Ala Leu Asn Ser Asn
            325                 330                 335

Gly Val Lys Gly Val Gly Ser Ala Met Ser Ile Cys Ile Val Cys Met
            340                 345                 350

Tyr Ile Phe Val Phe Val Asn Asn Val Arg Ala Val Ile Arg Lys Asp
            355                 360                 365

Ile Met Tyr Pro Gly Lys Asp Glu Asp Val Ser Asp
            370                 375                 380
```

MUTANT PROTEIN FOR IMPROVING MALIC ACID YIELD

CROSS REFERENCE TO RELATED APPLICATIONS

The present application is the U.S. National Phase under 35 U.S.C. § 371 of International Application No. PCT/CN2019/112010, filed Oct. 18, 2019 which claims the priority of the Chinese patent application filed with the Chinese Patent Office on Oct. 19, 2018, with the application number CN201811223531.1 and the invention title of "New mutant protein for improving malic acid yield", the entire contents of each of which are herein incorporated in the present application by reference.

INCORPORATION OF SEQUENCE LISTING

A Sequence Listing submitted on Apr. 19, 2021 as an ASCII text file via EFS-Web is hereby incorporated by reference in accordance with 35 U.S.C. § 1.52 (e). The name of the ASCII text file for the Sequence Listing is P2020-1016-xlb.TXT, and the size of the ASCII text file is 313,596 bytes.

TECHNICAL FIELD

The present invention belongs to the field of biotechnology. Specifically, the present invention relates to a novel mutant protein of pyruvate carboxylase and malate transporter in the malate synthesis pathway and the uses thereof.

BACKGROUND

Malic acid (2-hydroxy-1,4-succinic acid) is an important platform compound and is widely used in the pharmaceutical, cosmetic, food and beverage industries. In the past, the synthesis was mainly based on chemical methods. However, these processes mainly produced a mixture of D- and L-malic acid, which was difficult to separate.

There are currently five main routes reported for malate synthesis, namely TCA cycle, reduced TCA (or reverse TCA) or rTCA, cyclic glyoxylic acid cycle and non-cyclic glyoxylic acid cycle, and reverse catalyzation of pyruvate into malic acid via malic enzyme. Among them, the rTCA cycle and the malic enzyme pathway are the most effective. The theoretical conversion rate of glucose to malic acid is 2. However, malic enzyme mainly catalyzes the decomposition of malic acid into pyruvate. Therefore, the most common method is the rTCA pathway for synthesizing malic acid.

Starting from glucose, it is converted into pyruvate by glycolysis, and pyruvate is converted into oxaloacetate by pyruvate carboxylase, and oxaloacetate is converted into malate by malate dehydrogenase. Malate is transported out of cell by a transporter. The conversion efficiency of each step in the process, the side reaction diversion, the coenzyme that catalyzes each step of the reaction, and reducibility and the energy state of cells will all affect the synthesis of malic acid.

There are three key indicators in the synthesis of malic acid, namely output, production capacity and conversion rate. In order to construct efficient malic acid production strains, people have constructed malic acid synthesis pathways in many species, such as *Saccharomyces cerevisiae, Pichia pastoris, Escherichia coli, Aspergillus* spp., *Torulopsis glabrata, Ustilago trichophora, Bacillus subtilis* and *Thermobifida fusca*, etc. (Dai. et. al., Current advance in biological production of malic acid using wild type and metabolic engineered strains. Bioresour Technol. 2018, 258: 345-353; Liu et al., Biological production of L-malate: recent advances and future prospects. *World J Microbiol Biotechnol.* 2017, 34(1):6). However, these works mainly tried to construct malate synthesis pathways and performed partial optimization in different species. For example, promoters with different strengths were used to express key enzymes in malate synthesis to enhance malate synthesis ability, but this requires a multi-round combination process. Further, overexpression of synthetic key enzymes also causes additional burden on cells.

Therefore, there is an urgent need in the art to develop a method for obtaining pure malic acid directly and efficiently.

SUMMARY OF THE INVENTION

The present invention provides a novel mutant protein of pyruvate carboxylase and malate transporter in the malate synthesis pathway and uses thereof.

In the first aspect of the present invention, it provides a pyruvate carboxylase mutant protein which, based on a sequence as shown in SEQ ID NO: 1 (wild-type), has one or more core amino acid mutations selected from the group consisting of:
   A762D, A762P, A762V or A762T; and/or
   P826E, P826Q, P826Y, P826T, P826D or P826I;
   and the pyruvate carboxylase mutant protein has an activity of carboxylation of pyruvate into oxaloacetate as a malate precursor.

In another preferred embodiment, the pyruvate carboxylase mutant protein further has one or more core amino acid mutations selected from the group consisting of:
   P824V, P824A, P824I, P824Y, P824L, P824M, P824N, P824R, or P824T; and/or
   P1031E, 1031S, P1031N or P1031G.

In another preferred embodiment, the pyruvate carboxylase mutant protein further has one or more core amino acid mutations selected from the group consisting of:
   G837D, or G837H;
   A254K, A254E, A254R, or A254F;
   H51N, or H51G; and
   F453E, or F453P.

In another preferred embodiment, the pyruvate carboxylase mutant protein is derived from wild-type pyruvate carboxylase.

In another preferred embodiment, the wild-type pyruvate carboxylase is derived from *Corynebacterium glutamicum*.

In another preferred embodiment, the pyruvate carboxylase mutant protein further comprises an active fragment, an variant or derivative protein thereof, wherein the active fragment, variant or derivative protein of the pyruvate carboxylase mutant protein have at least 85%, 90%, 91%, 92%, 93%, 94%, 95%, 96%, 97%, 98%, 99% sequence identity to that of the pyruvate carboxylase mutant protein and has an activity of carboxylation of pyruvate to synthesize malate precursor oxaloacetate.

In another preferred embodiment, the derivative protein of the pyruvate carboxylase mutant protein has a sequence in which, except for one or more of the core amino acid mutations, the remaining sequence is the same as or substantially the same as the sequence of SEQ ID NO: 1.

In another preferred embodiment, as compared with SEQ ID NO: 1 (wild-type), the sequence of the pyruvate carboxylase mutant protein has core amino acid mutations at the following position:

A762D and P826E;
A762D and P824V;
P824V and P826E
P824V and P1031E; or
A762D, P826E and P1031E.

In another preferred embodiment, the pyruvate carboxylase mutant protein is shown in any of SEQ ID NOs: 2-20, and 175.

In the second aspect of the present invention, it provides a mutant malate transporter which, based on a sequence as shown in SEQ ID NO: 22, has one or more core amino acid mutations selected from the group consisting of:
I80K, I80W, or I80C; and
R272A, or R272F;
and the mutant malate transporter has an activity of transporting malate from inside to outside of a cell.

In another preferred embodiment, the mutant protein further has one or more core amino acid mutations selected from the group consisting of:
E8Q, E8Y, E8R, or E8P; and/or
V142I, V142S or V142C.

In another preferred embodiment, the mutant protein further has one or more core amino acid mutations selected from the group consisting of:
F97V, or F97R;
F101Y, or F101W;
Y115E;
S123K, S123H, S123R, or S123D;
I301W, I301F, I301H, I301K, or I301Y;
L140N, L140H, or L140K;
P163I, P163V, P163F, P163L, P163Q, or P163Y;
A191R, or A191K;
F201Q, F201G, F201N or F201K;
A214V, A214G or A214D;
E222S, or E222H;
H227F, or H227W; and/or
M251E, or M251G.

In another preferred embodiment, as compared with SEQ ID NO: 22 (wild-type), the sequence of the mutant malate transporter has core amino acid mutations at the following positions:
I80K and R272A; or
I80K, E8Q and R272A.

In another preferred embodiment, the sequence of the mutant malate transporter is shown in SEQ ID NOs: 23-42, 176.

In another preferred embodiment, the mutant malate transporter also includes an active fragment, an variant or derivative protein thereof, wherein the active fragment, variant or derivative protein of the mutant malate transporter have at least 85%, 90%, 91%, 92%, 93%, 94%, 95%, 96%, 97%, 98%, 99% sequence identity to that of mutant malate transporter and has an activity of transporting malate from inside of cells to outside of cells.

In the third aspect of the present invention, it provides an isolated polynucleotide or a combination thereof which encodes the pyruvate carboxylase mutant protein in the first aspect of the present invention and/or the mutant malate transporter in the second aspect of the present invention.

In another preferred embodiment, the isolated polynucleotide respectively encodes the pyruvate carboxylase mutant protein in the first aspect of the present invention or the mutant malate transporter in the second aspect of the present invention.

In another preferred embodiment, the isolated polynucleotide combination contains polynucleotides encoding both the pyruvate carboxylase mutant protein in the first aspect of the present invention and the mutant malate transporter in the second aspect of the present invention.

In the fourth aspect of the present invention, it provides a vector containing the isolated polynucleotide according to the third aspect of the present invention.

In another preferred embodiment, the expression vector contains the polynucleotide encoding the mutant protein of pyruvate carboxylase according to the first aspect of the invention and the mutant malate transporter according to the second aspect of the invention.

In the fifth aspect of the present invention, it provides a host cell which contains the vector of the fourth aspect of the present invention, or in which the isolated polynucleotide of the third aspect of the present invention is integrated into nucleic acid of the host cell.

In another preferred embodiment, the host cell comprises a cell derived from the following microorganisms: *Saccharomyces cerevisiae, Pichia pastoris, Saccharomyces monacensis, Saccharomyces bayanus, Saccharomyces pastorianus, Saccharomyces carlsbergensis, Saccharomyces pombe, Kluyveromyces marxiamus, Kluyveromyces lactis, Kluyveromyces fragilis, Pichia stipites, Candida shehatae, Candida tropicalis, Escherichia coli, Bacillus subtilis, Torulopsis glabrata, Aspergillus oryzae, Rhizopus oryzae, Ustilago trichophora, Thermobifida fusca, Myceliophthora thermophila, Myceliophthora heterothallica.*

In another preferred embodiment, the host cell includes *Saccharomyces cerevisiae, Pichia pastoris*, or *Myceliophthora thermophila.*

In another preferred embodiment, the host cell expresses pyruvate carboxylase mutant protein only.

In another preferred embodiment, the host cell expresses the mutant malate transporter only.

In another preferred embodiment, the host cell simultaneously expresses pyruvate carboxylase mutant protein and mutant malate transporter.

In the sixth aspect of the present invention, it provides a method for preparing the pyruvate carboxylase mutant protein of the first aspect of the invention and/or the mutant malate transporter of the second aspect of the invention, which comprises the following steps:
under conditions suitable for expression, culturing the host cell of the fifth aspect of the present invention, thereby expressing the pyruvate carboxylase mutant protein of the first aspect of the present invention and/or the mutant malate transporter of the second aspect of the present invention; and
isolating the expression product, thereby obtaining the pyruvate carboxylase mutant protein according to the first aspect of the invention and/or the mutant malate transporter according to the second aspect of the invention.

In the seventh aspect of the present invention, it provides a method for increasing the yield of malic acid, which comprising the following steps:
i) introducing the polynucleotide according to the third aspect of the present invention or a combination thereof into a suitable host cell;
ii) in the presence of a carbon source, culturing the host cell, thereby increasing malate production.

In another preferred embodiment, the carbon source comprises glucose, sucrose, galactose, xylose, glycerin, or methanol.

In another preferred embodiment, the suitable host cell comprises a cell derived from the following microorganisms: *Pichia pastoris, Saccharomyces cerevisiae, Myceliophthora thermophila,* and/or *Myceliophthora heterophila.*

In the eighth aspect of the present invention, it provides a mutant protein combination comprising the pyruvate carboxylase mutant protein according to the first aspect of the invention and the mutant malate transporter according to the second aspect of the invention.

In the ninth aspect of the present invention, it provides a use of the pyruvate carboxylase mutant protein according to the first aspect of the invention and/or the mutant malate transporter according to the second aspect of the invention, and the isolated polynucleotide or a combination thereof according to the third aspect of the invention, the vector according to the fourth aspect of the present invention, the host cell according to the fifth aspect of the present invention, or the mutant protein combination according to the eighth aspect of the present invention, for increasing malate production and/or for preparing of malic acid.

In another preferred embodiment, the "increasing malate production" comprises an increase in malate production by at least 10%, preferably by at least 20%, 30%, 40%, or 50%, as compared to a wild-type strain producing malate, It should be understood that, within the scope of the present invention, the technical features specifically described above and below (such as in the Examples) can be combined with each other, thereby constituting a new or preferred technical solution which needs not be redundantly described one by one.

DETAILED DESCRIPTION OF THE INVENTION

Figure 1:
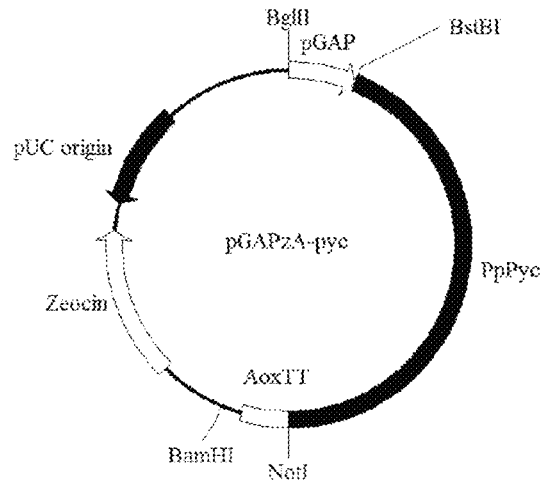
FIG. 1 shows a map of the pyc expression plasmid.

After extensive and extensive research, the inventors have unexpectedly discovered for the first time that, after the catalytic machinery and transporter for malate synthesis were modified, that is, after the core the amino acid of specific sites of pyruvate carboxylase and malate transporter is mutated, the ability of the microbial strain to produce malic acid has been significantly improved, so that more pyruvate precursor can flow to the target product malic acid, thereby effectively increasing malic acid production. Specifically, the inventors first constructed a high-throughput screening scheme for malate synthesis coupling in *Pichia pastoris*, compared pyruvate carboxylase and malate transporters from different sources, and found the target protein to be modified. The inventors constructed random mutation libraries for the two target proteins separately, and obtained multiple pyruvate carboxylase and malate transporter mutants with increased malate production after multiple screenings, and then performed single amino acid saturation mutation and combination mutation to obtain pyruvate carboxylase mutants with improved catalytic activity and malate transporter mutants with improved malate transport capacity, and constructed a series of engineering strains for the efficient synthesis of malate. On this basis, the invention is completed.

Malic Acid and its Synthesis

Malic acid (2-hydroxy-1,4-succinic acid) is an important platform compound and is widely used in the pharmaceutical, cosmetic, food and beverage industries.

There are currently five main routes reported for malate synthesis, namely TCA cycle, reduced TCA (or reverse TCA) or rTCA, cyclic glyoxylic acid cycle and non-cyclic glyoxylic acid cycle, and reverse catalyzation of pyruvate into malic acid via malic enzyme. Among them, the rTCA cycle and the malic enzyme pathway are the most effective. The theoretical conversion rate of glucose to malic acid is 2. However, malic enzyme mainly catalyzes the decomposition of malic acid into pyruvate. Therefore, the most common method is the rTCA pathway for synthesizing malic acid.

Starting from glucose, it is converted into pyruvate by glycolysis, and pyruvate is converted into oxaloacetate by pyruvate carboxylase, and oxaloacetate is converted into malate by malate dehydrogenase. Malate is transported out of cell by a transporter. The conversion efficiency of each step in the process, the side reaction diversion, the coenzyme that catalyzes each step of the reaction, and reducibility and the energy state of cells will all affect the synthesis of malic acid.

In the past, the synthesis was mainly based on chemical methods. However, these processes mainly produced a mixture of D- and L-malic acid, which was difficult to separate. However, the microbiology method of the present invention can synthesize high-purity L-malic acid.

Pyruvate Carboxylase

Pyruvate carboxylase (PYC) is one of the key enzymes involved in the central metabolic pathway in the organism. It forms oxaloacetate through the carboxylation of pyruvate and participates in the TCA cycle. This reaction is also the first step of the gluconeogenesis pathway. Most pyruvate carboxylase is composed of four identical subunits, the molecular weight of a single subunit is 120-130 kDa, and the molecular weight of the functional tetramer is about 520 kDa. Pyruvate carboxylase requires tetramerization to function. The protein after tetramerization is as much as 520 kDa, which is difficult to secrete out of the cell. Although pyruvate carboxylase can be screened by measuring enzyme activity, since it only resides in the cell, it is necessary to break the cell to perform enzyme activity measurement. If it is difficult to carry out the cell-breaking treatment for all mutants in a mutation library, it is very difficult to improve the protein. At present, there are only a few site-directed mutations that target complex formation based on the crystal structure of such complex-forming proteins and very few mutants are involved. No protein engineering modification has been done for CgPYC without crystal structure.

The pyruvate carboxylase of the present invention is derived from *Corynebacterium glutamicum* and its wild-type (named CgPYC) has a sequence number of WP_011013816.1, as shown in SEQ ID NO: 1, and its encoding nucleic acid is shown in SEQ ID NO: 21, which is for the first time used in malate synthesis strains. By constructing random mutations, site-directed mutations and combined mutations, multiple single point mutations that can significantly increase malate synthesis *Pichia pastoris* by more than 30%, and two double and triple mutations that increase malate by more than 40% are obtained. Meanwhile, the mutant protein can increase malic acid by 16% in *Myceliophthora thermophila*.

Malate Transporter

Malate transporter plays an important role in the synthesis of malate. The transporters used in the present invention for malate production are mainly from *Aspergillus oryzae* (A0090023000318 (C4T318)), wherein the wild-type protein sequence (named AoMae) is shown in SEQ ID NO: 22, and its encoding nucleic acid is shown in SEQ ID NO: 43; or from *Schizosaccharomyces pombe* (NM 001020205.2) and DCT from *Aspergillus carbonarius* (AQW79505.1), wherein the theoretical molecular weight of the key AoMae protein is 42.2 kDa.

The malate transporter Aomae is a membrane protein. The usual evaluation standard for membrane proteins is to measure the substrate transport ability. The protein needs to be purified, constructed in liposomes, or constructed in a strain without similar function and having multiple gene knockout, and then measured by isotope-labeled substrates. In addition, the transport is divided into efflux type and internal transport type, and the protein consistency of the membrane protein is generally low. All these factors make it very difficult to modify membrane protein.

In the present invention, through random mutation, site-directed mutation and combined mutation, a series of mutation sites were obtained to significantly improve the level of malic acid synthesis. Among them, I80K/E8Q/R272A and I80K/R272A can improve malate synthesis in *Pichia pastoris* by more than 10%. Malic acid can also be increased by 10.5% in *Myceliophthora thermophila*.

Mutant Protein and its Derivatives

It is known to the skilled in the art that if a certain enzyme is to be mutated in order to obtain a mutant with improved activity, the key point is to find a site where the activity can be improved after the mutation. In the present invention, enzymes whose amino acid sequences are shown in SEQ ID NO: 1 and 22 are mutated at specific sites to obtain corresponding mutants with significantly improved activity. As used herein, the terms "mutant protein" and "mutant" are used interchangeably and refer to the mutant protein of pyruvate carboxylase and/or malate transporter, and the correspondence of the mutant protein of pyruvate carboxylase or mutant protein of malate transporter can be obtained accordingly in the context of context. Specifically, the pyruvate carboxylase mutant protein of the present invention generally refers to the sequence shown in SEQ ID NO: 1 and/or 22 (wild-type), and after modification, it has one or more core amino acid mutations selected at the following sites.

(1) When the mutation is performed based on the sequence of SEQ ID NO: 1, it may have one or more core amino acid mutations as follows:

A762D, A762P, A762V or A762T;
P826E, P826Q, P826Y, P826T, P826D or P826I;
P824V, P824A, P824I, P824Y, P824L, P824M, P824N, P824R, or P824T;
P1031E, 1031S, P1031N or P1031G;
P824V, P824A, P824I, P824Y, P824L, P824M, P824N, P824R, or P824T;
P1031E, 1031S, P1031N or P1031G;
G837D, or G837H;
A254K, A254E, A254R, or A254F;
H51N, or H51G; and/or
F453E, or F453P;
and the pyruvate carboxylase mutant protein has the activity of carboxylation of pyruvate into oxaloacetate, a precursor for synthesizing malate.

A preferred pyruvate carboxylase mutant protein, based on a sequence as shown in SEQ ID NO: 1, has one or more core amino acid mutations selected from the group consisting of:

A762D and P826E;
A762D and P824V;
P824V and P826E
P824V and P1031E; or
A762D, P826E and P1031E.

The sequence of a preferred pyruvate carboxylase mutant protein is shown in any of SEQ ID NOs: 2-20, and 175.

(2) When the mutation is performed based on the sequence of SEQ ID NO: 22, it may have one or more core amino acid mutations as follows:

I80K, I80W, or I80C;
R272A, or R272F;
E8Q, E8Y, E8R, or E8P;
V142I, V142S or V142C;
F97V, or F97R;
F101Y, or F101W;
Y115E;
S123K, S123H, S123R, or S123D;
I301W, I301F, I301H, I301K, or I301Y;
L140N, L140H, or L140K;
P163I, P163V, P163F, P163L, P163Q, or P163Y;
A191R, or A191K;
F201Q, F201G, F201N or F201K;
E222S, or E222G;
H227F, or H227W; and/or
M251E, or M251G;
and the mutant malate transporter has the activity of transporting malate from inside to outside of a cell.

A preferred mutant malate transporter, based on a sequence as shown in SEQ ID NO: 22, has one or more core amino acid mutations selected from the group consisting of:

I80K and R272A; or
I80K, E8Q and R272A.

The sequence of a preferred mutant malate transporter is shown in any of SEQ ID NOs: 23-42, and 176.

```
                                                                    SEQ ID No.: 1
MSTHTSSTLP  AFKKILVANR  GEIAVRAFRA  ALETGAATVA  IYPREDRGSF  HRSFASEAVR   60

IGTEGSPVKA  YLDIDEIIGA  AKKVKADAIY  PGYGFLSENA  QLARECAENG  ITFIGPTPEV  120

LDLTGDKSRA  VTAAKKAGLP  VLAESTPSKN  IDEIVKSAEG  QTYPIFVKAV  AGGGGRGMRF  180

VASPDELRKL  ATEASREAEA  AFGDGAVYVE  RAVINPQHIE  VQILGDHTGE  VVHLYERDCS  240

LQRRHQKVVE  IAPAQHLDPE  LRDRICADAV  KFCRSIGYQG  AGTVEFLVDE  KGNHVFIEMN  300

PRIQVEHTVT  EEVTEVDLVK  AQMRLAAGAT  LKELGLTQDK  IKTHGAALQC  RITTEDPNNG  360
```

-continued
```
FRPDTGTITA YRSPGGAGVR LDGAAQLGGE ITAHFDSMLV KMTCRGSDFE TAVARAQRAL  420

AEFTVSGVAT NIGFLRALLR EEDFTSKRIA TGFIADHPHL LQAPPADDEQ GRILDYLADV  480

TVNKPHGVRP KDVAAPIDKL PNIKDLPLPR GSRDRLKQLG PAAFARDLRE QDALAVTDTT  540

FRDAHQSLLA TRVRSFALKP AAEAVAKLTP ELLSVEAWGG ATYDVAMRFL FEDPWDRLDE  600

LREAMPNVNI QMLLRGRNTV GYTPYPDSVC RAFVKEAASS GVDIFRIFDA LNDVSQMRPA  660

IDAVLETNTA VAEVAMAYSG DLSDPNEKLY TLDYYLKMAE EIVKSGAHIL AIKDMAGLLR  720

PAAVTKLVTA LRREFDLPVH VHTHDTAGGQ LATYFAAAQA GADAVDGASA PLSGTTSQPS  780

LSAIVAAFAH TRRDTGLSLE AVSDLEPYWE AVRGLYLPFE SGTPGPTGRV YRHEIPGGQL  840

SNLRAQATAL GLADRFELIE DNYAAVNEML GRPTKVTPSS KVVGDLALHL VGAGVDPADF  900

AADPQKYDIP DSVIAFLRGE LGNPPGGWPE PLRTRALEGR SEGKAPLTEV PEEEQAHLDA  960

DDSKERRNSL NRLLFPKPTE EFLEHRRRFG NTSALDDREF FYGLVEGRET LIRLPDVRTP 1020

LLVRLDAISE PDDKGMRNVV ANVNGQIRPM RVRDRSVESV TATAEKADSS NKGHVAAPFA 1080

GVVTVTVAEG DEVKAGDAVA IIEAMKMEAT ITASVDGKID RVVVPAATKV EGGDLIVVVS 1140

SEQ ID No.: 22
MLTPPKFEDE KQLGPVGIRE RLRHFTWAWY TLTMSGGGLA VLIISQPFGF RGLREIGIAV   60

YILNLILFAL VCSTMAIRFI LHGNLLESLR HDREGLFFPT FWLSVATIIC GLSRYFGEES  120

NESFQLALEA LFWIYCVCTL LVAIIQYSFV FSSHKYGLQT MMPSWILPAF PIMLSGTIAS  180

VIGEQQPARA ALPIIGAGVT FQGLGFSISF MMYAHYIGRL MESGLPHSDH RPGMFICVGP  240

PAFTALALVG MSKGLPEDFK LLHDAHALED GAIIELLAIS AGVFLWALSL WFFCIAIVAV  300

IRSPPEAFHL NWWAMVFPNT GFTLATITLG KALNSNGVKG VGSAMSICIV CMYIFVFVNN  360

VRAVIRKDIM YPGKDEDVSD                                              380
```

In view of the teaching of the present invention and the prior art, those skilled in the art should understand that the mutant protein of the present invention should also include the active fragment of the mutant protein, modified or unmodified variant or derivatives thereof.

Specifically, the active fragment, variant or derivative protein of the pyruvate carboxylase mutant protein includes a sequence which is based on SEQ ID NOs: 2-20, and may has one or several (for example, usually 1-30, preferably 1-10, more preferably 1-6, and further preferably 1-3, and most preferably 1) deletion, insertion and/or substitution of amino acid residues, and still has an activity (cA1) of convert pyruvic acid into malate precursor oxaloacetate via carboxylation, wherein the activity cA1 is significantly higher than the corresponding activity (cA0) of wild-type pyruvate carboxylase shown in SEQ ID NO: 1 and the term "significantly higher" mean any value in "(cA1-cA0)/cA0≥10%-500%", such as ≥15%, 20%, 25%, 30%, 40%, 50%, or 100%.

The active fragment, variant or its derivative of the mutant malate transporter includes a sequence which is based on a sequence as shown in SEQ ID NOs: 23-42, and may has one or several (for example, usually 1-30, preferably 1-10, more preferably 1-6, and further preferably 1-3, and most preferably 1) deletion, insertion and/or substitution of amino acid residues, and still has an activity (aA1) of transporting malic acid from inside to outside of cells wherein the activity aA1 is significantly higher than the corresponding activity (aA0) of the wild-type malate transporter shown in SEQ ID NO: 22, and the term "significantly higher" mean any value in "(cA1−cA0)/cA0≥10−500%", such as ≥15%, 20%, 25%, 30%, 40%, 50%, or 100%.

The skilled in the art can generate conservatively mutated mutants based on, for example, the conservative amino acid substitutions as shown in the following table.

| Primary residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

As used herein, modification (typically without changing the primary structure) forms of proteins include: chemically derived forms of proteins such as acetylation or carboxylation in vivo or in vitro. Modifications also include glycosylation. Modification forms also include sequences with phosphorylated amino acid residues (e.g. phosphotyrosine, phosphoserine, phosphothreonine). Also included are proteins that have been modified to improve their proteolytic resistance or optimize their solubility. These techniques are known to those skilled in the art.

In addition, the derivative protein of the mutant protein of the present invention also includes a fusion protein or conjugate formed by the mutant protein of the present invention or an active fragment thereof and other proteins or markers.

Preferably, the active fragment, variant or derivative protein of the mutant protein of the present invention has a sequence identity to SEQ ID NO: 1 or 22 of at least 85%, 90%, 91%, 92%, 93%, 94%, 95%, 96%, 97%, 98%, 99%, respectively.

The mutant protein of the present invention can be combined to further increase the production of malic acid.

Encoding Nucleic Acid and its Combination

Based on the pyruvate carboxylase mutant protein or mutant malate transporter of the present invention, the present invention also provides an isolated polynucleoside or its degenerate variants encoding pyruvate carboxylase mutant protein or mutant malate transporter. The polynucleotide of the present invention may be in the form of DNA or RNA. DNA forms include cDNA, genomic DNA, or synthetic DNA. DNA can be single-stranded or double-stranded. DNA can be a coding strand or a non-coding strand. The coding region sequence encoding the mature polypeptide may be the same as the nucleotide sequence encoding the pyruvate carboxylase mutant protein and/or the mutant malate transporter in the embodiments of the present invention or is a degenerate variant. As used herein, "degenerate variant" in the present invention refers to a nucleotide sequence which encodes a pyruvate carboxylase mutant protein and/or the mutant malate transporter in the claims of the present invention, but is different from the nucleotide sequence for the acid carboxylase mutant protein or mutant malate transporter in the examples of the present invention.

Vectors, Host Cells

The coding polynucleotide sequence can be inserted into a recombinant expression vector or genome. The term "recombinant expression vector" refers to a bacterial plasmid, bacteriophage, yeast plasmid, plant cell virus, mammalian cell virus or other vectors well known in the art. In short, as long as it can replicate and stabilize in the host, any plasmid and vector can be used. An important feature of expression vectors is that they usually contain an origin of replication, a promoter, a marker gene and translation control elements.

Those skilled in the art can use well-known methods to construct vectors for expression of DNA sequences containing coding sequences for "pyruvate carboxylase mutant protein and/or mutant malate transporter" and appropriate transcription/translation control signals, including in vitro recombinant DNA technology, DNA synthesis technology, in vivo recombinant technology, etc. The DNA sequence can be effectively linked to an appropriate promoter in an expression vector to guide mRNA synthesis. The expression vector also includes a ribosome binding site for translation initiation and a transcription terminator.

The host cells described herein include host cells containing the above-mentioned expression vector, or in which the coding sequence of the mutant protein of the present invention is integrated into its genome. The host cells may include those derived from Sac fungi, have a very high evolutionary relationship, and have high similarity in the sequence and functionality of pyruvate carboxylase and malate transporter. The preferred microorganism cells are as follows:

*Saccharomyces cerevisiae*, *Pichia pastoris*, *Saccharomyces monacensis*, *Saccharomyces bayanus*, *Saccharomyces pastorianus*, *Saccharomyces carlsbergensis*, *Saccharomyces pombe*, *Kluyveromyces marxiamus*, *Kluyveromyces lactis*, *Kluyveromyces fragilis*, *Pichia* stipites, *Candida shehatae*, *Candida tropicalis*, *Escherichia coli*, *Bacillus subtilis*, *Torulopsis glabrata*, *Aspergillus oryzae*, *Rhizopus oryzae*, *Ustilago trichophora*, *Thermobifida fusca*, *Myceliophthora thermophila*, *Myceliophthora heterothallica*.

The mutant protein of the present invention can be obtained by a conventional recombinant transformation method in the art, and the mutant protein can be expressed in a cell, on a cell membrane, or secreted out of the cell. If necessary, the recombinant protein can be isolated and purified by various separation methods using its physical, chemical and other characteristics. These methods are well known to those skilled in the art. Examples of these methods include but are not limited to: conventional renaturation treatment, treatment with protein precipitation agent (salting out method), centrifugation, osmotic disruption, ultrasonic treatment, high-pressure homogenization, ultracentrifugation, molecular sieve chromatography (gel filtration), adsorption chromatography, ion exchange chromatography, affinity chromatography, high performance liquid chromatography (HPLC) and various other liquid chromatography techniques and combinations of these methods. The host cell obtained in the present invention can express pyruvate carboxylase mutant protein and mutant malate transporter separately and/or simultaneously.

Preparation of Mutant Protein

The present invention also provides a method for preparing pyruvate carboxylase mutant protein mutant malate transporter, which includes culturing the host cell of the present invention under conditions suitable for expression, thereby expressing pyruvate carboxylase mutant protein and/or the mutant malate transporter; and isolating the pyruvate carboxylase mutant protein and/or the mutant malate transporter.

The obtained mutant protein may optionally be purified to obtain a more pure mutant protein product.

Preferably, the conditions suitable for expression include conventional techniques in the art, and purification techniques include nickel column purification, ion exchange chromatography and the like.

Carbon Source

There is no particular limitation on carbon sources useful in the present invention. Carbon source is a type of nutrient for the growth of microorganisms (such as the host cells of the present invention) and is a carbon-containing compound. Preferably, carbon sources that can be used in the present invention include glucose, sucrose, cellobiose, lactose, galactose, xylose, glycerin, or methanol.

Application

The mutant protein of the present invention can be used separately or simultaneously to increase the yield of malic acid. The pyruvate carboxylase mutant protein of the present invention improves malate synthesis by at least 10% with a single mutation at a specific site, and mutations in preferred strains can reach more than 30%, while double and triple mutations can increase malic acid yield by 40%. For mutant malate transporters, malate production is increased by at least 10% after mutation at specific sites, and mutations in preferred strains can reach more than 30%. When the two proteins are modified and combined in the present invention, the production of malic acid is synergistically improved.

The Beneficial Effects of the Invention

In the present invention, by constructing a malate synthesis pathway in *Pichia pastoris*, the pyruvate carboxylase and malate transporter synthesizing ability in the malate synthesis pathway are coupled with malate production, and then to $CaCO_3$ hydrolysis circle so that the directed evolution of the two proteins is realized for the first time, and significantly improves the level of malic acid synthesis. The pyruvate carboxylase mutant protein of the present invention improves malate synthesis by at least 10% with a single mutation at a specific site, and mutations in preferred strains can reach more than 30%, while double and triple mutations increase malic acid yield by 40%. For mutant malate transporters, malate production is increased by at least 10% after mutations at specific sites, and mutations in preferred strains can reach more than 30%. When the two proteins are modified and combined in the present invention, the production of malic acid is synergistically improved.

The invention will now be further described with reference to specific embodiments. It should be understood that these examples are merely illustrative of the invention and are not intended to limit the scope of the invention. The experimental methods not specified for conditions in the following examples are generally carried out according to conventional conditions, such as those described in Sambrook et al., Molecular Cloning: Laboratory Manual (New York: Cold Spring Harbor Laboratory Press, 1989), or conditions suggested by the manufacturer.

All the primers used were synthesized by Jinweizhi Biotechnology Co., Ltd. The genes involved were also synthesized by Jinweizhi Biotechnology Co., Ltd. The sequence involved in the present invention is shown in the SEQUENCE LISTING.

The methods for obtaining various biological materials described in the examples are merely to provide an experimentally obtained method to achieve the purpose of specific disclosure, and should not be a limitation on the source of the biological materials of the present invention. In fact, the sources of biomaterials used are wide, and any biomaterials that can be obtained without violating laws and ethics can be replaced and used according to the prompts in the embodiments.

In the present invention, malic acid and succinic acid were purchased from Sigma reagent company.

Figure 2:
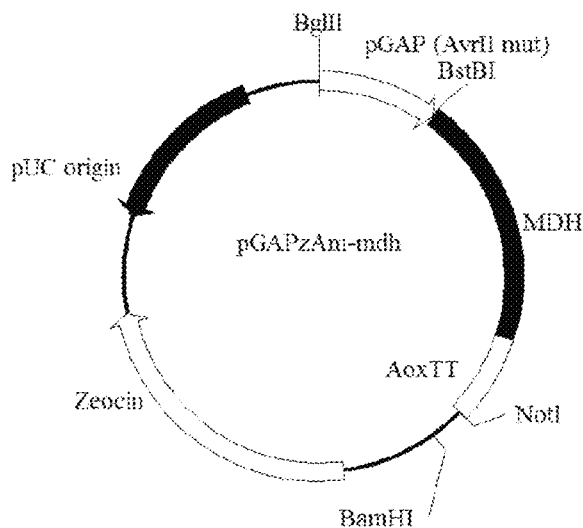
FIG. 2 shows a map of the mdh expression plasmid.
Figure 3:
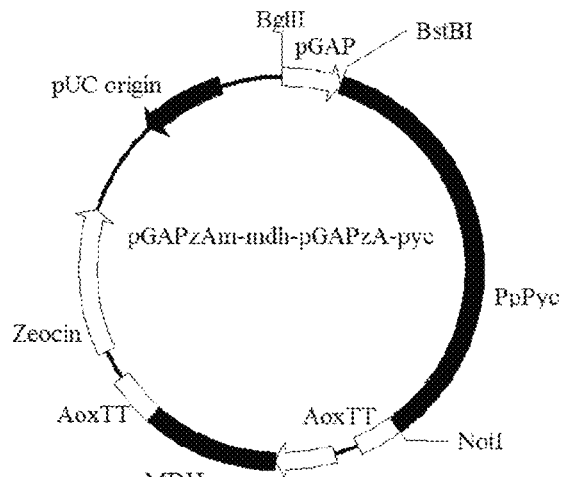
FIG. 3 shows a map of mdh and pyc tandem expression plasmid.

Example 1 Construction of *Pichia pastoris* Dicarboxylic Acid Transporter Screening Platform I. Construction of *Pichia pastoris* Overexpressing Pyruvate Carboxylase and Malate Dehydrogenase Vectors:

By using primers AvrII-F (SEQ ID NO: 44): (CCACCGCCCGTTACCGTCCGAAGGAAATTT-TACTCTGCTGGAG) and AvrII-R (SEQ ID NO: 45): (CTCCAGCAGAGTAAAAT-TTCCTTCGGACGGTAACGGGCGGTGG), and using pGAPzA as the template system, PCR was conducted. The PCR reaction system were as follows: 5× PHUSION™ HF buffer 10 µl, 10 mM dNTPs 1 µl, AvrII-F1 µl, AvrII-R 1 µl, pGAPzA 1 µl, PHUSION™ DNA polymerase 0.5 µl, water 35.5 µl. The PCR reaction conditions were: first 98° C. 30 s; then 98° C. 10 s, 60° C. 30 s, 72° C. 3 min, 30 cycles; finally 72° C. 10 min, 4° C. 10 min. After the PCR reaction was completed, the product was purified through a purification column. Into 1 µg of plasmid was added 1 µl of restriction enzyme DpnI to remove the template, and the mixture was then heat-inactivated at 85° C. for 5 min. 5 µl of the product was transformed into *E. coli* competent cell DH5 and spread on 25 µg/ml Zeocin's low-salt LB medium plate and was screened for positive clones and sequenced. The sequencing results showed that the AvrII cleavage site on pGAPzA had been successfully removed, and it was named pGAPzAm. Using primers PYC-F (SEQ ID NO: 46): (GGGTTCGAAACG ATGGCCGAAGAAGAC-TACTCCC)/PYC-R (SEQ ID NO: 47): (GGGGCGGCCGCTTACTCAGCCTTGACGAT-TTTGGCGATC), MDH-F (SEQ ID NO: 48): (GGGTTCGAAACGATGGTTAAAGTCACAGTTTGCG-GAG)/MDH-R (SEQ ID NO: 49): (GGGGCGGCCGCT-TAGTTGCCAGCAATGAAGGCAGTTCC), using *Pichia pastoris* GS115 genome as a template to amplify the pyruvate carboxylase PYC and malate dehydrogenase MDH genes by PCR. PCR reaction conditions were as follows: first 98° C. 30 s; Then 98° C. 10 s, 60° C. 30 s, 72° C. 3 min (PYC) or 1 min (MDH), 30 cycles; finally 72° C. 10 min, 4° C. 10 min. After PCR, product was purified by the purification column, double digestion was performed with BstBI and NotI. Plasmid pGAPzA and pGAPzAm were digested with the same enzymes, and then PYC and pGAPZA, MDH and pGAPzAm were connected by T4DNA ligase at 22° C. for 1 h, and 10 µl was taken. The ligation product was transformed into *E. coli* competent cell DH5a, plated on 25 µg/ml Zeocin low-salt LB medium plate and screened for positive clones, followed by sequencing. The sequencing results showed that plasmid pGAPzA-PYC (FIG. 1) and plasmid pGAPzAm-MDH (FIG. 2) were successfully constructed. Further, pGAPzAm-MDH was double-digested with BglII and BamHI to obtain the expression frame of MDH, which was connected into the plasmid pGAPzA-PYC digested with BamH1, and the ligation product was transformed into *E. coli* competent cell DH5a, which was inoculated on 25 µg/ml Zeocin and the positive clones were selected on the low-salt LB medium plate and sequenced, thereby constructing the expression plasmid pGAPZA-PYC-pGAPzAm-MDH, whose schematic diagram is shown in FIG. 3.

II. Construction of *Pichia pastoris* Strain Overexpressing Pyruvate Carboxylase and Malate Dehydrogenase:

1. *Pichia pastoris* GS115 strain stored at −80° C. was inoculated onto YPD (1% yeast extract, 2% peptone, 2% glucose, 2% agar) plate and incubated at 30° C. to grow single clones.
2. A single clone was taken in 250 ml of liquid YPD medium with a volume of 30 ml, cultured at 200 rpm, 30° C. and activated for 2 days.
3. The activated *Pichia pastoris* GS115 strain was transferred to the medium containing 30 ml of liquid YPD twice, wherein the inoculation amount was controlled at one-thousandth, and cultured at 200 rpm, 30° C. for about 16 h-20 h until OD600 reached 1.0.
4. After centrifugation at 3000 rpm, 4° C., the bacterial cells were collected, and washed twice with pre-cooled sterile water.
5. Then the bacterial cells were washed with pre-chilled 1M sorbitol once and the precipitate was collected after centrifugation.
6. About 400 µl of 1M sorbitol was added to resuspend the cells, then it was divided each 80 µl and added into a pre-chilled 1.5 ml centrifuge tube to make *Pichia pastoris* GS115 competent cells, and stored at −80° C. until use.
7. The pGAPzA-PYC-pGAPzAm-MDH plasmid was extracted, the plasmid was linearized with AvrII, and then transformed into *Pichia pastoris* GS115 competent cells by electroporation. Then 1 ml of pre-cooled 1M sorbitol was added and the mixture was left at 30° C. 2 h, and then was inoculated on the YPD plate containing 50 or 75 μg/ml. After the growth of bacteria to be used for malic acid production, the strain was named as P0.

III. Determination of Malic Acid Synthesis Capacity

Figure 7:
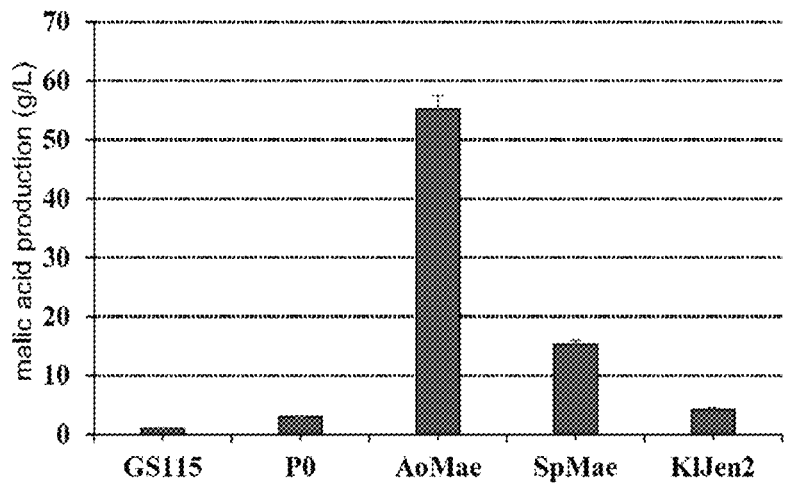
FIG. 7 shows the effect of malic acid production by overexpression of pyc and mdh and overexpression of different homotransporters on malate production.

Malate synthesis strain was first activated with YPD medium for 48 h, and then inoculated with initial OD 600=1.0 on malate-producing medium (100 g/L glucose, 1.24 g/L KNO$_3$, 0.64 g/L KH$_2$PO$_4$, 0.04 g/L ZnSO$_4$.7H$_2$O, 0.25 g/L MgSO$_4$.7H$_2$O, 0.0005 g/L FeSO$_4$.7H$_2$O 4 g/L peptone, 0.1 g/L CaCl$_2$), 75 g/L CaCO$_3$, 0.1 g/L histine), wherein 30 ml liquid medium was added into a 250 ml triangle bottle liquid, and cultured at 200 rpm, 30° C. incubation. Every 24 h, 1 ml was sampled, 1 ml 20% (V/V) H$_2$SO$_4$ was added, and acidification treatment was conducted at 80° C. for 30 min. A certain amount of water was added for dilution and after centrifugation, the supernatant was taken and HPLC AMINEX™ 87H chromatographic column was used to measure the content of malic acid. The HPLC parameter conditions were as follows: the column temperature was 35° C., the detector temperature was 40° C., the mobile phase was 5 mM H$_2$SO$_4$, the flow rate was 0.5 ml/min, and the malic acid standard was used for quantification. The results are shown in FIG. 7. Compared with the GS115 strain, the P0 strain produced 3.0 g/l malic acid and GS115 produced 1.0 g/L malic acid.

Example 2 Construction and Screening of a Dicarboxylic Acid Transporter Mutation Library I. Construction of Expression Vectors for Binary Carboxylic Acid Transporters:

The primers were as follows:

```
Hph-BamH1
                                       SEQ ID NO: 50
GGGGGATCCTGTACAGCTTGCCTCGTCCCC

Hph-R
                                       SEQ ID NO: 51
GTCGACACTGGATGGCGGCGTTAG
```

Using pAG34 plasmid as a template, PCR was conducted to amplify the hygromycin gene. The PCR reaction conditions were as follows: first 98° C. 30 s; then 98° C. 10 s, 60° C. 30 s, 72° C. 2 min, 30 cycles; last 72° C. 10 min, 4° C. for 10 min. After the PCR reaction was completed, the product was purified through a purification column, digested with BamH1, ligated into pGAPzA plasmid digested with BamH1 and EcoRV, and the ligated product was transformed into E. coli competent cell DH5a. The monoclonal sequence was confirmed by sequencing, and pGAP-hph was obtained.

The primers were as follows:

```
his-BglII
                                       SEQ ID NO: 52
GGGAGATCTGTTGTAACACTGGCAGAGCATTACG his-BamH1
                                       SEQ ID NO: 53
GGGGGATCCGTCCCAGTTTCTCCATACGAACC)
```

Using the pPIC9K plasmid as a template, PCR was conducted to amplify the his gene, and the PCR fragment was digested with BglII and BamH1 and ligated with pGAP-hph digested with BglII, thereby obtaining pGAP-hph-his.

The primers were as follows:

```
SpMae-ClaI
                                       SEQ ID NO: 54
GGGATCGATATGGGTGAACTCAAGGAAATCTTG

SpMae-NotI
                                       SEQ ID NO: 55
GGGGCGGCCGCTTAAACGCTTTCATGTTCACTACTAGG
```

Using *Schizosaccharomyces pombe* genomic DNA as a template, PCR was conducted to amplify SpMae gene.

The primers were as follows:

```
AoMae-BstBI
                                       SEQ ID NO: 56
GGGTTCGAAATGCTGACACCTCCCAAGTTTG

AoMae-NotI
                                       SEQ ID NO: 57
GGGCGGCCGCCTAATCAGATACATCCTCATCTTTAC
```

Using the cDNA of *Aspergillus Oryzae* DSM1863 (DSMZ, purchased from German Microbial and Cell Culture Co., Ltd.) as a template, PCR was conducted to amplify AoMae gene;

The primers were as follows:

```
Kljen2-EcoRI
                                       SEQ ID NO: 58
GGGGAATTCATGGCTGCAGAATCAATAGTGTCTC Kljen2-NotI
                                       SEQ ID NO: 59
GGGGCGGCCGCTTATGTTGAATTTCTTGCTTGAAATTTAGATC
```

Figure 4:
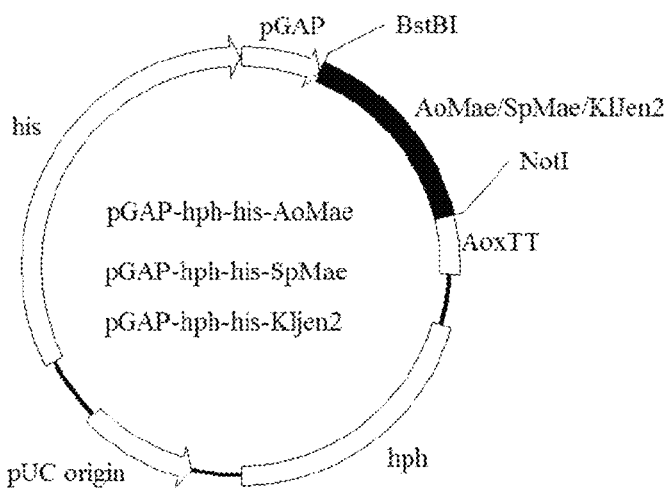
FIG. 4 shows a map of a plasmid for comparative expression and directed evolution of dicarboxylic acid transporter.

Kljen2 was obtained by PCR amplification by using *Kluyveromyces lactis* genomic DNA as a template. SpMae, AoMae and Kljen2 PCR products were digested and purified by ClaI/NotI, BstBI/NotI, and EcoRI/NotI, respectively, and connected into the vector pGAP-hph-his (digested with the corresponding enzymes (ClaI and BstBI were isocaudomer) The ligation product was transformed into E. coli competent cell DH5α, the monoclonal sequence was confirmed by sequencing, thereby obtaining pGAP-hph-his-SpMae, pGAP-hph-his-AoMae and pGAP-hph-his-Kljen2 (FIG. 4).

II. Comparison of Malic Acid Production Capacity of Candidate Protein of Dicarboxylic Acid Transporter:

Vectors pGAP-hph-his-SpMae, pGAP-hph-his-AoMae and pGAP-hph-his-Kljen2 were linearized by AvrII, transformed into P0 strain electroporation, and inoculated on MD (YNB 13.4 g/L, biotin 4×10−4 g/L, agar 2.0 g/L, glucose 2.0 g/L). The acid-producing medium was used for shake flask cultivation. The results are shown in FIG. 7. Among them, AoMae derived from *A. oryzae* was more favorable for the synthesis of organic acids such as malic acid. Using 100 g/L glucose as the substrate, 55 g/L malic acid could be synthesized. The strain was named P1 and used this strain as a starting protein for protein engineering.

III. Construction of High-Throughput Screening Method Based on Hydrolysis Circle:

Due to the soluble properties of 20-30 g/L calcium malate (found in the early stage of the present study), we established a high-throughput screening method based on hydrolysis circle. The specific method was as follows: when the transporter expression plasmid was transferred into P0 competent cells, after the growth of bacterial clone, the clone was pick with a sterile toothpick, and then punctured into the malic acid-producing solid medium (2.0 g/L agar was added to the liquid, and the concentration of $CaCO_3$ was 3 g/L). The size of the hydrolysis circle was checked every day, the ratio of the diameter of the hydrolysis circle to the diameter of the clone was used as the screening criterion: the larger the value, the higher the malic acid production.

Figure 8:
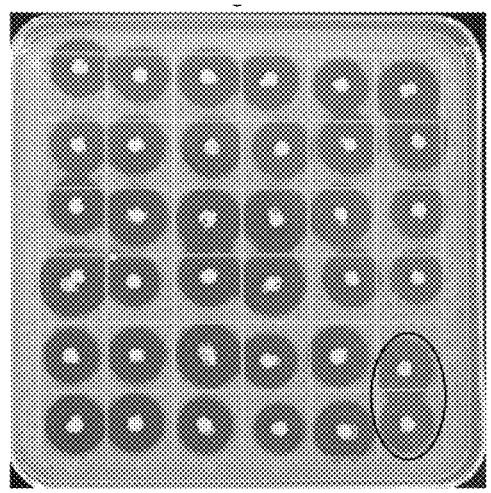
FIG. 8 shows the preliminary screening of the modified inoculating plate based on the hydrolyzed circle for transporter screening.
Figure 9:
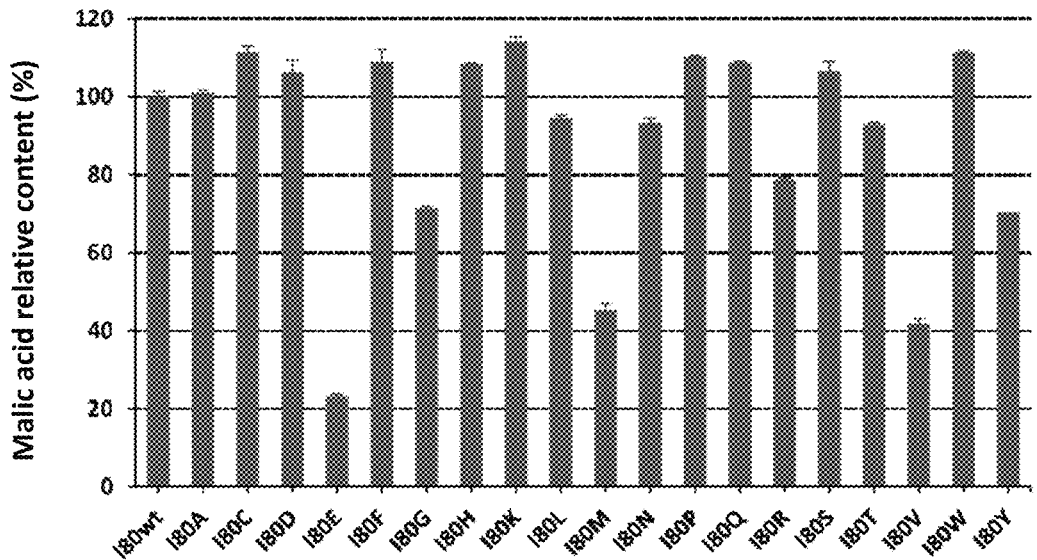
FIG. 9 shows the effect of Aomae I80 saturation mutation on malic acid production. Among them, I80K, I80W, and I80C increased malic acid production by 14.3%, 11.3%, and 11.5%, respectively.
Figure 10:
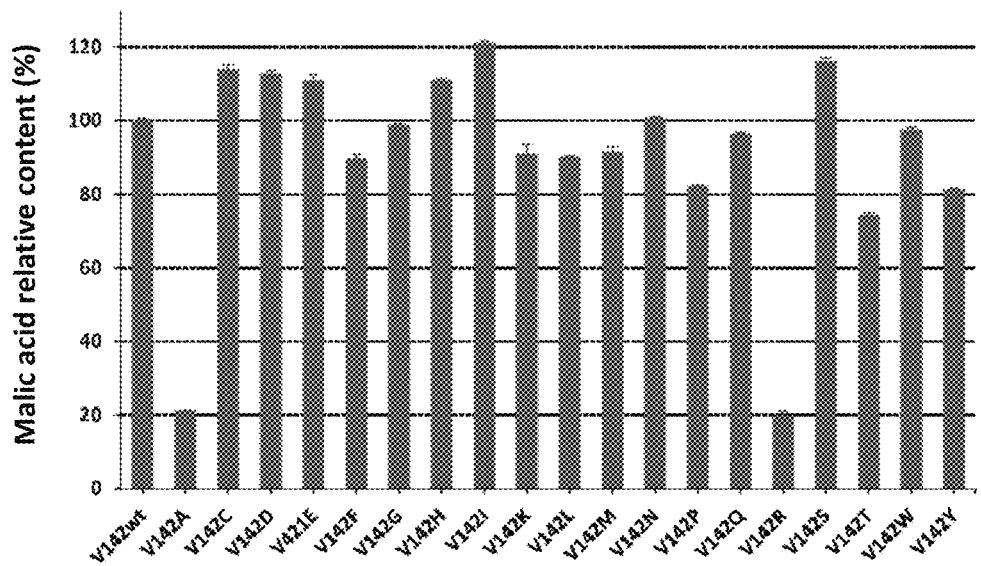
FIG. 10 shows the effect of Aomae V142 saturation mutation on malic acid production. Among them, V142I, V142S and V142C increased malic acid production by 21.1%, 16.2% and 14.1%, respectively.
Figure 11:
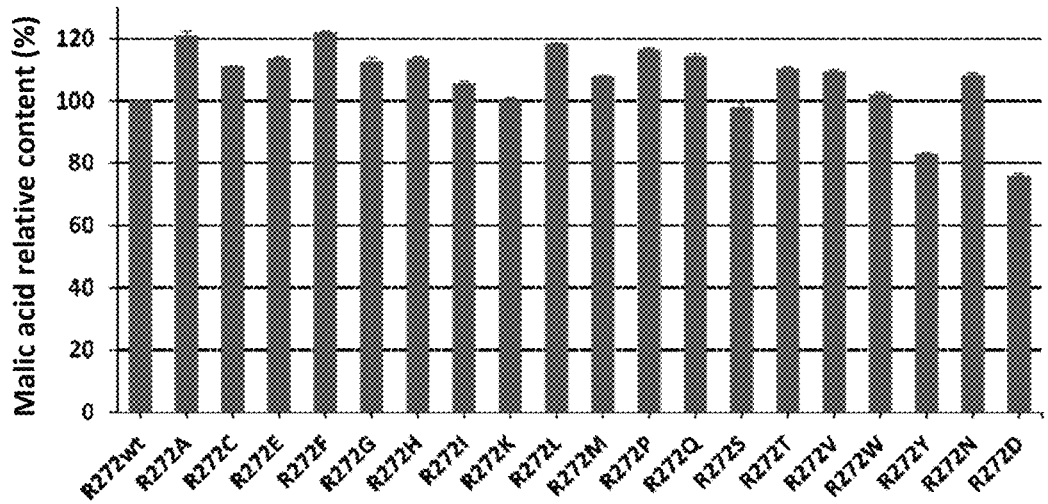
FIG. 11 shows the effect of Aomae R272 saturation mutation on malic acid production. Among them, R272A and R272F increased malic acid production by 21% and 22.1%, respectively.
Figure 12:
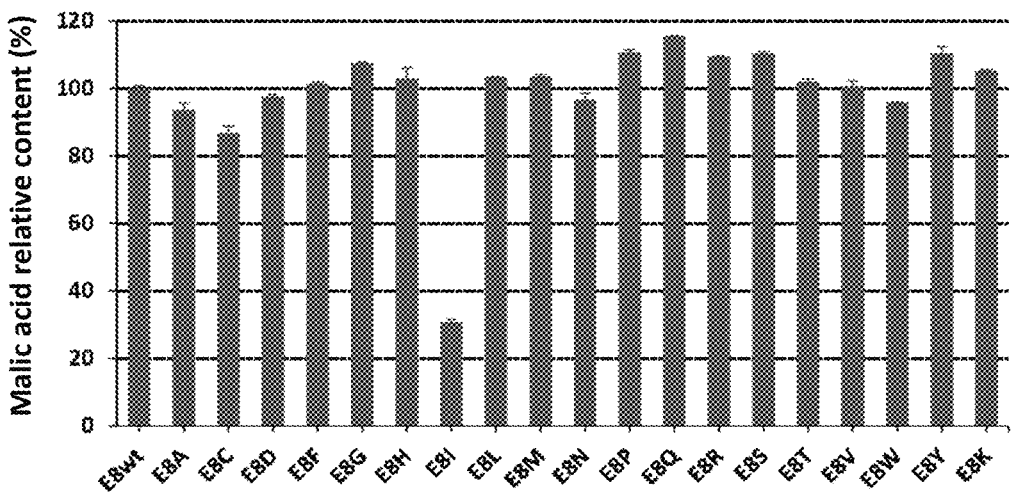
FIG. 12 shows the effect of Aomae E8 saturation mutation on malic acid production. Among them, E8Q, E8Y, E8R, and E8P increased malic acid production by 15.5%, 10.3%, 9.3%, and 10.7%, respectively.
Figure 13:
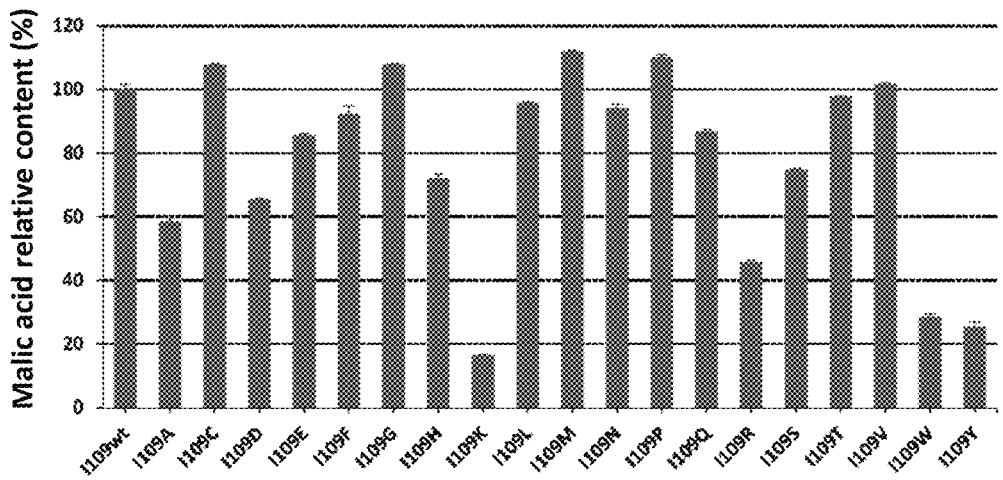
FIG. 13 shows the effect of Aomae I109 saturation mutation on malic acid production. Among them, I109M and I109P increased malic acid production by 12% and 10.2%, respectively.
Figure 14:
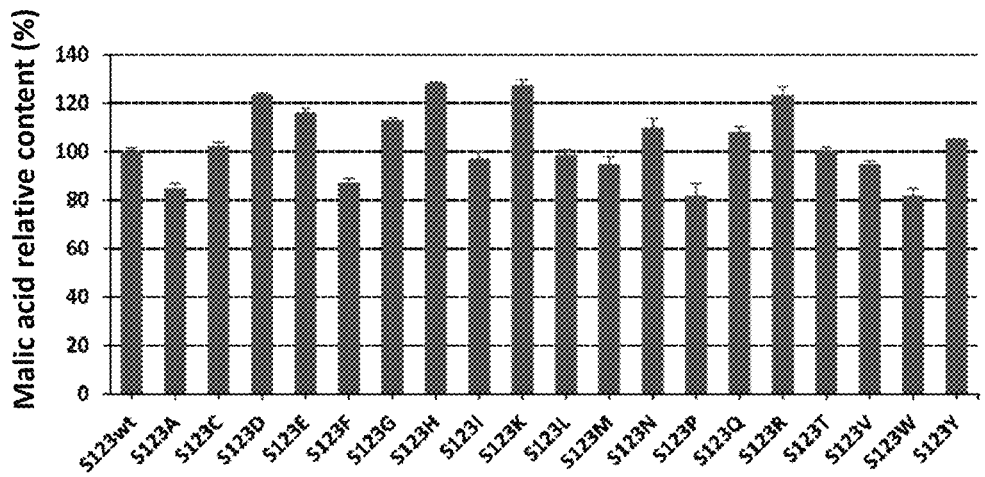
FIG. 14 shows the effect of Aomae S123 saturation mutation on malic acid production. S123, S123H, S123R, and S123D increased malic acid production by 27.4%, 28.2%, 23.4%, and 23.6%, respectively.
Figure 15:
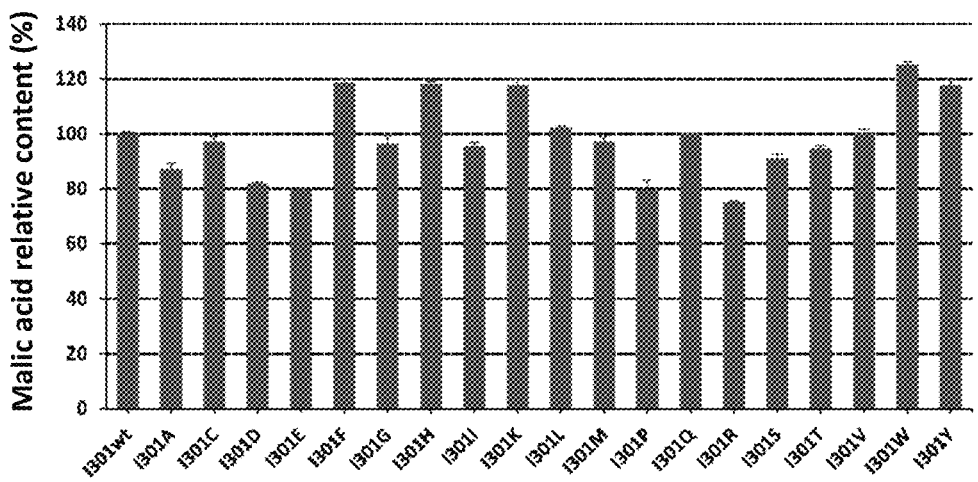
FIG. 15 shows the effect of Aomae I301 saturation mutation on malate production. I301W, I301F, I301H, I301K, and I301Y increased malate production by 25.2%, 18.6%, 18.3%, 17.6%, and 17.6%, respectively.
Figure 16:
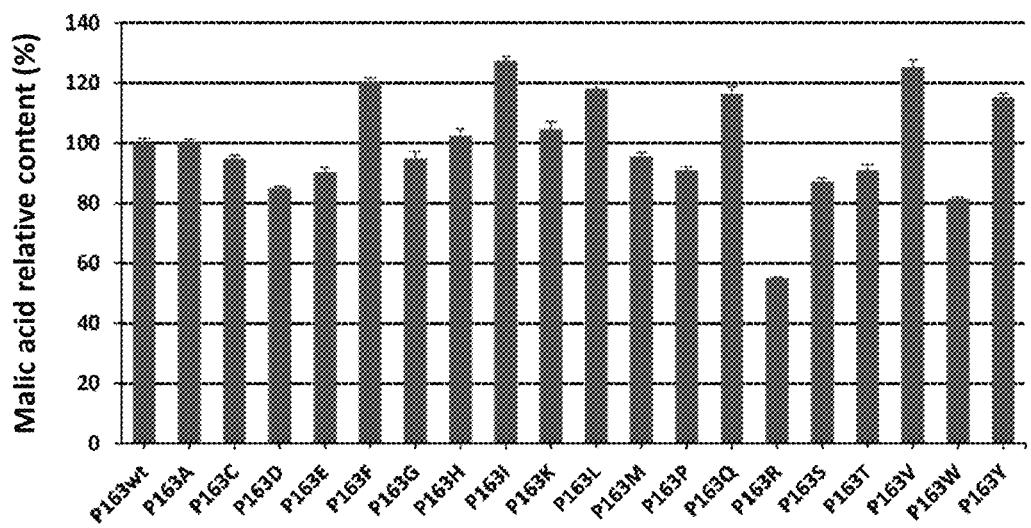
FIG. 16 shows the effect of Aomae P163 saturation mutation on malic acid production. Among them, P163I, P163V, P163F, P163L, P163Q, P163Y increased malic acid production by 27.4%, 25.2%, 20.6%, 18.1%, 16.5% and 15.3%, respectively.
Figure 17:
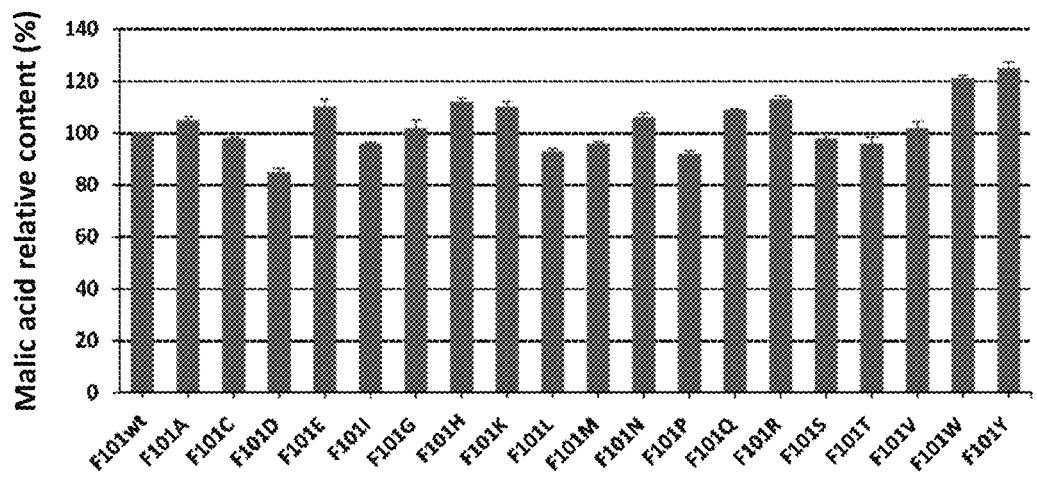
FIG. 17 shows the effect of Aomae F101 saturation mutation on malic acid production. Among them, F101Y and F101W increased malic acid production by 25% and 21%, respectively.
Figure 18:
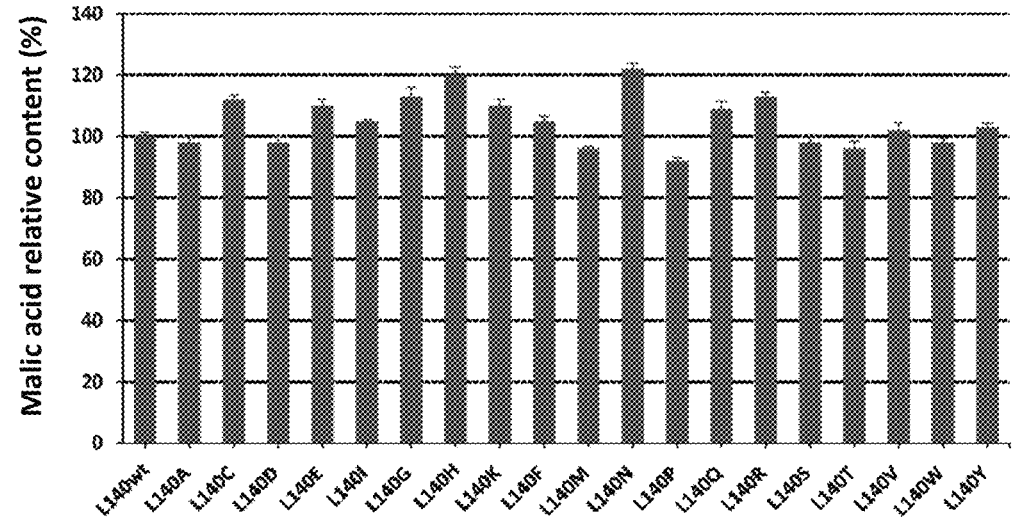
FIG. 18 shows the effect of Aomae L140 saturation mutation on malic acid production. Among them, L140N, L140K and L140H increased malic acid production by 22%, 10% and 20%, respectively.
Figure 19:
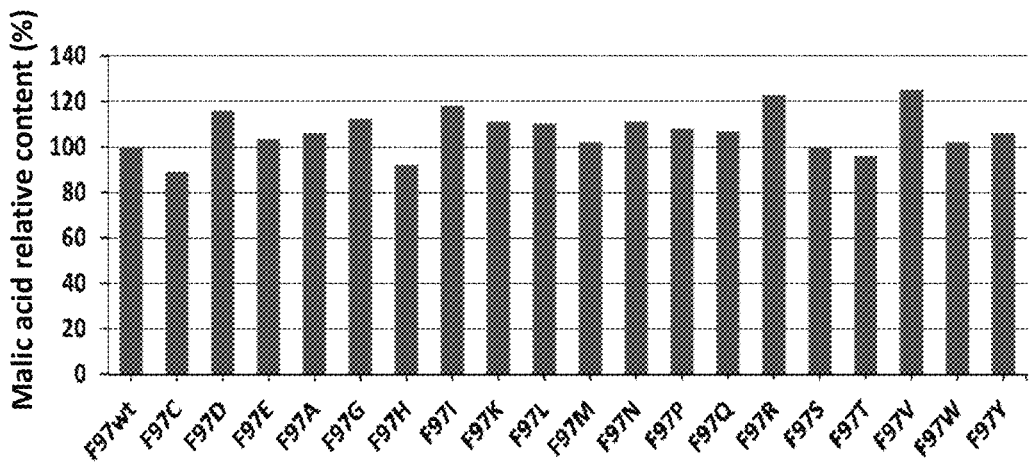
FIG. 19 shows the effect of Aomae F97 saturation mutation on malic acid production. Among them, F97V and F97R increased malic acid production by 25% and 22.7%, respectively.
Figure 20:
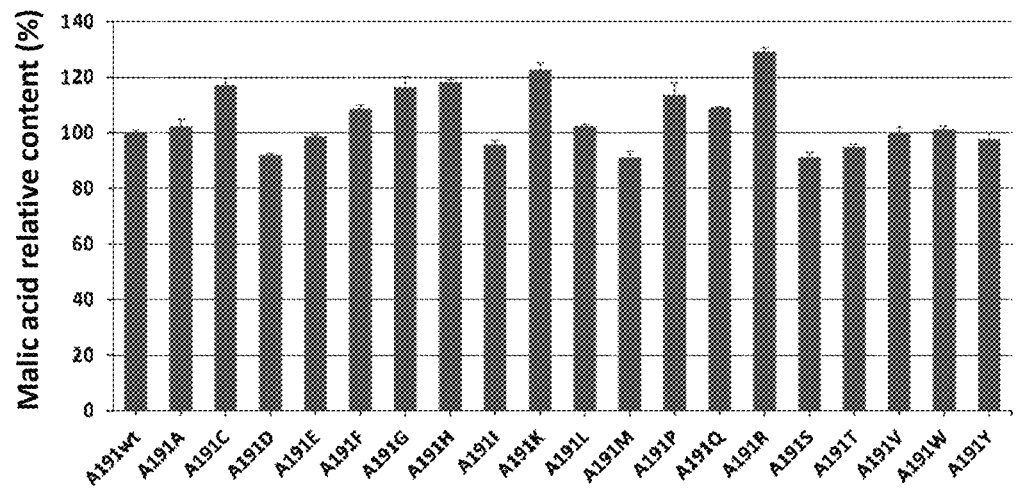
FIG. 20 shows the effect of Aomae A191 saturation mutation on malic acid production. Among them, A191R and A191K increased malic acid production by 29.2% and 22.6%, respectively.
Figure 21:
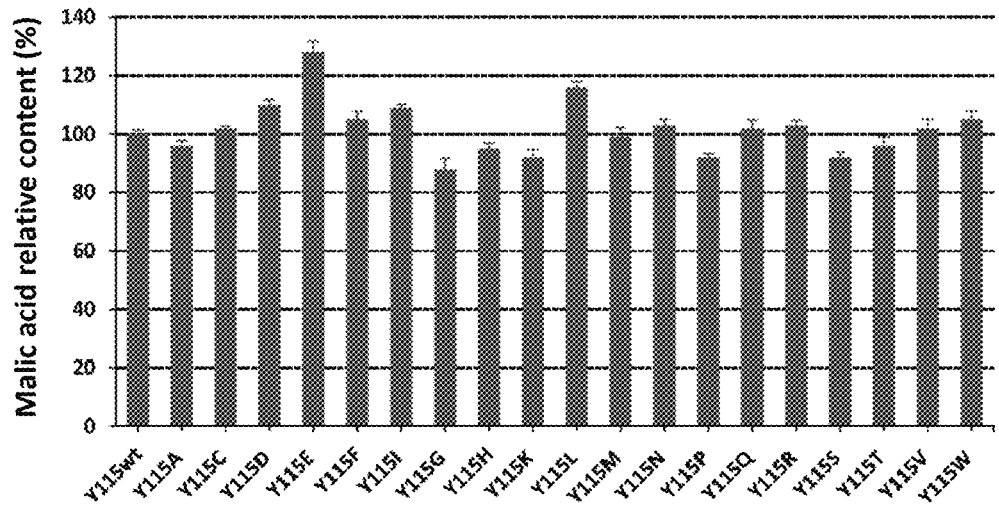
FIG. 21 shows the effect of Aomae Y115 saturation mutation on malic acid production. Among them, Y115E and Y115L increased malic acid production by 28% and 16%, respectively.
Figure 22:
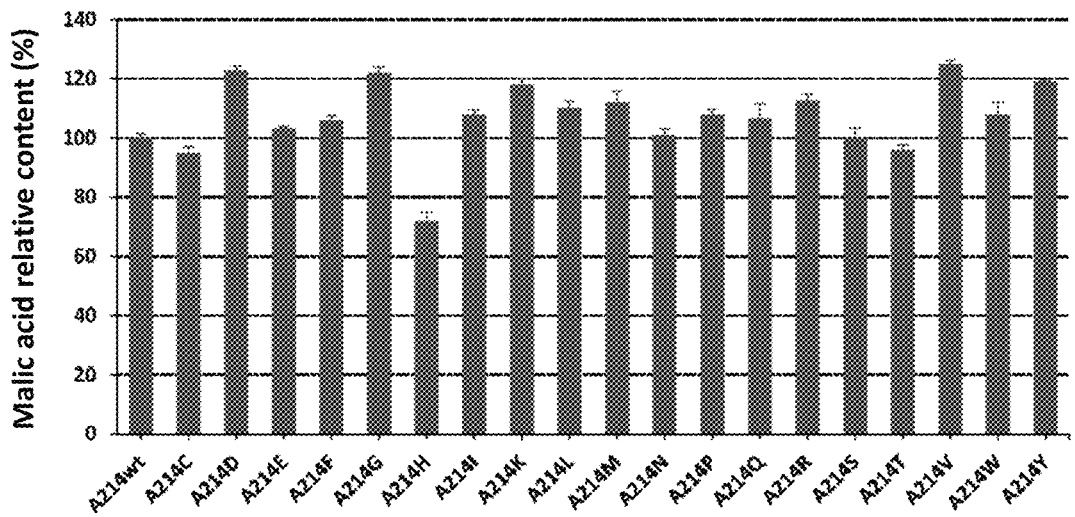
FIG. 22 shows the effect of Aomae A214 saturation mutation on malic acid production. Among them, A214V, A214G and A214D increased malic acid production by 25%, 22.1% and 21.3%, respectively.
Figure 23:
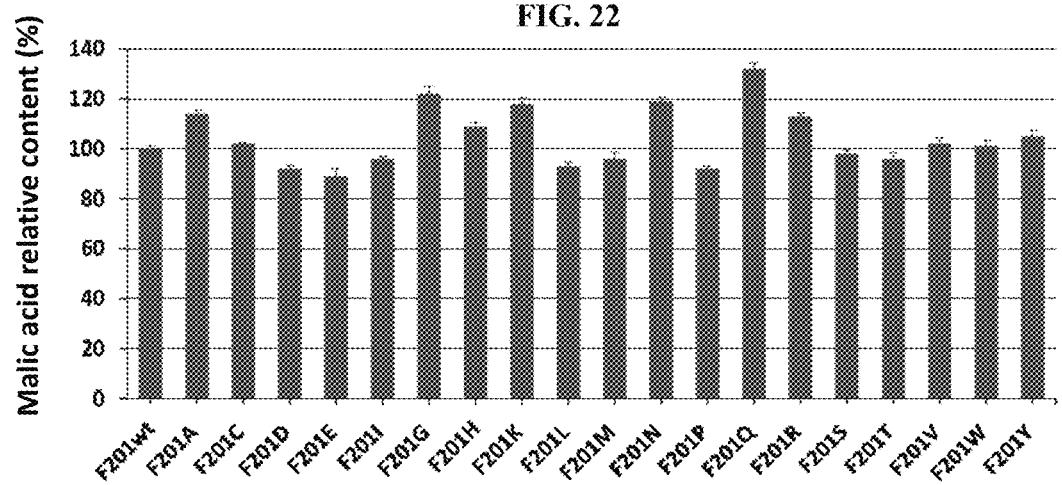
FIG. 23 shows the effect of Aomae F201 saturation mutation on malic acid production. Among them, F201Q, F201G, F201K, and F201N increased malic acid production by 32%, 22%, 18%, and 19%, respectively.
Figure 24:
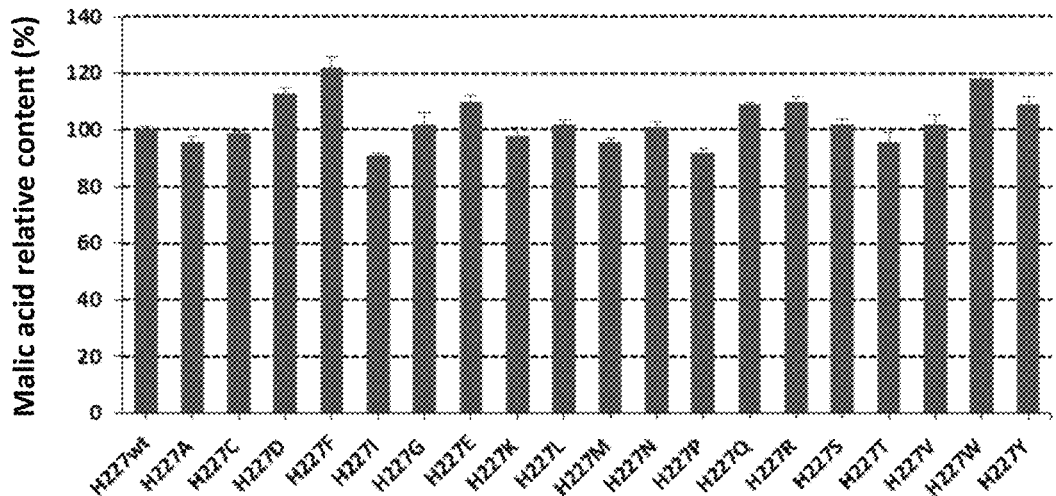
FIG. 24 shows the effect of Aomae H227 saturation mutation on malic acid production. Among them, H227F and H227W increased malic acid production by 22% and 18%, respectively.
Figure 25:
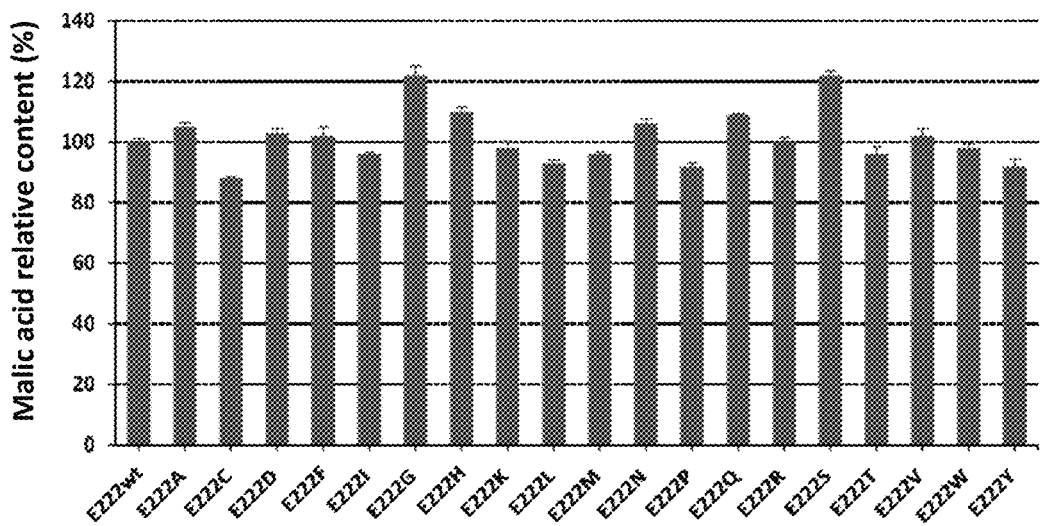
FIG. 25 shows the effect of Aomae E222 saturation mutation on malic acid production. Among them, E222S and E222G increased malic acid production by 22% and 22%, respectively.
Figure 26:
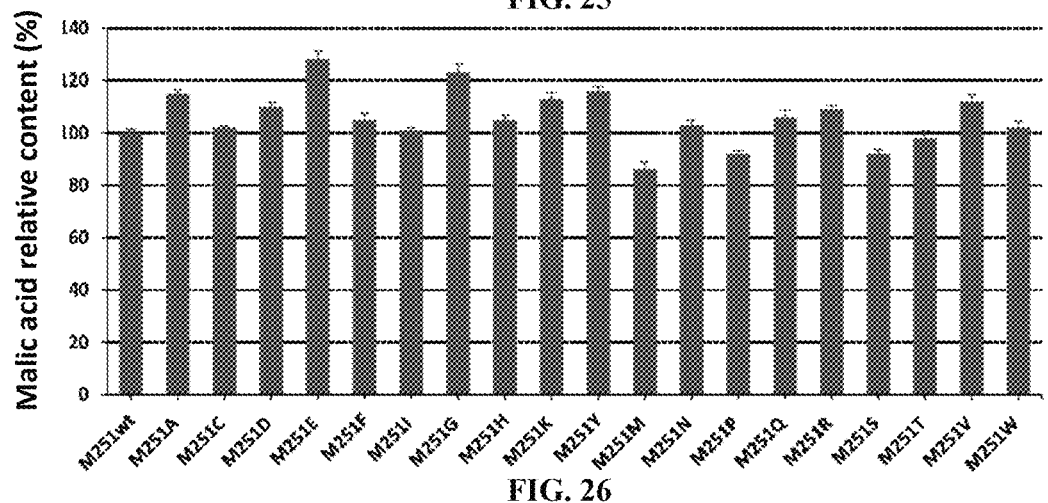
FIG. 26 shows the effect of Aomae M251 saturation mutation on malic acid production. Among them, M251E and M251G increased malic acid production by 28% and 23%.

IV. Construction of Aomae Mutation Library and Screening of Malate-Producing Mutants:

AoMae derived from *A. oryzae* was subjected to protein engineering. Using AoMae-BstBI and AoMae-NotI as primers, random mutation kit of GeneMorph II Random Mutagenesis (Agilent) was used to perform random mutation amplification of AoMae. The PCR product was digested with BstBI and NotI and then ligated with pGAP-hph-his. The ligated product was transformed into *E. coli* competent cell DH5α, which was inoculated on LB solid plate medium containing 125 µg/ml hygromycin, and incubated overnight at 37° C. Twenty single clones were randomly selected for sequencing, and the mutation rate was analyzed. The results showed that the mutation rate was about 1%. The mutant library was eluted with LB liquid medium containing 125 µg/ml hygromycin, and then recovered at 37° C. for 2 h, after which the mixed plasmid was extracted, transformed into P0 competent cells after linearization with AvrII, and spread on MD plates. After the single clones grew, single clone was punctured and inoculated in malate-producing solid medium. Using AoMae wild-type strain P1 as a control, strains with a larger hydrolysis circle in the mutation library than P1 (FIG. 8), was rescreened in shaking flask and malate content was determined by HPLC.

V. Determination of Copy Number of AoMae Gene in Malate-Producing Mutants

Genomic DNA of malate-producing mutants was extracted.

The primers were as follows:

```
Actin-RT1-F
                                    SEQ ID NO: 60
CTGCGATTCTTATTCTTCCGATTG Actin-RT1-R
                                    SEQ ID NO: 61
CAACCGAGGACAACCAACAG
```

Actin gene was amplified as an internal reference. The primers were as follows:

```
Aomae-RT1-F
                                    SEQ ID NO: 62
CATCATCTGCGGCTTGTC Aomae-RT1-R
                                    SEQ ID NO: 63
TGAGAAGACGAACGAGTATTG
```

The AoMae gene was amplified, and the results showed that the obtained AoMae transformants all had a single copy.

VI. Identification of Mutation Sites:

For mutant strains with increased malate production, their genomic DNA was extracted, and then AoMae-BstB1 and AoMae-NotI were used as primers for PCR amplification. After the amplification product was recovered by purification columns, it was ligated with pJET1.2 blunt vector, transformed into *E. coli* competent cell DH5α, inoculated on LB medium containing 100 µg/ml ampicillin, and the monoclones were sequenced to obtain the mutation sites: I80F, V142D, R272P, EBG, I109V, S123R, I301K, P163Q, F101H, L140N, F97G, A191C, Y115I, A214G, F201K, $H_{227}F$, M251Y and E222H.

VII. Site Saturation Mutations and Combination Mutations of AoMae Improved Malic Acid Synthesis:

Saturated mutations were conducted at key amino acid positions obtained from random mutation sites and based on structural comparison. The method was as follows: the mutation sites was introduced in the middle of primers; then PCR was performed to amplify pGAP-hph-his-AoMae by PCR; the PCR product was digested with DpnI; the template plasmid was removed, and then 5 µl of transformed *E. coli* competent cell DH5a was taken and inoculated on LB medium containing 125 µg/ml of hygromycin. The mutant sites were obtained by sequencing the single clones. The obtained AoMae mutant expression plasmid was linearized with AvrII, transformed into the P0 strain, and then cultured in liquid malic acid production medium via shake flask cultivation and HPLC analysis was conducted.

I80F mutation was obtained by using primers I80F (SEQ ID NO: 64): CCATGGC-TATAAGGTTCTTCCTGCACGGCAACCTTCTG and 180-rev (SEQ ID NO: 65): GAACCTTATAGC-CATGGTAGAG. For other 180X mutation (X represents 18 other amino acids except F), Primer 180X (SEQ ID NO: 66): CCATGGC-TATAAGGTTCXXXCTGCACGGCAACCTTCTG (XXX was a codon corresponding to different amino acids) and 180-rev (SEQ ID NO: 65) were used to introduce mutation.

V142D mutation was obtained by using primers V142D (SEQ ID NO: 67): GCGTCTGCACCT-TACTCGACGCAATCATCCAATACTCG and V142-rev (SEQ ID NO: 68): GAGTAAGGTGCAGACGCAGTAG. For other V142X mutation (X represents 18 other amino acids except F), Primer V142X (SEQ ID NO: 69): GCGTCTGCACCTTACTCXXXGCAATCATC-CAATACTCG (XXX was a codon corresponding to different amino acids) and V142-rev (SEQ ID NO: 68) were used to introduce mutation.

R272P mutation was obtained by using primers R272P (SEQ ID NO: 69): CACGCCCTGGAAGATGGCCCAAT-CATCGAGCTGCTGGC and R272-rev (SEQ ID NO: 70): GCCATCTTCCAGGGCGTG. For other R272X mutation (X represents 18 other amino acids except F), Primer R272X (SEQ ID NO: 71): CACGCCCTGGAAGATGGCXXXAT-CATCGAGCTGCTGGC(XXX was a codon corresponding to different amino acids) and R272-rev (SEQ ID NO: 70) were used to introduce mutation.

E8G mutation was obtained by using primers E8G (SEQ ID NO: 72): CTGACACCTCCCAAGTTTGGTGAT-GAGAAGCAGCTGGG and E8-rev (SEQ ID NO: 73): AAACTTGGGAGGTGTCAGC. For other E8X mutation (X represents 18 other amino acids except F), Primer E8X (SEQ ID NO: 74): CTGACACCTCCCAAGTTTXXXGAT-GAGAAGCAGCTGGG (XXX was a codon corresponding to different amino acids) and E8-rev (SEQ ID NO: 73) were used to introduce mutation.

I109V mutation was obtained by using primers I109V (SEQ ID NO: 75): TCTCCGTCGCAAC-CATCGTCTGCGGCTTGTCTCGCTAC and I109-rev (SEQ ID NO: 76): GATGGTTGCGACGGAGAG. For other I109X mutation (X represents 18 other amino acids except F), Primer I109X (SEQ ID NO: 77): TCTCCGTCGCAAC-CATCXXXTGCGGCTTGTCTCGCTAC(XXX was a codon corresponding to different amino acids) and I109-rev (SEQ ID NO: 76) were used to introduce mutation.

S123R mutation was obtained by using primers S123R (SEQ ID NO: 78): GTGAAGAATCGAATGAGAGATTC-CAACTAGCCCTCGAAG and S123-rev (SEQ ID NO: 79): CTCATTCGATTCTTCACCG. For other S123X mutation (X represents 18 other amino acids except F), Primer S123X (SEQ ID NO: 80): GTGAAGAATCGAATGAGXXXTTC-CAACTAGCCCTCGAAG (XXX was a codon corresponding to different amino acids) and S123-rev (SEQ ID NO: 79) were used to introduce mutation.

I301K mutation was obtained by using primers I301K (SEQ ID NO: 81): CGCCATTGTCGCCGT-CAAGCGCTCGCCCCCGAGGCC and I301-rev (SEQ ID NO: 82): GACGGCGACAATGGCGATG. For other S123X mutation (X represents 18 other amino acids except F), Primers S123X (SEQ ID NO: 83): CGCCAT-TGTCGCCGTCXXXCGCTCGCCCCCGAGGCC (XXX was a codon corresponding to different amino acids) and I301-rev (SEQ ID NO: 82) were used to introduce mutation.

P163Q mutation was obtained by using primers P163Q (SEQ ID NO: 84): GCCTTCAAACCATGATGCAAT-CATGGATCCTTCCAGCC AND P163Q-rev (SEQ ID NO: 85): CATCATGGTTTGAAGGCC. For other P163X mutation (X represents 18 other amino acids except F), Primers P163X (SEQ ID NO: 86): GCCTTCAAACCAT-GATGXXXTCATGGATCCTTCCAGCC (XXX was a codon corresponding to different amino acids) and P163-rev (SEQ ID NO: 85) were used to introduce mutation.

F101H mutation was obtained by using primers F101H (SEQ ID NO: 87): GGTCTCTTCTTCCCGACC-CACTGGCTCTCCGTCGCAACC and F101-rev (SEQ ID NO: 88): GGTCGGGAAGAAGAGACCC. For other F101X mutation (X represents 18 other amino acids except F), Primers F101X (SEQ ID NO: 89): GGTCTCTTCTTCCCGACCXXXTGGCTC TCCGTCGCAACC (XXX was a codon corresponding to different amino acids) and F101-rev (SEQ ID NO: 88) were used to introduce mutation.

L140N mutation was obtained by using primers L140N (SEQ ID NO: 90): TCTACTGCGTCTGCAC-CAACCTCGTCGCAATCATCC and L140-rev (SEQ ID NO: 91): GGTGCAGACGCAGTAGATC. For other L140X mutation (X represents 18 other amino acids except F), Primers L140X (SEQ ID NO: 92): TCTACTGCGTCTGCACCXXXCTCGTCGCAATCATCC (XXX was a codon corresponding to different amino acids) and L140-rev (SEQ ID NO: 91) were used to introduce mutation.

F97G mutation was obtained by using primers F97G (SEQ ID NO: 93): CATGACCGCGAG GGTCTCGGGTTCCCGACCTTCTGGCTC and F97-rev (SEQ ID NO: 94): GAGACCCTCGCGGTCATG. For other F97X mutation (X represents 18 other amino acids except F), Primers F97X (SEQ ID NO: 95): CATGACCGCGAGGGTCTCXXXTTCCCGACCTTC TGGCTC(XXX was a codon corresponding to different amino acids) and F97-rev (SEQ ID NO: 94) were used to introduce mutation.

A191C mutation was obtained by using primers A191C (SEQ ID NO: 96): CAACAACCCGCTCGCG-CATGTCTCCCCATCATCGGCGC and A191-rev (SEQ ID NO: 97): TGCGCGAGCGGGTTGTTG. For other A191X mutation (X represents 18 other amino acids except F), Primers F97X (SEQ ID NO: 98): CAACAACCCGCTCGCGCATGTCTCCCCAT-CATCGGCGC (XXX was a codon corresponding to different amino acids) and A191-rev (SEQ ID NO: 97) were used to introduce mutation.

Y115I mutation was obtained by using primers Y115I (SEQ ID NO: 99): TCTGCGGCTTGTCTCG-CATCTTCGGTGAAGAATCGAATG and Y115-rev (SEQ ID NO: 100): GCGAGACAAGCCGCAGATG. For other Y115X mutation (X represents 18 other amino acids except F), Primers F97X (SEQ ID NO: 101): TCTGCGGCTTGTCTCGCXXXTTCGGT-GAAGAATCGAATG (XXX was a codon corresponding to different amino acids) and Y115-rev (SEQ ID NO: 100 were used to introduce mutation.

A214G mutation was obtained by using primers A214G (SEQ ID NO: 102): TCAGCTTCATGATGTACGGGCAC-TACATCGGCCGACTG and A214-rev (SEQ ID NO: 103): GTACATCATGAAGCTGATG. For other A214X mutation (X represents 18 other amino acids except F), Primers A214X (SEQ ID NO: 104): TCAGCTTCAT-GATGTACXXXCACTACATCGGCCGACTG (XXX was a codon corresponding to different amino acids) and A214X-rev (SEQ ID NO: 103) were used to introduce mutation.

F201K mutation was obtained by using primers F201K (SEQ ID NO: 105): CGGCGCCGGCGTCAC-CAAGCAGGGCCTCGGCTTCTCC and F201-rev (SEQ ID NO: 106): GGTGACGCCGGCGCCGATG. For other F201X mutation (X represents 18 other amino acids except F), Primers A214X (SEQ ID NO: 107): CGGCGCCGGCGTCACCXXX-CAGGGCCTCGGCTTCTCC (XXX was a codon corresponding to different amino acids) and F201-rev (SEQ ID NO: 106) were used to introduce mutation.

H227F mutation was obtained by using primers $H_{227}F$ (SEQ ID NO: 108): ATG-GAGTCCGGCCTCCCCTTCAGCGACCACA-GACCAGGC and $H_{227}$-rev (SEQ ID NO: 109): GGG-GAGGCCGGACTCCATC. For other $H_{227}X$ mutation (X represents 18 other amino acids except F), Primers A214X (SEQ ID NO: 110): ATGGAGTCCGGCCTCCCCXXX-AGCGACCACAGACCAGGC (XXX was a codon corresponding to different amino acids) and $H_{227}$-rev (SEQ ID NO: 109) were used to introduce mutation.

M251Y mutation was obtained by using primers M251Y (SEQ ID NO: 111): CCCTCGCCCTCGTCGGCTA-CAGCAAAGGCCTCCCCGAAG and M251-rev (SEQ ID NO: 112): GCCGACGAGGGCGAGGGC. For other M251X mutation (X represents 18 other amino acids except F), Primers M251X (SEQ ID NO: 113): CCCTCGCCCTCGTCGGCXXX-AGCAAAGGCCTCCCCGAAG (XXX was a codon corresponding to different amino acids) and M251-rev (SEQ ID NO: 112) were used to introduce mutation.

E222H mutation was obtained by using primers E222Y (SEQ ID NO: 114): TACATCGGCCGACT-GATGCACTCCGGCCTCCCCCAC and E222-rev (SEQ ID NO: 115): CATCAGTCGGCCGATGTAG. For other E222X mutation (X represents 18 other amino acids except F), Primers M251X (SEQ ID NO: 116): TACATCGGCCGACTGATGXXXTCCGGCCTCCCC-CAC (XXX was a codon corresponding to different amino acids) and E222-rev (SEQ ID NO: 115) were used to introduce mutation.

Figure 27:
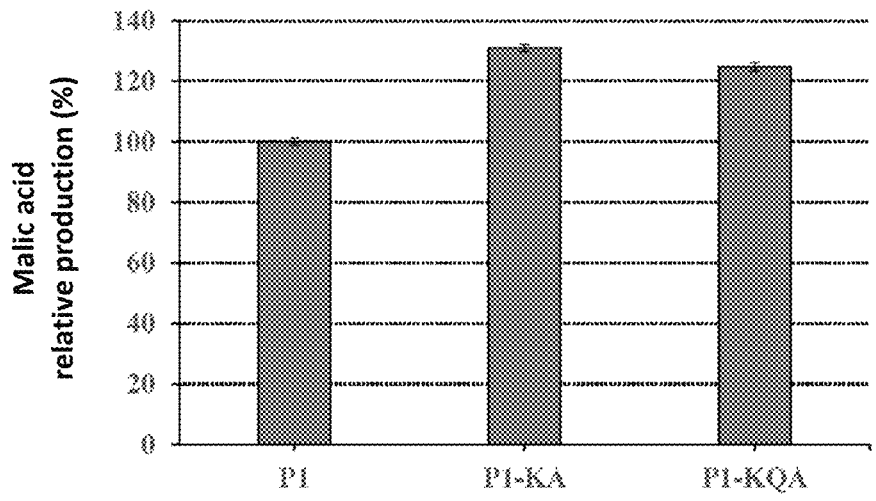
FIG. 27 shows the effect of Aomae combination mutation on malic acid production. Among them, I80K/R272A can increase malic acid production by more than 30%.

After each mutant was transformed into P0 strain, the results of screening malic acid were shown in FIGS. 9-26:

4 optimal points E8Q, I80K, V142I and R272A, which could improve malate synthesis capacity by 15%, 14%, 21% and 21% respectively, were selected for combined mutation by using the same method as saturation mutation. Further, for the combination mutation transformation of the P0 strain, the malate production results were shown in FIG. 27, of which the I80K/R272A (corresponding plasmid pGAP-hph-his-AoMaeKA) mutation had the best ability to synthesize malate, which was 30% higher than the starting strain and reached 71.5 g/L.

Example 3 Pyruvate Carboxylase Screening Platform Strain Construction

I. Dicarboxylic Acid Transporter Expression Vector Construction.
The primers were as follows:

```
Hph-BamH1
                                    SEQ ID NO: 117
GGGGGATCCTGTACAGCTTGCCTCGTCCCC

Hph-R
                                    SEQ ID NO: 118
GTCGACACTGGATGGCGGCGTTAG
```

Figure 5:
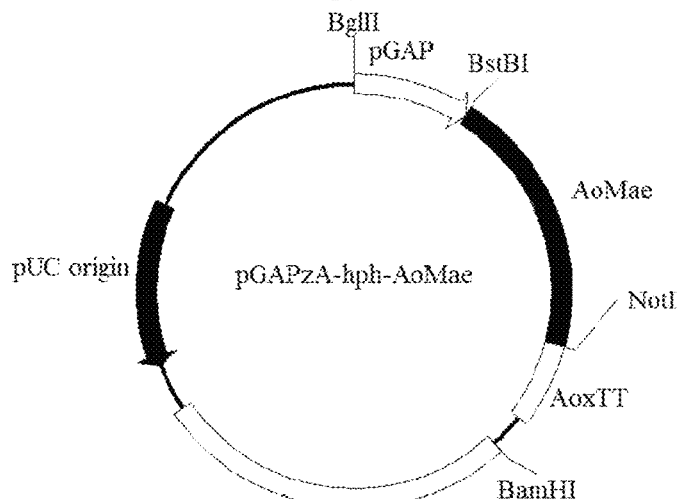
FIG. 5 shows a map of the Aomae expression plasmid.

Using the pAG34 plasmid as a template, PCR was conducted to amplify the hygromycin gene. The PCR reaction conditions were as follows: first 98° C. 30 s; then 98° C. 10 s, 60° C. 30 s, 72° C. 2 min, 30 cycles; last 72° C. 10 min, 4° C. for 10 min. After the PCR reaction was completed, the product was purified through a purification column, digested with BamH1, ligated into pGAPzA plasmid digested with BamH1 and EcoRV. The ligated product was transformed into *E. coli* competent cell DH5α, the sequence of single clone was confirmed correct by sequencing, thereby obtaining pGAP-hph. AoMae from *Aspergillus oryzae* was directly amplified via PCR from genomic DNA. AoMae was digested with BstBI and NotI and ligated with the vector pGAP-hph. The ligation product was transformed into *E. coli* competent cell DH5α. The sequence of single clone was confirmed correct by sequencing and pGAP-hph-AoMae was obtained (FIG. 5).

II. Construction of *Pichia pastoris* Strain Over-Expressing Dicarboxylic Acid Transporter
1. *Pichia pastoris* GS115 strain stored at −80° C. was inoculated onto YPD (1% yeast extract, 2% peptone, 2% glucose, 2% agar) plate and incubated at 30° C. to grow single clones.
2. A single clone was taken in 250 ml of liquid YPD medium with a volume of 30 ml, cultured at 200 rpm, 30° C. and activated for 2 days.
3. The activated *Pichia pastoris* GS115 strain was transferred to the medium containing 30 ml of liquid YPD twice, wherein the inoculation amount was controlled at one-thousandth, and cultured at 200 rpm, 30° C. for about 16 h-20 h until OD600 reached 1.0.
4. After centrifugation at 3000 rpm, 4° C., the bacterial cells were collected, and washed twice with pre-cooled sterile water.
5. Then the bacterial cells were washed with pre-chilled 1M sorbitol once and the precipitate was collected after centrifugation.
6. About 400 μl of 1M sorbitol was added to resuspend the cells, then it was divided each 80 μl and added into a pre-chilled 1.5 ml centrifuge tube to make *Pichia pastoris* GS115 competent cells, and stored at −80° C. until use.
7. The pGAP-hph-AoMae plasmid was extracted, the plasmid was linearized with AvrII, and then transformed into *Pichia pastoris* GS115 competent cells by electroporation. Then 1 ml of pre-cooled 1M sorbitol was added and the mixture was left at 30° C. 2 h, and then was inoculated on the YPD plate containing 300 μg/ml. After the growth of bacteria to be used for malic acid production, the strain was named as P2.

III. Determination of Malic Acid Synthesis Capacity

Malate synthesis strain was first activated with YPD medium for 48 h, and then inoculated with initial OD 600=1.0 on malate-producing medium (100 g/L glucose, 1.24 g/L KNO$_3$, 0.64 g/L KH$_2$PO$_4$, 0.04 g/L ZnSO$_4$.7H$_2$O, 0.25 g/L MgSO$_4$.7H$_2$O, 0.0005 g/L FeSO$_4$.7H$_2$O 4 g/L peptone, 0.1 g/L CaCl$_2$, 75 g/L CaCO$_3$, 0.1 g/L histine, biotin 4×10$^{-4}$ g/L), wherein 30 ml liquid medium was added into a 250 ml triangle bottle liquid, and cultured at 200 rpm, 30° C. incubation. Every 24 h, 1 ml was sampled, 1 ml 20% (V/V) H$_2$SO$_4$ was added, and acidification treatment was conducted at 80° C. for 30 min. A certain amount of water was added for dilution and after centrifugation, the supernatant was taken and HPLC Aminex 87H chromatographic column was used to measure the content of malic acid. The HPLC parameter conditions were as follows: the column temperature was 35° C., the detector temperature was 40° C., the mobile phase was 5 mM H$_2$SO$_4$, the flow rate was 0.5 ml/min, and the malic acid standard was used for quantification. Compared with the GS115 strain, the P2 strain produced 5.0 g/l malic acid and GS115 produced 1.0 g/L malic acid.

Example 4 Construction and Screening of Pyruvate Carboxylase Mutation Library

I. Construction of Pyruvate Carboxylase Expression Vector. The Primers were as Follows:

```
his-BglII
                                    SEQ ID NO: 119
GGGAGATCTGTTGTAACACTGGCAGAGCATTACG his-BamH1
                                    SEQ ID NO: 120
GGGGGATCCGTCCCAGTTTCTCCATACGAACC
```

Using the pPIC9K plasmid as a template, PCR was conducted to amplify his gene, and the PCR fragment was digested with BglII and BamH1 and ligated with pGAPzA digested with BglII to obtain pGAPzA-his. Pyruvate carboxylase derived from *Penicillium* and *Rhizobium* was synthesized by Jin Weizhi Company. The primers were as follows:

```
PyPyc-F
                                    SEQ ID NO: 121
GGGTTCGAAATGGCCGCGCCGCAACGCCAACCCG

PyPyc-R
                                    SEQ ID NO: 122
GGGGCGGCCGCTCATCAGGCCTTGCCGATCTTAC

RePyc-F
                                    SEQ ID NO: 123
GGGTTCGAAATGCCCATTAGCAAGATCCTCGTGGC

RePyc-R
                                    SEQ ID NO: 124
GGGGCGGCCGCTCAGCCGCCGTAGACCGCGAGGAG
```

Then, the gene was digested with BstBI and NotI and ligated with the same digested pGAPzA-his, and transformed into *E. coli* DH5α. The sequences of transformants were confirmed correct by sequencing, and plasmids were named as pGAPzA-his-PvPyc and pGAPzA-his-RePyc (FIG. 6)). As for the pyruvate carboxylase from *Aspergillus*,

*Rhizopus oryzae, Corynebacterium glutamicum* and *Pichia pastoris*, the primers were as follows:

```
AoPyc-F
                                  SEQ ID NO: 125
GGGTTCGAAATGGCGGCTCCGTTTCGTCAGCC

AoPyc-R
                                  SEQ ID NO: 126
GGGGCGGCCGCCTATTACGCTTTGACGATCTTGC

RoPyc-F
                                  SEQ ID NO: 127
AATTGAACAACTATTTCGAAATGCCTGCTGCACC

RoPyc-R
                                  SEQ ID NO: 128
AGAAAGCTGGCGGCCGCTTAGGCTTCCTCTTTGAC

CgPyc-F
                                  SEQ ID NO: 129
CAATTGAACAACTATTTCGAAATGTCGACTCACAC

CgPyc-R
                                  SEQ ID NO: 130
CTAGAAAGCTGGCGGCCGCCTATTAGGAAACGAC

PpPyc-F
                                  SEQ ID NO: 131
GGGTTCGAAATGGCCGAAGAAGACTACTCCCCGC

PpPyc-R
                                  SEQ ID NO: 132
GGGGCGGCCGCTTACTCAGCCTTGACGATTTTGGC
```

Figure 6:
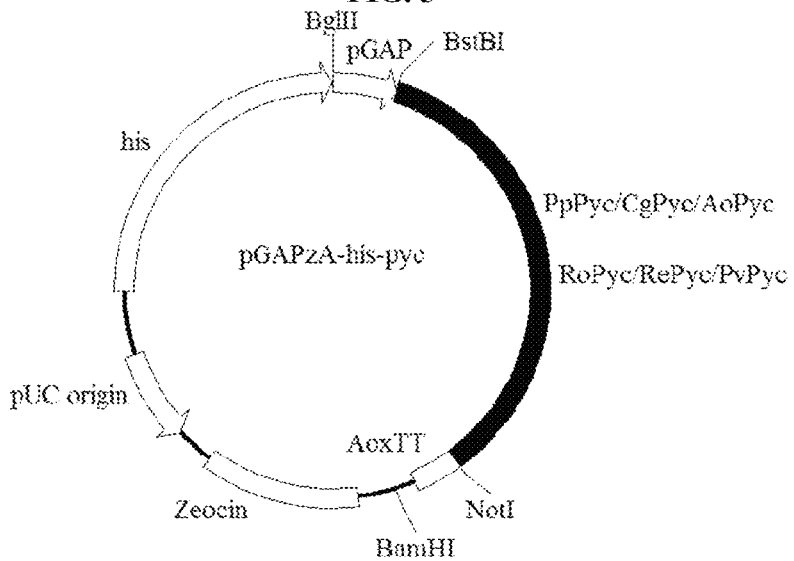
FIG. 6 shows a map of pyc directed evolution engineered plasmid.

PCR amplification was conducted by using the respective genomic DNA as a template, and the PCR reaction system was as follows: 5× phusion HF buffer 10 μl 10 mM dNTPs 1 μl, AvrII-F 1 μl, AvrII-R 1 μl, pGAPzA 1 μl, Phusion DNA polymerase 0.5 μl, Water 35.5 μl. The PCR reaction conditions were as follows: first 98° C. 30 s; then 98° C. 10 s, 60° C. 30 s, 72° C. 3 min, 30 cycles; finally 72° C. 10 min, 4° C. 10 min. After the PCR product was purified by the purification column, it was digested with BstBI and NotI (the cleavage site contained in the gene was eliminated by mutation), and ligated with the vector pGAPzA-his, transformed into *E. coli* DH5α. The sequences of transformants were confirmed correct by sequencing, and plasmids were named as pGAPzA-his-AoPyc, pGAPzA-his-RoPyc, pGAPzA-his-CgPyc and pGAPzA-his-PpPyc (FIG. 6).

II. Comparison of Candidate Genes for Pyruvate Carboxylase

Figure 28:
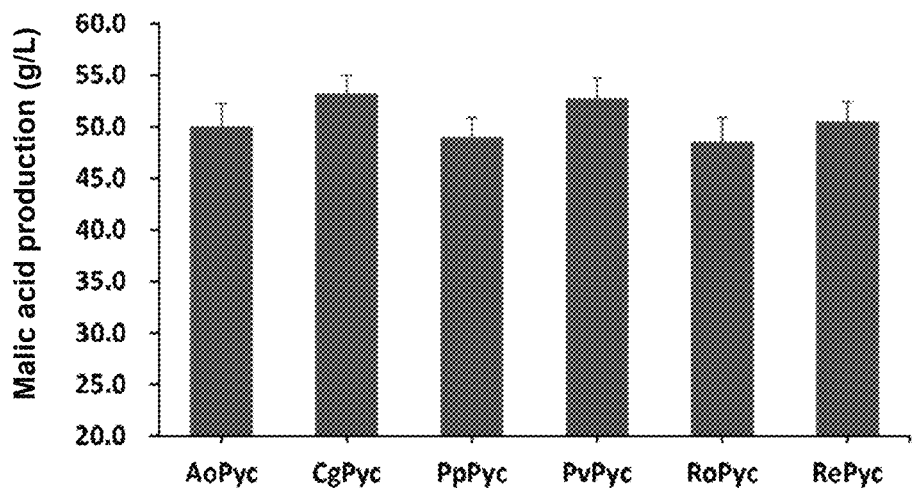
FIG. 28 shows the effect of pyc from different sources on malic acid production. Among them, the production of malic acid by *Corynebacterium glutamicum* is up to 53.2 g/L.

After digesting 6 pyruvate carboxylase expression vectors constructed above with AvrII, the candidate genes were transferred via electroporation into *Pichia pastoris* P2 strain containing the dicarboxylic acid transporter AoMae, inoculated on MD plates. After the bacteria grew out, a single clone was picked, activated in YPD liquid medium for 48 h, and the acid-generating medium was used to perform shake flask cultivation. The results were shown in FIG. 28, in which pyruvate carboxylase derived from *Corynebacterium glutamicum* was more favorable for the synthesis of organic acids such as malic acid. Using 100 g/L glucose as the substrate, 53.2 g/L malic acid could be synthesized so that this protein was used as a starting protein for protein engineering.

Figure 29:
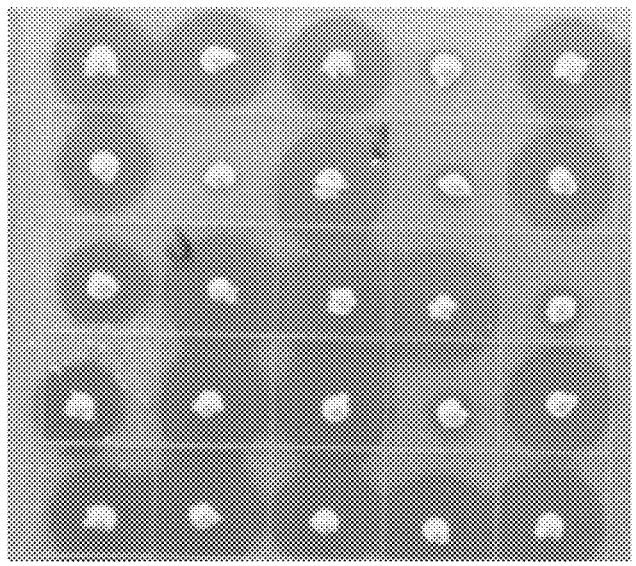
FIG. 29 shows the preliminary screening of PYC based on the hydrolysis circle on an inoculating plate
Figure 30:
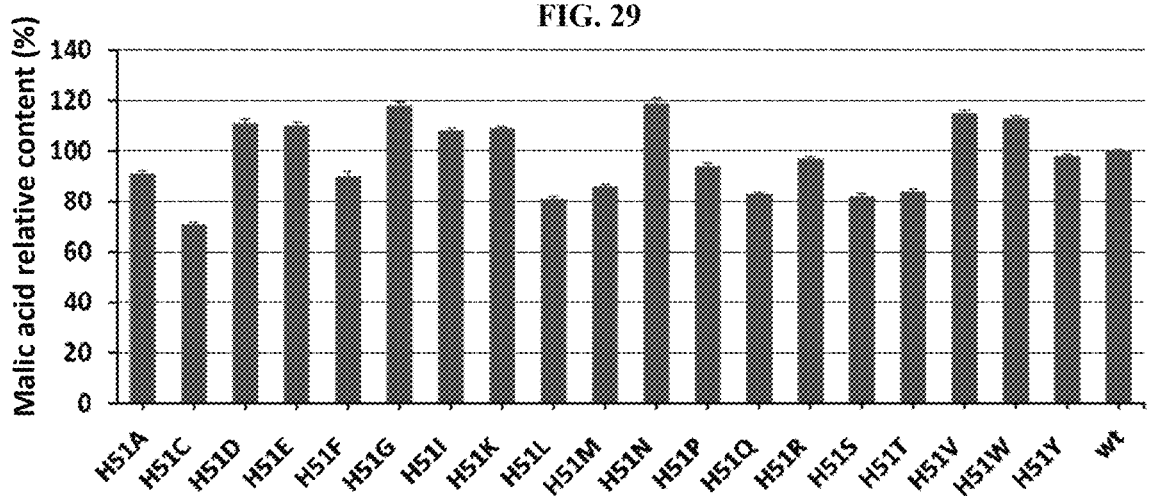
FIG. 30 shows the effect of CgPyc H51 saturation mutation on malic acid production. Among them, H51N and H51G increased malic acid production by 19% and 18%, respectively.
Figure 31:
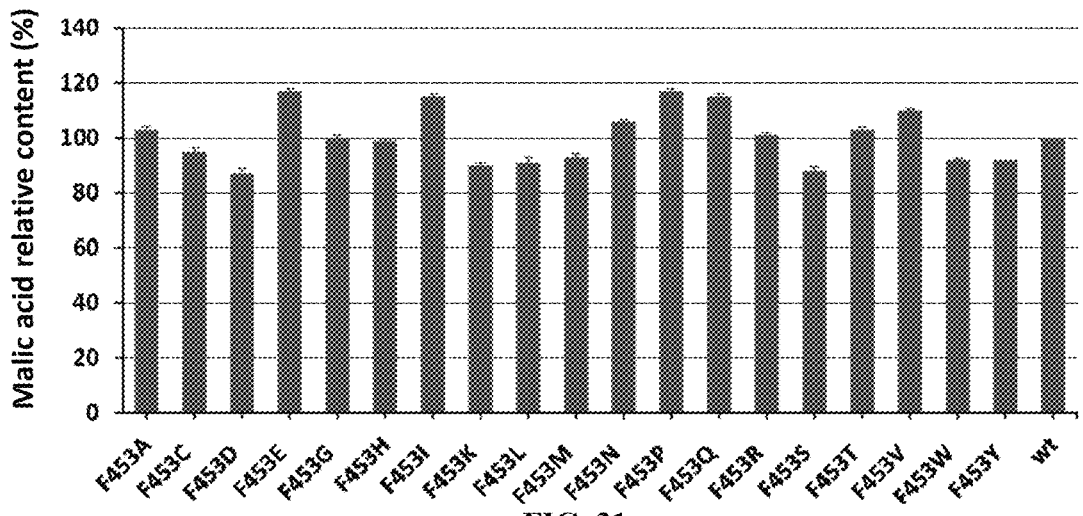
FIG. 31 shows the effect of CgPyc F453 saturation mutation on malic acid production. Among them, F453E and F453P increased malic acid production by 17% and 17%, respectively.
Figure 32:
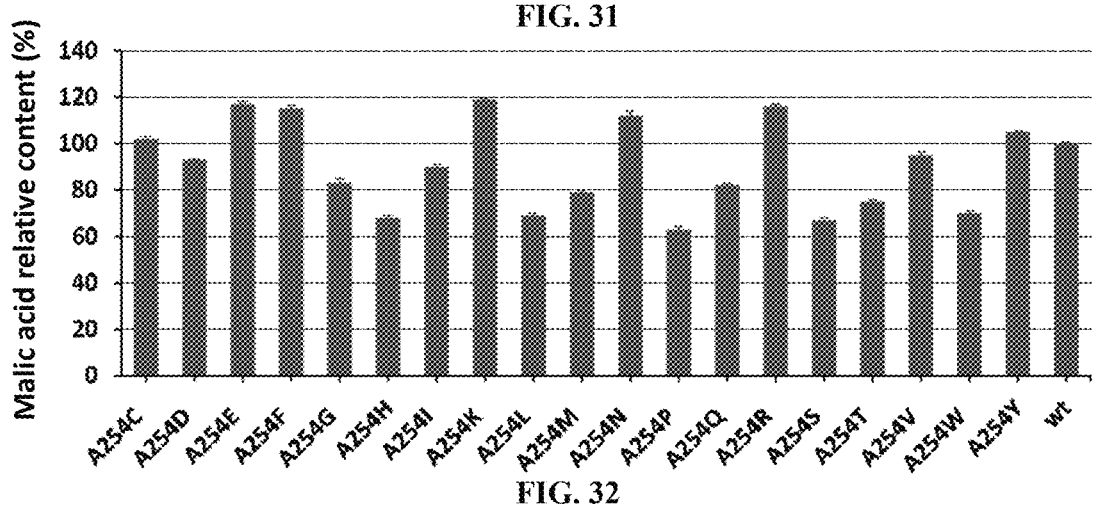
FIG. 32 shows the effect of CgPyc A254 saturation mutation on malic acid production. Among them, A254K, A254E, A254R and A254F increased malic acid production by 19%, 17%, 16% and 15%, respectively.
Figure 33:
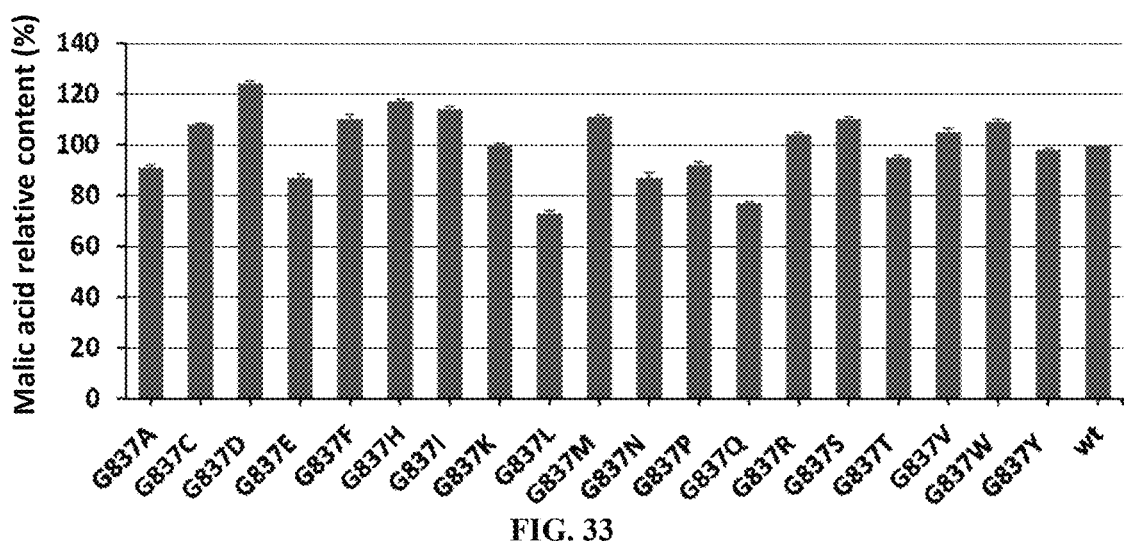
FIG. 33 shows the effect of CgPyc G837 saturation mutation on malic acid production. Among them, G837D and G837H increased malic acid production by 24% and 17%, respectively.
Figure 34:
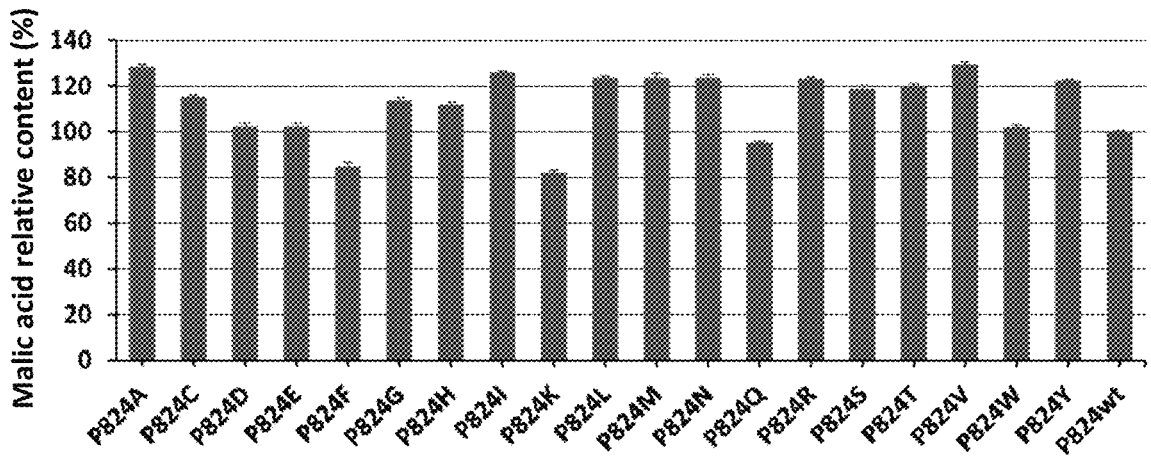
FIG. 34 shows the effect of CgPyc P824 saturation mutation on malic acid production. Among them, P824V, P824A, P824I, P824Y, P824L, P824M, P824N, P824R, P824T increased malic acid production by 29.4%, 28.2%, 25.9%, 22.4%, 23.5%, 23.5%, 23.6%, 23.2%, 20%, respectively.
Figure 35:
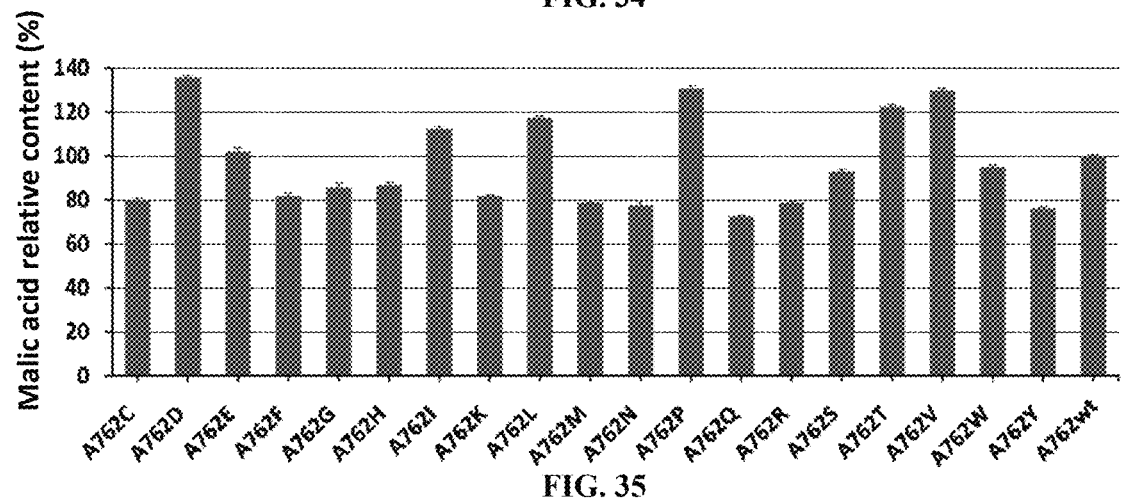
FIG. 35 shows the effect of CgPyc A762 saturation mutation on malic acid production. Among them, A762D, A762P, A762V and A762T increased malic acid production by 33.5%, 30.6%, 29.6% and 22.4%, respectively.
Figure 36:
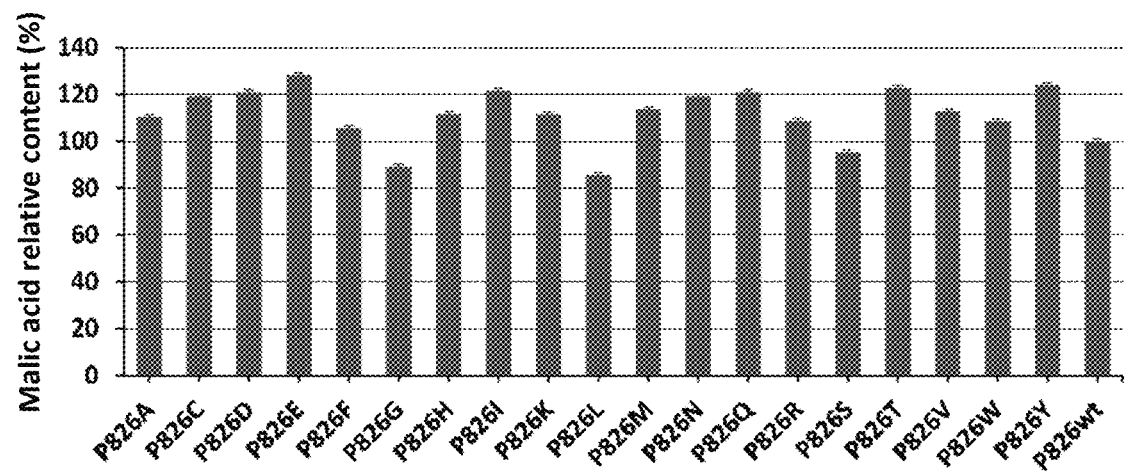
FIG. 36 shows the effect of CgPyc P826 saturation mutation on malic acid production. Among them, P826E, P826Q, P826Y, P826T, P826D, P826I increased malic acid production by 28.3%, 20.9%, 24.1%, 22.9%, 20.9%, and 21.6%, respectively.
Figure 37:
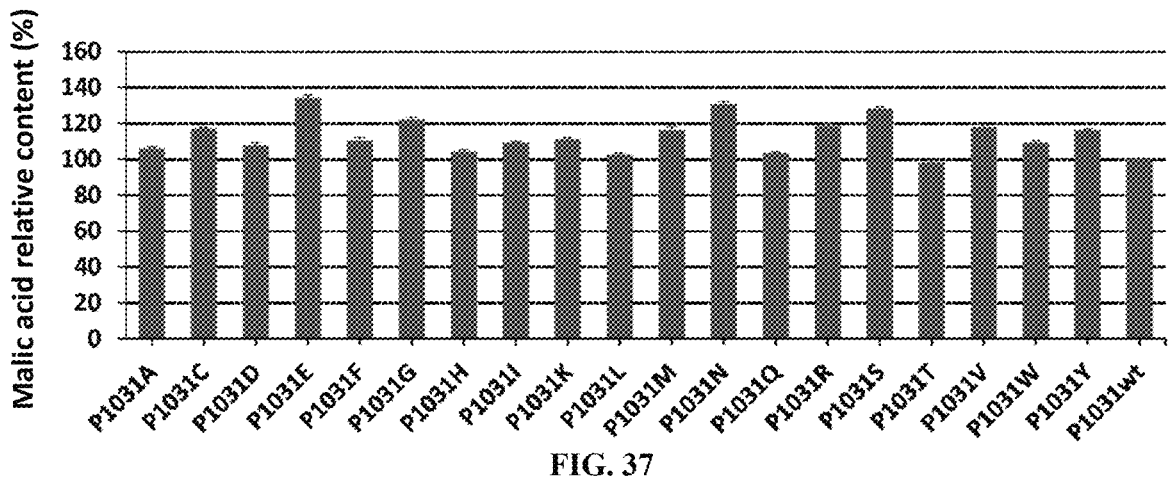
FIG. 37 shows the effect of CgPyc P1031 saturation mutation on malic acid production. Among them, P1031E, P1031N, P1031S, and P1031G increased malic acid production by 34.2%, 30.8%, 128.2%, and 122.2%, respectively.

III. Construction of High-Throughput Screening Method Based on Hydrolysis Circle:

Due to the soluble properties of 20-30 g/L calcium malate (found in the early stage of the present study), we established a high-throughput screening method based on hydrolysis circle. The specific method was as follows: when pyruvate carboxylase was transformed into P2 competent cells, after the growth of bacterial clone, the clone was pick with a sterile toothpick, and then was punctured into the malic acid-producing solid medium (2.0 g/L agar was added to the liquid, and the concentration of $CaCO_3$ was 3 g/L). The size of the hydrolysis circle was checked every day, the ratio of the diameter of the hydrolysis circle to the diameter of the clone was used as the screening criterion: the larger the value, the higher the malic acid production (FIG. 29).

IV. Construction of PYC Mutation Library and Screening of Malate-Producing Mutants:

Protein engineering of pyruvate carboxylase CgPyc derived from *Corynebacterium glutamicum*. First, BstBI and NotI sites contained in CgPyc were mutated by using the following primers:

```
BstBI-mut-F
                                  SEQ ID NO: 133
TGGGCCTTGCGGATCGTTTCGAGCTC BstBI-mut-R
                                  SEQ ID NO: 134
ACGATCCGCAAGGCCCAGTGCGGTGGC NotI-mut-F
                                  SEQ ID NO: 135
TGCTGCTTCGCGGTCGCAAC NotI-mut-R
                                  SEQ ID NO: 136
CGAAGCAGCATCTGAATGTTTAC
```

Using the same site-directed mutation as in Example 2, the obtained plasmid pGAPZA-his-CgPyc (BstBI NotImut) was used as a template for random CgPyc mutations and site-directed mutations. The primers were as follows:

```
CgPyc-ep-F
                                  SEQ ID NO: 137
GGGTTCGAAATGTCGACTCACACATCTTC

CgPyc-ep-R
                                  SEQ ID NO: 138
GGGGCGGCCGCTTAGGAAACGACGACGATCAAG
```

The random mutation kit GeneMorph II Random Mutagenesis (Agilent) was used to perform random mutation amplification of CgPyc. The PCR product was digested with BstB1 and NotI and then ligated with pGAPzA-his, and the ligated product was transformed into *E. coli* competent cell DH5α, inoculated on LB solid plate medium containing 25 μg/ml Zeocin, and cultured overnight at 37° C. 20 single clones were randomly picked for sequencing, and the mutation rate was analyzed. The results showed that the mutation rate was about 1%. The mutant library was eluted with LB liquid medium containing 25 μg/ml Zeocin, and then recovered at 37° C. for 2 h. Then the mixed plasmid was extracted, transformed into P2 competent cells after linearization with AvrII, and spread on MD plates. After the single clones grew, single clone was punctured and inoculated in malate-producing solid medium. Using CgPyc wild-type strain as a control, strains with a larger hydrolysis circle than the wild-type CgPyc in the mutation library were rescreened in shaking flask and malate content was determined by HPLC.

V. Identification of Mutation Sites:

For mutant strains with increased malic acid production, their genomic DNA was extracted, and then CgPyc-F and CgPyc-R were used as primers for PCR amplification. After the amplification product was recovered by purification columns, is was ligated with pJET1.2 blunt vector, transformed into *E. coli* competent cell DH5α, inoculated on LB medium containing 100 μg/ml ampicillin, and the monoclones were sequenced to obtain the mutation sites: $H_{51}E$, F453Q, A254N, G837M, A762T, P824L, P826T, P1031S.

VI. Site Saturation Mutations and Combination Mutations of CgPyc Improved Malic Acid Synthesis:

Saturated mutations were conducted at key amino acid positions obtained from random mutation sites. The method was as follows: the mutation sites was introduced in the middle of primers; then PCR was performed to amplify pGAPzA-his-CgPyc; the PCR product was digested with DpnI; the template plasmid was removed, and then 5 μl of transformed *E. coli* competent cell DH5a was taken and inoculated on LB medium containing 25 μg/ml Zeocin. The mutant sites were obtained by sequencing the single clones. After the obtained CgPyc mutant expression plasmid was linearized with AvrII, the P2 strain was transformed, and then subjected to liquid malate production medium for shake flask cultivation and HPLC analysis was conducted. The introduction of the mutation was as follows:

H51E mutation was obtained by using primers $H_{51}E$ (SEQ ID NO: 139): GAAGATCGGGGATCATTCGAGCGCTCTTTTGCTTCTG and $H_{51}$-rev (SEQ ID NO: 140): GAATGATCCCCGATCTTC. For other $H_{51}X$ mutation (X represents 18 other amino acids except F), Primers $H_{51}X$ (SEQ ID NO: 141): GAAGATCGGGGATCATTCXXXCGCTCTTTTGCTTCTG (XXX was a codon corresponding to different amino acids) and $H_{51}$-rev (SEQ ID NO: 140) were used to introduce mutation.

F453Q mutation was obtained by using primers F453Q (SEQ ID NO: 142): AGCGCATCGCCACCGGACAAATTGCCGATCACCCGCAC and F453-rev (SEQ ID NO: 143): TCCGGTGGCGATGCGCTTG. For other F453X mutation (X represents 18 other amino acids except F), Primers F453X (SEQ ID NO: 144): AGCGCATCGCCACCGGAXXXATTGCCGATCACCCGCAC (XXX was a codon corresponding to different amino acids) and F453-rev (SEQ ID NO: 143) were used to introduce mutation.

A254N mutation was obtained by using primers A254N (SEQ ID NO: 145): AGTTGTCGAAATTGCGCCAAACCAGCATTTGGATCCAG and A254-rev (SEQ ID NO: 146): TGGCGCAATTTCGACAAC. For other A254X mutation (X represents 18 other amino acids except F), Primers A254X (SEQ ID NO: 147): AGTTGTCGAAATTGCGCCAAACCAGCATTTGGATCCAG (XXX was a codon corresponding to different amino acids) and A254X-rev (SEQ ID NO: 146) were used to introduce mutation.

G837M mutation was obtained by using primers G837M (SEQ ID NO: 148): TACCGCCACGAAATCCCAATGGGACAGTTGTCCAACCTG and G837-rev (SEQ ID NO: 149): TGGGATTTCGTGGCGGTAG. For other G837X mutation (X represents 18 other amino acids except F), Primers G837X (SEQ ID NO: 150): TACCGCCACGAAATCCCAXXXGGACAGTTGTCCAACCTG (XXX was a codon corresponding to different amino acids) and G837-rev (SEQ ID NO: 149) were used to introduce mutation.

A762T mutation was obtained by using primers A762T (SEQ ID NO: 151): GCTCAAGCTGGTACCGATGCTGTTGACGGTGCTTC and A762-rev (SEQ ID NO: 152): ACCAGCTTGAGCTGCAGC. For other A762X mutation (X represents 18 other amino acids except F), Primers A762X (SEQ ID NO: 153): GCTCAAGCTGGTXXXGATGCTGTTGACGGTGCTTC (XXX was a codon corresponding to different amino acids) and A762-rev (SEQ ID NO: 152) were used to introduce mutation.

P824L mutation was obtained by using primers P824L (SEQ ID NO: 154): TTGAGTCTGGAACCTTGGGCCCAACCGGTCGC and P824-rev (SEQ ID NO: 155): GGTTCCAGACTCAAATGGCAGG. For other P824X mutation (X represents 18 other amino acids except F), Primers P824X (SEQ ID NO: 156): TTGAGTCTGGAACCXXXGGCCCAACCGGTCGC (XXX was a codon corresponding to different amino acids) and P824-rev (SEQ ID NO: 155) were used to introduce mutation.

P826T mutation was obtained by using primers P826T (SEQ ID NO: 157): CTGGAACCCCAGGCACCACCGGTCGCGTCTAC and P826-rev (SEQ ID NO: 158): GCCTGGGGTTCCAGACTC. For other P826X mutation (X represents 18 other amino acids except F), Primers G837X (SEQ ID NO: 159): CTGGAACCCCAGGCXXXACCGGTCGCGTCTAC (XXX was a codon corresponding to different amino acids) and P826-rev (SEQ ID NO: 158) were used to introduce mutation.

P1031S mutation was obtained by using primers P1031S (SEQ ID NO: 160): TGCGATCTCTGAGTCCGACGATAAGGGTATGC and P1031-rev (SEQ ID NO: 161): CTCAGAGATCGCATCCAGGC. For other P1031X mutation (X represents 18 other amino acids except F), Primers P1031X (SEQ ID NO: 162): TGCGATCTCTGAGXXXGACGATAAGGGTATGC (XXX was a codon corresponding to different amino acids) and P1031-rev (SEQ ID NO: 161) were used to introduce mutation.

Figure 38:
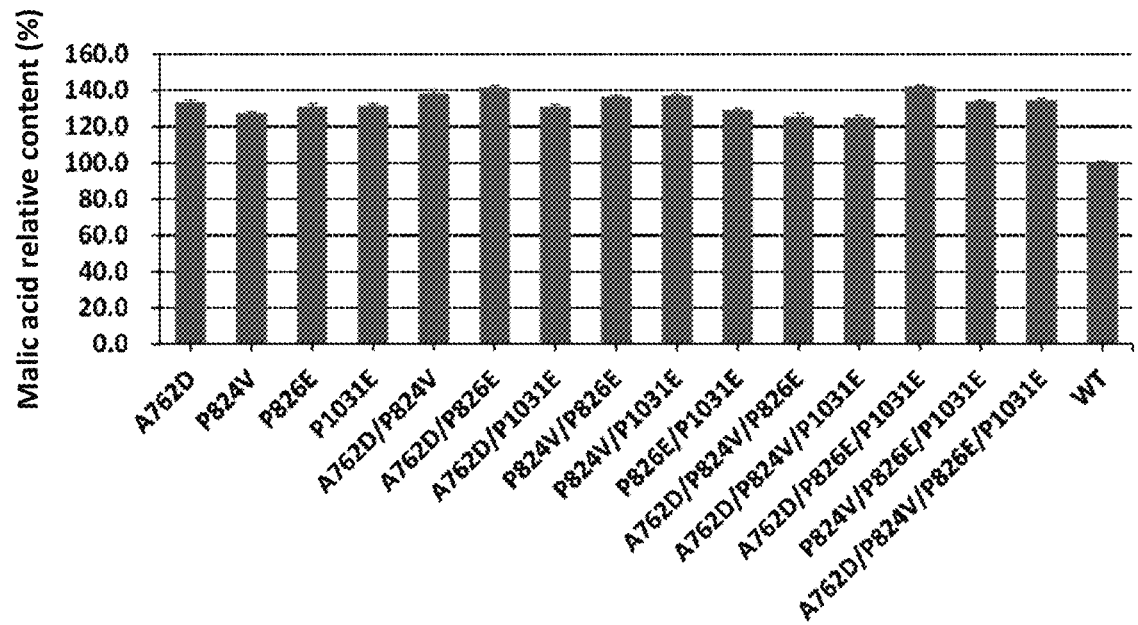
FIG. 38 shows the effect of CgPyc combination mutations on malate production. Among them, A762D/P826E, A762D/P824V, P824V/P826E, P824V/P1031E, A762D/P826E/P1031E increased malate production by 41.4% and 38.6%, 36.7%, 37.1%, and 42.3% respectively.

All mutants were transformed into P2 competent cells, and the results of screening malic acid were shown in FIGS. 30-37. For the mutation points where the positive mutation effect was better, A762D, P824V, P826E and P1031E (these four points could increase malic acid by 35.7%, 29.4%, 28.3%, and 34.2%, respectively) were selected for Combination mutation. Using the same method as saturation mutation, and the combination mutation was used to transform P2 strain, and the malate production results were shown in FIG. 38, wherein A726D/P826E and A762D/P824E/P1031E could increase malic acid by 41.4% and 42.3%, respectively, and the final malic acid synthesis capacity reached 75.2 g/L and 75.5 g/L.

Example 5 Application of Aomae in *Saccharomyces cerevisiae* to Synthesize Malic Acid I. Construction of Pyc, Mdh and AoMae Co-Expression Plasmid Vectors.

The primers were as follows:

| | | |
|---|---|---|
| Prs426-ScPYC2-gibson-F | SEQ ID NO: 163 | CAACTAGTGGATCCCCCGGGCTGCAGG AATTCATGAGCAGTAGCAAGAAATTGG CCG |
| T2A1-ScPYC2-gibson-R | SEQ ID NO: 164 | CTCAACGTCACCGCAAGTAAGCAAAGA ACCTCTACCCTCAGCTCTCTTTTTTTG GGATGGGGGTAGGG |
| T2A1-Aomae-gibson-F | SEQ ID NO: 165 | CTTTGCTTACTTGCGGTGACGTTGAGG AAAACCCAGGTCCAATGCTGACACCTC CCAAGTTTGAGG |
| T2A2-Aomae-gibson-R | SEQ ID NO: 166 | CATCTCCGCAGGTCAAAAGGGATCCAC GTCCTTCGGCACGATCAGATACATCCT CATCTTTACC |

```
T2A2-ScMDH3Δ      SEQ ID    GACGTGGATCCCTTTTGACCTGCGGAG
SKL-gibosn-F      NO: 167   ATGTCGAAGAGAATCCTGGACCTATGG
                            TCAAAGTCGCAATTCTTGGCGC ScMDH3 Δ          SEQ ID    CCCCTCGAGGTCGACGGTATCGATAAG
SKL-gibson-R      NO: 168   CTTTCAAGAGTCTAGGATGAAACTCTT
                            GCC
```

Using *S. cerevisiae* CENPK.2-1C DNA and *Aspergillus oryzae* cDNA as templates, PCR was conducted to amplify ScPYC2, AoMae and MDH3 (removing mitochondrial localization sequence SKL). Three gene fragments were ligated into EcoRI and HindIII site of Prs426-pgk-CYCtt vector via Gibson method, and the three genes constituted a single cistron via 2A peptide (raegrgslltcgdveenpg), and the expression plasmid Prs426-PGK-ScPYC2-Aomae-MDH3ASKL was obtained.

II. Construction of *Saccharomyces cerevisiae* Producing Malic Acid

Figure 39:
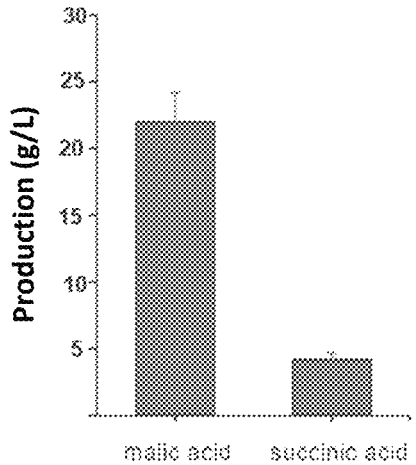
FIG. 39 shows *Saccharomyces cerevisiae* which expresses PYC, AoMae, and MDH to produce malate, and the three gene co-expressing strain could produce 22 g/L malate.
Figure 40:
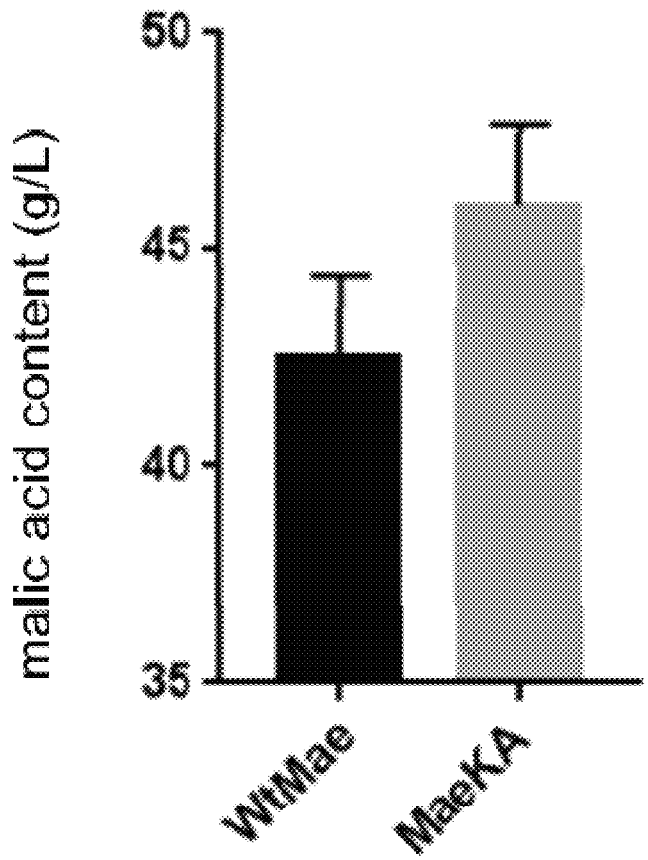
FIG. 40 shows malic acid production of a strain which overexpresses mutant malic acid transporter. Among them, the overexpression mutant having Aomae I80K/R272A increased malic acid production by 9.5%.
Figure 41:
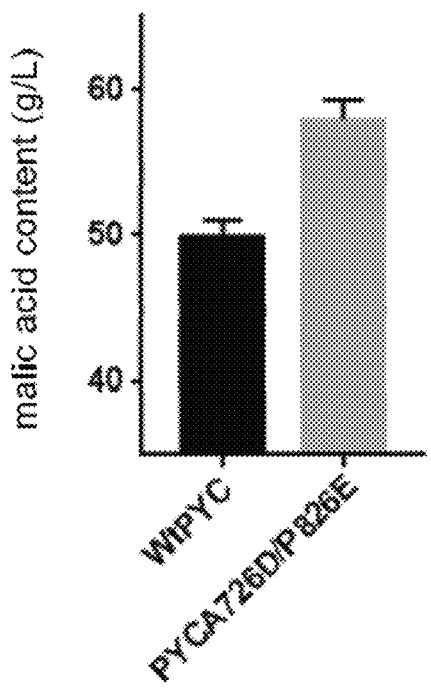
FIG. 41 shows malic acid production of a strain which overexpresses mutant pyruvate carboxylase. Among them, overexpression mutant having CgPYC A762D/P826E/P1031E increased malic acid production by 16%.

The plasmid Prs426-PGK-ScPYC2-Aomae-MDH3ASKL was transformed into *S. cerevisiae* CEN.PK2-1C by LiAc/SS Carrier DNA method (Methods Mol Biol. 2014; 1205: 1-12.) Malic acid synthesis was carried out on the same medium as *Pichia pastoris* to produce malic acid. The results were shown in FIG. 39. The results showed that 100 g/l glucose could produce 22 g/l malic acid.

Example 6 Modification of C4-Dicarboxylic Acid Transporter Encoding Gene Mae Improves *Myceliophthora thermophila* Malate Synthesis Capacity I. Construction of Mae Overexpression Vector C4-dicarboxylic acid transporter encoding gene mae (XM_001820829.2, SEQ ID NO: 1) and the mutant gene maeKA were amplified from the cDNA and plasmid pGAP-hph-his-AoMaeKA of *Aspergillus oryzae* DSM1863 (DSMZ, purchased from German Microbial and Cell Culture Co., Ltd.), digested with BglII, ligated into the linearized vector pAN52-hph digested with BglII and EcoRV. The ligation product was confirmed by digestion with restriction enzyme, thereby resulting in an overexpression vectors, named pAN52-Wtmae and pAN52-maeKA. The primers were as follows:

```
mae-F
                                             SEQ ID NO: 169
GGAAGATCTTAATTAACTCGAGCGGCCGCGTTTAAAC

ACTAGTATGCTGACACCTCCCAAGTTTG mae-R
                                             SEQ ID NO: 170
ATCCTAATCAGATACAT CCTCATCTTTA
```

Using the gene of the starting strain *Myceliophthora thermophila* ATCC42464 (purchased from American type culture collection) as a template, a 1.4 kb promoter (named Ptef promoter) upstream of the reading extension factor encoding reading frame (MYCTH_2298136) was amplified by PCR, and the primers were as follows:

```
tef-F
                                             SEQ ID NO: 171
CCTTAATTAACATGTACCTTGACGTCCTCCGAG tef-R
                                             SEQ ID NO: 172
GGACTAGTTCTGAAGAACGAAACTGGC GACT
```

After the PCR reaction was completed, the product was digested by PacI and SpeI, and ligated into the linearized vector pAN52-hph-mae which was double-digested by the same enzymes, and the ligated product was digested and identified with restriction enzymes. The mae gene expression vector under the control of promoter tef was named pAN52-Ptef-Wtmae and pAN52-Ptef-maeKA.

II. Introduction of the Expression Vector into *Myceliophthora thermophila*

A. *Myceliophthora thermophila* ATCC42464 was inoculated in MM slant medium [50× Vogel's salt 20 ml, sucrose 20 g, agar 15 g, histidine (50 mg/ml) 20 ml, adding water to 1 L, and sterilized with high pressure; 50× Vogel's salt (1 L): Trisodium citrate (½$H_2O$) 150 g, anhydrous $KH_2PO_4$ 250 g, anhydrous $NH_4NO_3$ 100 g, $MgSO_4.7H_2O$ 10 g, $CaCl_2.2H_2O$ 5 g, trace element salt solution 5 mL, biotin (0.1 mg/ml) 2.5 mL, adding water to 1 L].

B. *Myceliophthora thermophila* Protoplast Transformation

1) Mycelium Preparation

The mature *Myceliophthora thermophila* spores were collected with 0.05% Tween 80 sterilized water, filtered off mycelia through lens-cleaning paper, inoculated on MM plates covered with cellophane, and incubated at 45° C. for 14 hours.

2) Protoplast Preparation

Place cellophane with mycelium in 30 mL lysate (formulation: 0.15 g lyase, 30 mL solution A was added aseptically, and sterilized via filtration; Solution A: 1.0361 g $KH_2PO_4$, 21.864 g sorbitol, Dissolved in 90 ml deionized water, adjusted to pH 5.6 with potassium hydroxide, quantitative to 100 ml, high temperature sterilization), pyrolysis at 28° C. for 2 h, shaking gently every 20 min.

After filtering through cellophane, centrifuge at 2000 rpm and 4° C. for 10 min, discard the supernatant, add 4 mL of solution B (0,735 g calcium chloride, 18, 22 g sorbitol, 1 ml TrisHCl 1M pH7.5, dissolved in 90 ml deionized. Adjust the pH to 7.6 with water and hydrochloric acid, quantify to 100 ml, and sterilize at high temperature), centrifuge at 2000 rpm and 4° C. for 10 min; discard the supernatant and add a certain volume of solution B according to 200 μl/plasmid.

3) Protoplast Transformation

Into a pre-chilled 15 ml centrifuge tube, 50 μl pre-chilled PEG (12.5 g PEG6000, 0.368 g calcium chloride, 500 μl Tris HCl 1M pH 7.5), 100 plasmid linearized with HindIII, and 2000 protoplast were added. After placing on ice for 20 min, 2 ml of pre-chilled PEG was added, placed at room temperature for 5 min, 4 mL of solution B was added, and mixed gently. 3 ml of the above solution was taken into 12 ml of melted MM medium containing the corresponding antibiotics, placed in a plate, and culture at 45° C. After 2 d-4 d, a single mycelium was picked under a stereomicroscope and allowed to grow on the corresponding resistant plate, and then PCR verification was conducted.

III. Determination of Malic Acid Production Ability of *Myceliophthora thermophila* Transformants All the above verified transformants were inoculated into 50 mL medium in a 250 ml triangular flask with crystalline cellulose (Avicel) as the carbon source (formula: carbon source 75 g/l, peptone 6.0 g/l, 0.15 g/l $KH_2PO_4$, 0.15 g/l K2HPO4, 0.10 g/l $CaCl_2.2H_2O$, 0.10 g/l $MgSO_4.7H_2O$, calcium carbonate 80.0 g/l, 1 mL/L 0.5 g/l biotin, 1 ml/l trace element solution; trace element formula (100 ml): 5 g $C_6H_8O \cdot 7H_2O$, 5 g $ZnSO_4 \cdot 7H_2O$, 1 g $Fe(NH_4)_2(SO_4) \cdot 6H_2O$, 0.25 g $CuSO_4 \cdot 5H_2O$, 0.05 g $MnSO_4 \cdot H_2O$, 0.05 g $H_3BO_3$, 0.05 g $NaMoO_4 \cdot 2H_2O$, dissolved in water, and water was added to 100 ml). The inoculation volume was $2.5 \times 10^5$/ml (45° C., 150 rpm cultivation). Sample was taken on the eighth day to determine the malic acid content.

1) Sample Processing:

Take 1 ml of fermentation broth in a 15 ml centrifuge tube, and add 1 ml of 1M $H_2SO_4$, then place at 80° C. for 30 min, and shake thoroughly every 10 min. Then add 2 ml of double-distilled water into the centrifuge tube, shake it well, take 1 ml of liquid in a 1.5 ml centrifuge tube, centrifuge at 12000 rpm for 10 min, and take the supernatant to measure the malic acid content.

2) Determination of Malic Acid Content

The processed samples were determined by high performance liquid chromatography, where the detector was a UV detector, 5 mM $H_2SO_4$ was the mobile phase, and the flow rate was 0.5 ml/min. The results showed that the malate transporter, after mutation, could significantly promote malate production as compared to the wild-type transporter. On the eighth day, the malic acid production of the transformant MaeKA was 46 g/l, which was an increase of 9.5% compared with the control strain WtMae (42 g/l). The experiment showed that the mutated C4-dicarboxylic acid transporter could significantly increase the production capacity of malate in the thermophilic fungus such as *Myceliophthora thermophila*.

Example 7 Modified TCA Key Enzyme Pyruvate Carboxylase Improves *Myceliophthora thermophila* Malate Synthesis Capacity I. Construction of Overexpression Vector The pyruvate carboxylase gene Cgpyc and its mutated gene CgpycA726D/P826E were amplified from the *Corynebacterium glutamicum* ATCC13032 genome and the plasmid pGAPzA-his-CgPycDE, respectively, and digested by SpeI and EcoRV, and then ligated into linearized vector pAN52-C1pgdA-neo digested with the same endonuclease, and the ligation product was identified by digestion with restriction enzyme, thereby obtaining the overexpression vectors, named pAN52-Wtpyc and pAN52-pycA726D/P826E. The primers were as follows:

```
CgPYC-F
                                SEQ ID NO: 173
GGACTAGTATGTCGACTCACACATCTTCA

CgPYC-R
                                SEQ ID NO: 174
AAAAAGATATCTTAGGAAACGACGACGATCAAG
```

II. Determination of Malic Acid Production Ability of *Myceliophthora thermophila* Transformants The overexpression vectors pAN52-Wtpyc and pAN52-pycA726D/P826E were linearized by BglII and integrated into the genome of *Myceliophthora thermophila* WtMae strain. The 100 µg/ml G418 was used as a final concentration of screening antibiotic, and the method was shown in step II of Example 1. Using primers CgPYC-F and CgPYC-R, it was confirmed that the transformants were obtained, named as WtPYC and PYCA726D/P826E.

All the verified transformants were inoculated into 50 ml in a 250 ml triangular flask with crystalline cellulose (Avicel) as the carbon source medium (for formula, see step III in Example 1). The inoculation amount was $2.5 \times 10^5$/ml (cultured at 45° C., 150 rpm), and sample was taken on the eighth day. After the sample was processed by the method described in Step 3.2 of Example 1, the malic acid content in the fermentation broth was determined.

The results showed that compared with wild-type pyruvate carboxylase, the mutation can significantly increase the malate production of transformants. On the eighth day, the maltate production of the transformant WtPYC was 49.9 g/l, while the malate production of the transformant overexpressing the mutant pyc reached 57.9 g/l with an increase of 16%. The experiment shows that after protein modification to increase the activity of pyruvate, the ability to synthesize malic acid in *Myceliophthora thermophila* can be significantly improved.

All documents mentioned in the present invention are incorporated herein by reference, as if each document were individually recited for reference. It should be understood that those skilled in the art will be able to make various changes or modifications to the present invention after reading the teachings of the present invention, which also fall within the scope of the invention defined by the appended claims of the application.

The invention claimed is:

1. A pyruvate carboxylase mutant protein, wherein the pyruvate carboxylase mutant protein has one or more amino acid mutations at positions corresponding to the amino acid sequence as shown in SEQ ID NO: 1 selected from the group consisting of:
   A762D, A762P, A762V, A762T, P826E, P826Q, P826Y, P826T, P826D and P826I;
   wherein the pyruvate carboxylase mutant protein has an activity of carboxylation of pyruvate into oxaloacetate, and wherein the amino acid sequence of the pyruvate carboxylase mutant protein has at least 90% sequence identity to the amino acid sequence of SEQ ID NO: 1.

2. The pyruvate carboxylase mutant protein of claim 1, wherein the amino acid sequence of the pyruvate carboxylase mutant protein has amino acid mutations at the following positions, as compared with SEQ ID NO: 1:
   A762D and P826E;
   A762D and P824V;
   P824V and P826E;
   P824V and P1031E; or
   A762D, P826E and P1031E.

3. The pyruvate carboxylase mutant protein of claim 1, wherein the pyruvate carboxylase mutant protein has the amino acid sequence of any one of SEQ ID NOs: 2-20, and 175.

4. An isolated polynucleotide, encoding the pyruvate carboxylase mutant protein of claim 1.

5. A vector comprising the isolated polynucleotide of claim 4.

6. A host cell, wherein the isolated polynucleotide of claim 4 is integrated into the genomic nucleic acid of the host cell; or wherein the host cell contains a vector, wherein the vector comprises the isolated polynucleotide of claim 4.

7. A method for obtaining the pyruvate carboxylase mutant protein of claim 1, comprising the steps of:
   i) culturing a host cell comprising a polynucleotide, which encodes the pyruvate carboxylase mutant protein of claim 1, under conditions suitable for expression of the pyruvate carboxylase mutant protein, thereby expressing the pyruvate carboxylase mutant protein of claim 1; and
   ii) isolating the expression product, thereby obtaining the pyruvate carboxylase mutant protein of claim 1.

8. A method for increasing the yield of malic acid, which comprises the steps of:
   i) introducing a polynucleotide encoding the pyruvate carboxylase mutant protein of claim 1 into a host cell;
   ii) in the presence of a carbon source, culturing the host cell, thereby expressing the pyruvate carboxylase mutant protein of claim 1;
   iii) converting pyruvate to oxaloacetate in the presence of the expressed pyruvate carboxylase mutant protein of claim 1, thus obtaining oxaloacetate in a higher yield than using the wild-type pyruvate carboxylase protein as shown in SEQ ID NO: 1;
   iv) subjecting oxaloacetate in the higher yield to an apple dehydrogenase then to a mutant malate transporter; and thus
   v) increasing the yield of malic acid from using the wild-type malate transporter as shown in SEQ ID NO: 22.

9. The method of claim 8, wherein the pyruvate carboxylase mutant protein has the amino acid sequence of any one of SEQ ID NOs: 2-20, and 175.

10. The method of claim 8, wherein the mutant malate transporter has the amino acid sequence of any one of SEQ ID NOs: 23-42, and 176.

11. A vector comprising the isolated polynucleotide of claim 4 and a polynucleotide encoding a malate transporter, wherein the malate transporter has the amino acid sequence as shown in SEQ ID NO: 22, or has the amino acid sequence of SEQ ID NO: 22 except for one or more amino acid mutations selected from the group consisting of:
   I80K, I80W, I80C, R272A, and R272F.

12. A host cell containing the vector of claim 11.

13. The pyruvate carboxylase mutant protein of claim 1, wherein the amino acid sequence of the pyruvate carboxylase mutant protein has an amino acid mutation as compared with SEQ ID NO: 1 selected from the group consisting of:
   P826E, P826Q, P826Y, P826T, P826D and P826I.

14. The pyruvate carboxylase mutant protein of claim 1, wherein the amino acid mutations comprise (a) one mutation selected from the group consisting of:
   A762D, A762P, A762V and A762T; and (b) an optional mutation selected from the group consisting of
   P826E, P826Q, P826Y, P826T, P826D and P826I;
   and
   wherein the pyruvate carboxylase mutant protein has an activity of carboxylation of pyruvate into oxaloacetate, and the amino acid sequence of the pyruvate carboxylase mutant protein has at least 95% sequence identity to the amino acid sequence of SEQ ID NO: 1.

15. The pyruvate carboxylase mutant protein of claim 13, wherein the sequence of the pyruvate carboxylase mutant protein has amino acid mutation(s) at the following position (s), as compared with SEQ ID NO: 1:
   P826E;
   A762D and P826E;
   P824V and P826E;
   P826E and P1031E;
   A762D, P826E and P1031E;
   P824V, P826E and P1031E; or
   A762D, P824V, P826E and P1031E.

16. The pyruvate carboxylase mutant protein of claim 1, wherein the pyruvate carboxylase mutant protein has the amino acid sequence of any one of SEQ ID NOs: 3, 10, 12, 14, 16, 17, 19 and 20.

17. The pyruvate carboxylase mutant protein of claim 1, wherein the pyruvate carboxylase mutant protein has an activity (cA1) of converting pyruvic acid into oxaloacetate via carboxylation, wherein the activity cA1 is higher than the corresponding activity (cA0) of the wild-type pyruvate carboxylase as shown in SEQ ID NO: 1, and wherein cA1−cA0)/cA0 is equal to or more than 15%.

* * * * *